US007141379B2

(12) United States Patent
Sakano et al.

(10) Patent No.: US 7,141,379 B2
(45) Date of Patent: Nov. 28, 2006

(54) METHOD OF SUPPRESSING DIFFERENTIATION BY ADMINISTERING A HUMAN SERRATE-1 POLYPEPTIDE

(75) Inventors: Seiji Sakano, Shizuoka (JP); Akira Itoh, Shizuoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 100 days.

(21) Appl. No.: 09/995,593

(22) Filed: Nov. 29, 2001

(65) Prior Publication Data
US 2002/0128197 A1 Sep. 12, 2002

Related U.S. Application Data

(62) Division of application No. 09/068,740, filed as application No. PCT/JP96/03356 on Nov. 15, 1996, now Pat. No. 6,337,387.

(30) Foreign Application Priority Data
Nov. 17, 1995 (JP) .................................. 7-299611
Nov. 30, 1995 (JP) .................................. 7-311811

(51) Int. Cl.
*G01N 33/53* (2006.01)
(52) U.S. Cl. ..................... 435/7.1; 435/7.21; 435/7.24
(58) Field of Classification Search ................ 514/2, 514/8, 12; 424/85.1; 435/7.1, 7.2
See application file for complete search history.

(56) References Cited

U.S. PATENT DOCUMENTS 5,869,282 A    2/1999   Ish-Horowicz et al.

FOREIGN PATENT DOCUMENTS

| WO | WO 92/19734 | 11/1992 |
| WO | 93/12141 | 6/1993 |
| WO | WO 96/02645 | 2/1996 |
| WO | WO 96/11212 | 4/1996 |
| WO | 96/27610 | 9/1996 |
| WO | 97/01571 | 1/1997 |
| WO | WO 9719172 | 5/1997 |

OTHER PUBLICATIONS

Steadman's Medical Dictionary, 25th edition, Williams & Wilkins, p. 434.*
Jeffrey S. Nye et al., "Vertebrate Ligands for Notch," *Current Biology*, V. 5, 1995, pp. 966-969.
Kriegler MP (1990) *Gene Transfer and Expression; A Laboratory Manual* (not available).
S. Artavanis-Tsakonas et al., "Notch Signaling," *Science*, vol. 268, Apr. 14, 1995, pp. 225-232.
J. Wagner et al., "Isolation of Small, Primitive Human Hematopoietic Stem Cells: Distribution of Cell Surface Cytokine Receptors and Growth in SCID-HU Mice," *Blood*, vol. 86, No. 2 (Jul. 15), 1995, pp. 512-523.

L. Ellisen et al., "TAN-1, the Human Homolog of the *Drosophila* Notch Gene, Is Broken By Chromosomal Translocations in T Lymphoblastic Neoplasms," *Cell*, vol. 66, Aug. 23, 1991, pp. 649-661.
L. Milner et al., "A Human Homologue of the *Drosphila* Developmental gene, *Notch*, is Expressed In CD34+ Hematopoietic Precursors," *Blood*, vol. 83, No. 8 (Apr. 15), 1994, pp. 2057-2062.
R. Fehon et al., "Molecular Interactions between the Protein Products of the Neurogenic Loci *Notch* and *Delta*, Two EGF-Homologous Genes in *Drosophila*," *Cell*, vol. 61, May 4, 1990, pp. 523-534.
I. Rebay et al., "Specific EGF Repeats of *Notch* Mediate Interactions with *Delta* and Serrate: Implications for *Notch* as a Multifunctional Receptor," *Cell*, vol. 67, Nov. 15, 1991, pp. 687-699.
R. Jackman et al., "Characterization of a thrombomodulin cDNA reveals structural similarity to the low density lipoprotein receptor," *Proc. Natl. Acad. Sci. USA*, vol. 83 Dec. 1986, pp. 8834-8838.
D. Russell et al., "Domain Map of the LDL Receptor: Sequence Homology with the Epidermal Growth Factor Precursor," *Cell*, Jun. 1984, pp. 577-585.
B. Furie et al., "The Molecular basis of Blood Coagulation," *Cell*, vol. 53, May 20, 1988, pp. 505-518.
D. Henrique et al., "Expression of a *Delta* homologue in prospective neurons in the chick," *Nature*, vol. 375, Jun. 29, 1995, pp. 787-790.
A. Chitnis et al., "Primary neurogenesis in Xenopus embryos regulated by a homologue of the *Drosophila* neurogenic gene *Delta*," *Nature*, vol. 375, Jun. 29, 1995, pp. 761-766.
C. Lindsell et al., "Jagged: A Mammalian Ligand That Activates Nothc1," *Cell*, vol. 80, Mar. 24, 1995, pp. 909-917.
J. Sambrook et al., *Molecular Cloning; a laboratory manual*, Second Edition, Cold Spring Harbor Laboratory Press, New York, 1989.
Kyte et al., "A Simple Method for Displaying the Hydropathic Character of a Protein," *J. Mol. Biol.* (1982) 157, pp. 105-132.
M. Frohman et al., "Rapid production of full-length cDNAs fromrare transcripts: Amplification using a single gene-specific oligonucleotide primer," *Proc. Natl. Acad. Sci. USA*, vol. 85, Dec. 1988, pp. 8998-9002.
L. Enquist et al., "*In Vitro* Packaging of λ Dam Vectors and Their Use in Cloning DNA Fragments," *Methods in Enzymology*, vol. 68, pp. 281-299.
T. Yokota et al., editors, "Introduction and expression of gene and its analysis method," *Experimental medicine*.
E. Harlow et al., *Antibodies; A Laboratory Manual*, Cold Spring Harbor Laboratory, 1988, New York.
C. Verfaillie et al., "Macrophage Inflammatory Protein 1a, Interleukin 3 and Diffusible Marrow Stromal Factors Maintain Human hematopoietic Stem Cells for at least Eight Weeks *In Vitro*," *J. Exp. Med.*, vol. 179, Feb. 1994, pp. 643-649.
K. Yoshizato, "Stem cell which is continuing division with self-replication activity".

(Continued)

*Primary Examiner*—Prema Mertz
(74) *Attorney, Agent, or Firm*—Young & Thompson

(57) ABSTRACT

A method for suppressing differentiation of undifferentiated blood cells in vivo by contacting the cells in vitro with a serrate-1 peptide, thereby suppressing differentiation of the cells.

7 Claims, 5 Drawing Sheets

OTHER PUBLICATIONS

G. Zettlmeissl et al., "Expression and Characterization of Human CD4: Immunoglobulin Fusion Proteins," *DNA and Cell Biology,* vol. 9, No. 5, 1990, pp. 347-353.

E. Kabat et al., *Sequences of Proteins of Immunological Interest,* Fifth Edition, N1H Publication No. 91-3242, 1991, selected pages.

H. Sutherland et al., "Characterization and Partial Purification of Human Marrow Cells Capable of Initiating Long-Term Hematopoiesis *In Vitro,*" *Blood,* vol. 74, No. 5, Oct. 1989, pp. 1563-1570.

H. Sutherland et al., "Functional characterization of individual human hematopoietic stem cells cultured at limiting dilution on supportive marrow stromal layers," *Proc. Natl. Acad. Sci. USA,* vol. 87, May 1990, pp. 3584-3588.

C. Taswell, "Limiting Dilution Assays for the Determination of Immunocompetent Cell Frequencies," *The Journal of Immunology,* vol. 126, No. 4, Apr. 1981, pp. 1614-1619.

Freshney (Culture of Animal Cells, A Manual of Basic Technique, Alan R. Liss, Inc., New York, p. 4).

Dermer (Bio/Technology, 12:320).

Bowie et al (Science, 257:1306-1310).

Burgess et al (J. Cell Bio., 111:2129-2138).

Lazar et al (Mol. Cell. Bio., 8:1247-1252).

Tax et al (Nature, 368:250-254).

Milner et al (Blood, 83:2057-2062).

Ratajczak et al (Mater. Med. Pol., 25:133-136).

* cited by examiner

FIG. 1

```
Cosensus    :C*YY*C*CRPRDD*FGHC*G*C*GW*G**C*
hDelta-1.DSL:FVCDEHYYGEGCSVFCRPRDDAFGHFTCGERGEKVCNPGWKGPYC
dDelta.DSL  :VTCDLNYYGSGCAKFCRPRDDSFGHSTCSETGEIICLTGWQGDYC
xDelta.DSL  :FVCDEYYYGEGCSDYCRPRDDAFGHFSCGERGEKLCNPGWKGLYC
cDelta-1.DSL:FVCDEHYYGEGCSVFCRPRDDRFGHFTCGERGEKVCNPGWKGQYC
mDelta-1.DSL:FVCDEHYYGEGCSVFCRPRDDAFGHFTCGDRGEKMCDPGWKGQYC
hSerrate-1.DSL:VTCDDYYYGFGCNKFCRPRDDFFGHYACDQNGNKTCMEGWMGPEC
dSerrate.DSL:VQCAVTYYNTTCTTFCRPRDDQFGHYACGSEGQKLCLNGWQGVNC
rJagged.DSL :VTCDDHYYGFGCNKFCRPRDDFFGHYACDQNGNKTCMEGWMGPEC
              *  ***     ***   ******  **    *       **  *
```

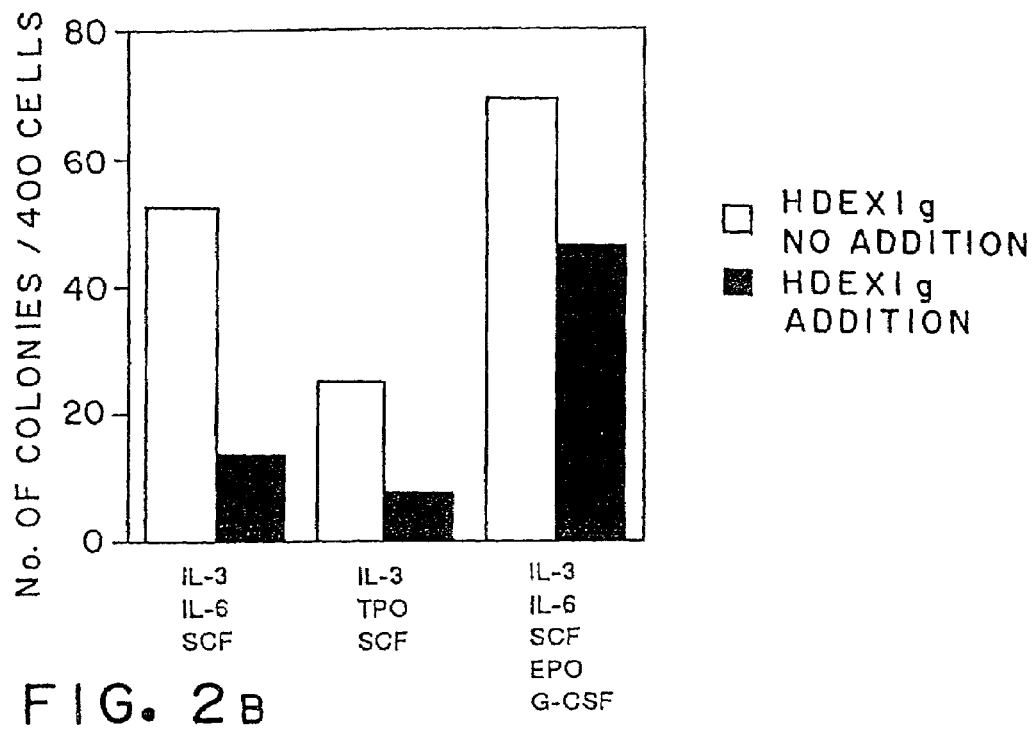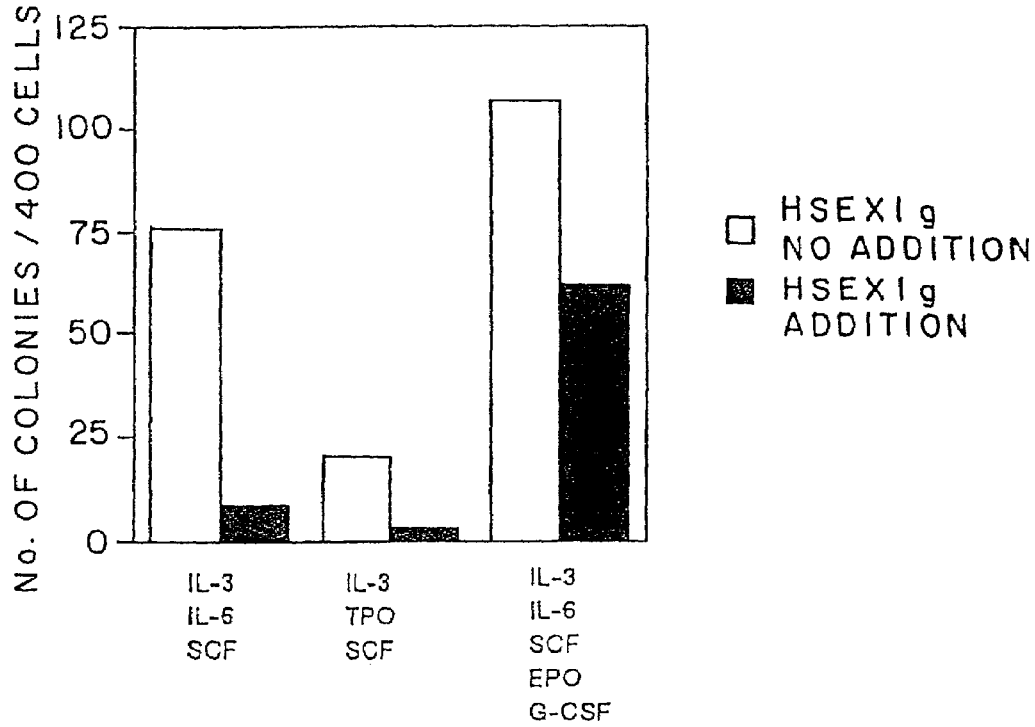

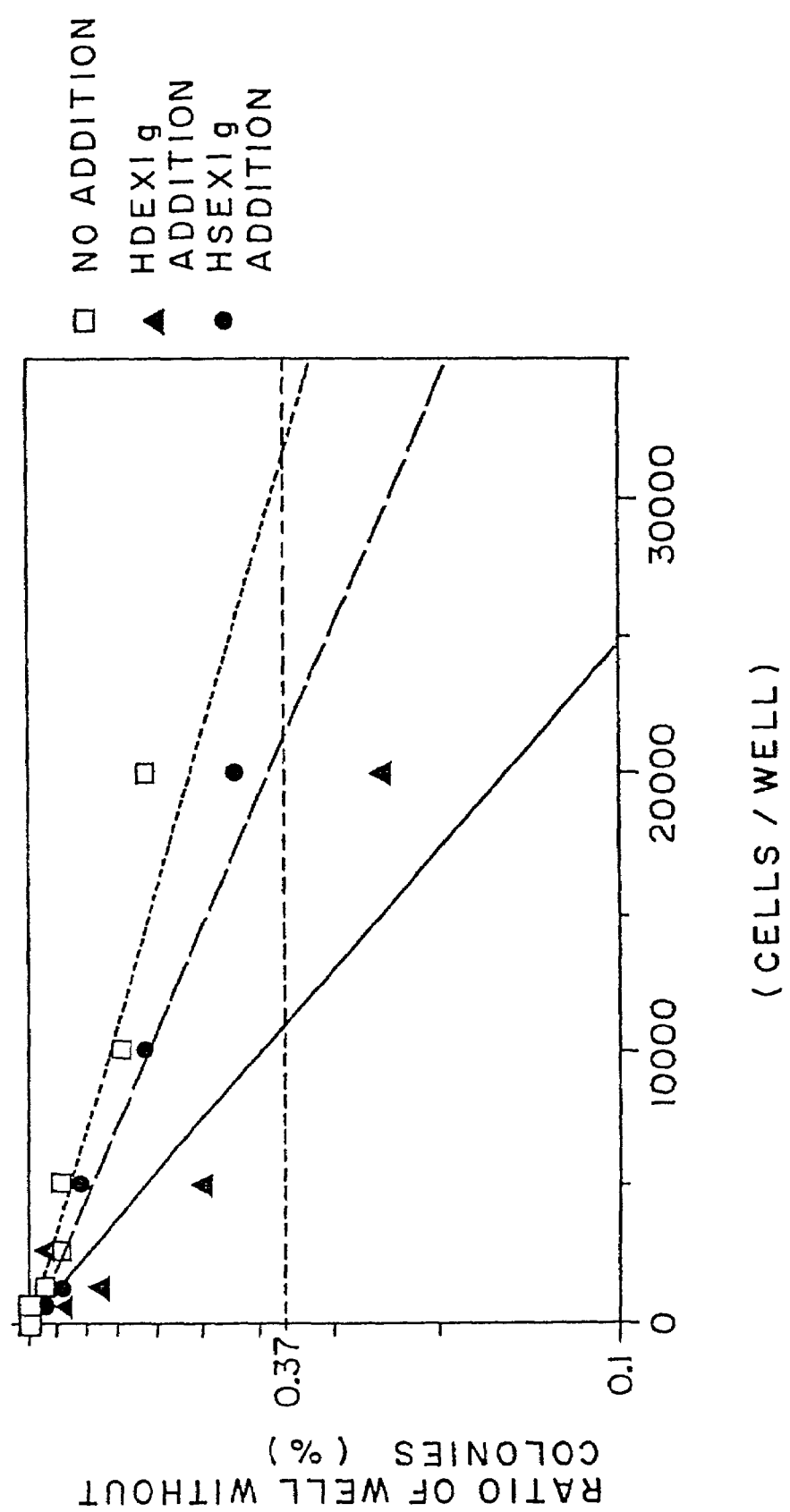

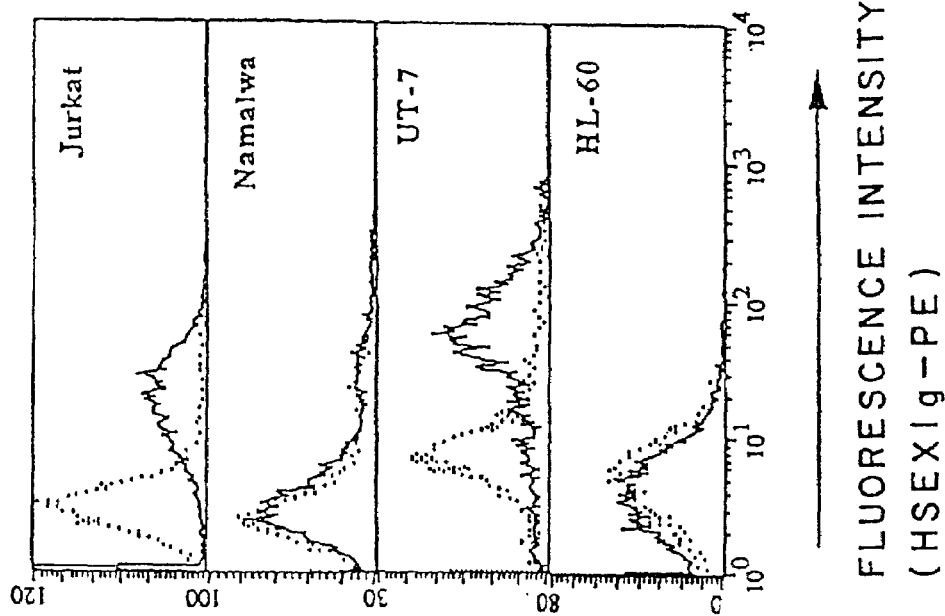
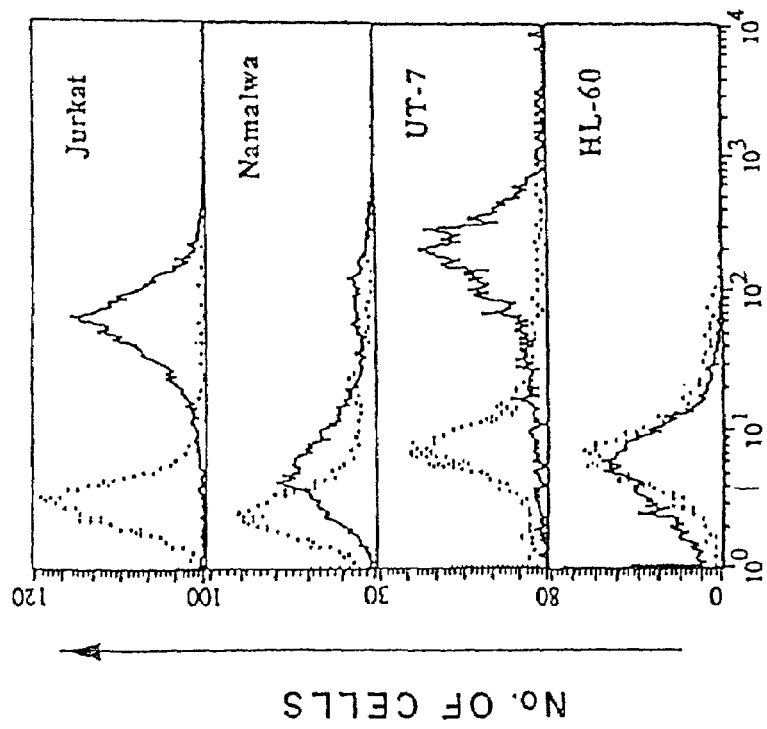

METHOD OF SUPPRESSING DIFFERENTIATION BY ADMINISTERING A HUMAN SERRATE-1 POLYPEPTIDE

BACKGROUND OF THE INVENTION

This invention relates to a novel bioactive substance which suppresses differentiation of undifferentiated cells.

DESCRIPTION OF THE RELATED ART

Human blood and lymph contain various types of cells and each cell plays important roles. For example, the erythrocyte carries oxygen; platelets have hemostatic action; and lymphocytes prevent infection. These various cells originate from hematopoietic stem cells in the bone marrow. Recently, it has been clarified that the hematopoietic stem cells are differentiated to various blood cells Osteoclasts and mast cells by stimulation of various cytokines in vivo and environmental factors. In the cytokines, there have been found, for example, erythropoietin (EPO) for differentiation to erythrocytes; granulocyte colony stimulating factor (G-CSF) for differentiation to leukocytes; and platelet growth factor (mpl ligand) for differentiation to megakaryocytes which are platelet producing cells, and the former two have already been clinically applied.

The undifferentiated blood cells are generally classified into two groups consisting of blood precursor cells which are destined to differentiate to specific blood series and hematopoietic stem cells which have differentiation ability to all series and self-replication activity. The blood precursor cells can be identified by various colony assays. However, identification method for the hematopoietic stem cells have not been established. In these cells, stem cell factor (SCF), interleukin-3 (IL-3), granulocyte-macrophage colony stimulating factor (GM-CSF), interleukin-6 (IL-6), interleukin-1 (IL-1) granulocyte colony stimulating factor (G-CSF) and oncostatin M have been reported to stimulate cell differentiation and proliferation. Trials for expansion of hematopoietic stem cells in vitro have been examined in order to replace bone marrow transplantation for applying hematopoietic stem cell transplantation therapy or gene therapy. However, when the hematopoietic stem cells are cultured in the presence of the above mentioned cytokines, multi-differentiation activities and self-replication activities, which are originally in the position of the hematopoietic stem cells, gradually disappeared and are changed to the blood cell precursors which are only to differentiate to specific series after 5 weeks of cultivation, and multi-differentiation activity which is one of the specific features of the hematopoietic stem cells, is lost (Wagner et al., Blood 86. 512–523, 1995).

For proliferation of the blood precursor cells, a single cytokine is not sufficient, but the synergistic action of several cytokines are important. Consequently, in order to proliferate the hematopoietic stem cells while maintaining specific features of the hematopoietic stem cells, it is necessary to add cytokines which suppress differentiation together with the cytokines which proliferate and differentiate the undifferentiated blood cells. In general, may cytokines which stimulate proliferation or differentiation of cells are known, but small numbers of cytokines which suppressed cell differentiation are known. For example, leukemia inhibitory factor (LIF) has an action of proliferation of mouse embryonic stem cells without differentiation, but it has no action against the hematopoietic stem cells or blood precursor cells. Transforming growth factor (TGF-β) has suppressive action for proliferation against various cells, but no fixed actions against the hematopoietic stem cells or blood precursor cells.

Not only blood cells but also undifferentiated cells, especially stem cells, are thought to be involved in tissue regeneration. These regeneration of tissues and proliferation of undifferentiated cells in each tissue can be applied in various ways by referring to the known reference (Katsutoshi Yoshizato, Regeneration—a mechanism of regeneration, 1996, Yodosha Publ. Co.).

Notch is a receptor type membrane protein which is involved in regulation of nerve cells differentiation found in *Drosophia*. Homologues of the Notch are found in various animal kinds exceeding to the invertebrate and vertebrate including nematoda (Lin-12). *Xenopus laevis* (Xotch), mouse (Motch) or human (TAN-2). Ligand of the Notch in *Drosophila* are known. These are *Drosophila* Delta (Delta) and *Drosophila* Serrate (Serrate). Notch ligand homologues are found in various animal kinds as similar to the Notch of receptors (Artavanis-Tsakonas et al., Science 268, 225–232, 1995).

Human Notch homologue, TAN-1 is found widely in the tissues in vivo (Ellisen et al., Cell 66. 649–661, 1991). Two Notch analogous molecules other than TAN-1 are reported (Artavanis-Tsakonas et al., Science 268, 225–232, 1995). Expression of TAN-1 was also observed in CD34 positive cells in blood cells by PCR (Polymerase Chain Reaction) (Milner et al., Blood 83, 2057–2062, 1994). However, in relation to humans, gene cloning of human Delta and human Serrate, which are thought to be the Notch ligand, have not been reported.

In *Drosophila* Notch, binding with the ligand was studied and investigated in detail, and it was found that the Notch can be bound to the ligand with Ca** at the binding region, which is a repeated amino acid sequence No. 11 and No. 12 in the amino acid sequence repeat of Epidemal Growth Factor (EGF) like repeating (Fehon et al., Cell 61. 523–534, 1990, Rebay et al., ibid. 67, 687–699, 1991 and Japan. Patent PCT Unexam. Publ. 7-503123). EGF-like repeated sequences are conserved in Notch homologues of the other species. Consequently, the same mechanism in binding with ligand is estimated. An amino acid sequence which is called DSL (Delta-Serrate-Lag-2) near the amino acid terminal, and EGF-like repeated sequence as in the receptor are conserved in the ligand (Artavanis-Tsakonas et al.), Science 268, 225–232, 1995).

The sequence of DSL domain is not found except for the Notch ligand molecules, and is specific to Notch ligand molecule. A common sequence of DSL domain is shown in the sequence listing, SEQ ID NO: 1 in general formula, and comparison with human Delta-1 and human Serrate-1 of the present invention and known Notch ligand molecules are shown in FIG. 1.

EGF-like sequence has been found in thrombomodulin (Jackman et al., Proc. Natl. Acad. Sci. USA 83, 8834–8838, 1986), low density lipoprotein (LDL) receptor (Russell et al., Cell 37, 577–585, 1984), and blood coagulating factor (Furie et al., Cell 53, 505–518, 1988), and is thought to play important roles in extracellular coagulation and adhesion.

Recently, the vertebrate homologues of the cloned *Drosophila* Delta were found in chicken (C-Delta-1) and *Xenopus laevis* (X-Delta-1), and it was reported that X-Delta-1 had acted through Notch in the generation of the protoneuron (Henrique et al., Nature 375, 787–790, 1995 and Chitnis et al., ibid. 375, 761–766, 1995). Vertebrate homologue of *Drosophila* Serrate was found in rat as rat Jagged (Jagged) (Lindsell et al., Cell 80, 909–917, 1995). According to the Lindsell et al., mRNA of the rat Jagged is detected in the spinal cord of fetal rats. As a result of cocultivation of a myoblast cell line is found. However, the rat Jagged has no action against the myoblast cell line without forced expression of the rat Notch.

Considering the above reports, the Notch and ligand thereof may be involved in the differentiation regulation of the nerve cells, however, except for some myoblast cells, their actions against cells including blood cells, especially primary cells, are unknown.

In the Notch ligand molecule, from the viewpoint of the prior studies on *Drosophila* and *nematodae*, the Notch ligand has specifically a structure of DSL domain which is not found other than in the Notch ligand. Consequently, the fact of having DSL domain means equivalent to ligand molecule for the Notch receptor.

SUMMARY AND OBJECTS OF THE INVENTION

As mentioned above, concerning undifferentiated cells, proliferation that maintains their specificies has not been achieved. Major reasons are that factors suppressing differentiation of the undifferentiated cells are not sufficiently known. An object of the present invention is to provide a compound originated from novel factors which can suppress differentiation of the undifferentiated cells.

We have set up a hypothesis that the Notch and its ligand have action of differential regulation not only for neuroblasts and myoblasts but also for various undifferentiated cells, especially blood undifferentiated cells. However, in case of clinical application in the humans, prior known different species such as chicken or *Xenopus laevos* type notch ligand have problems of species specificities and antigenicities. Consequently, to obtain previously unknown human Notch ligand is essentially required. We had an idea that a molecule having DSL domain and EGF-like domain which are common to Notch ligand molecules and a ligand of the human Notch (TAN-1 etc.), which is a human Delta Homologue hereinafter designated as human Delta) and human Serrate homologue (hereinafter designated as human Serrate), may be found. Also we have an idea that these findings may be a candidate for drugs useful for differential regulation of the undifferentiated cells, and we have tried to find out the same.

In order to find out human Notch ligands, we have analyzed amino acid sequences which are conserved in animals other than humans, and tried to find out genes by PCR using mixed primers of the corresponding DNA sequence. As a result of extensive studies, we have succeeded in isolation of cDNAs coding amino acid sequences of two new molecules, novel human Delta-1 and novel human Serrate-1, and have prepared the expression systems of protein having various forms using these cDNAs. Also we have established purification method of the proteins which were purified and isolated.

Amino acid sequences of novel human Delta-1 are shown in the sequence listings, SEQ ID NO: 2–4. DNA sequence coding these sequence is shown in the sequence listing, SEQ ID NO: 8. Amino acid sequence of novel human Serrate-1 is shown in the sequence listings, SEQ ID NO: 5–7. DNA sequence coding these sequence is shown in the sequence listing. SEQ ID NO: 10.

Physiological actions of the these prepared proteins were searched by using nerve undifferentiated cells, preadipocytes, hepatocytes, myoblasts, skin undifferentiated cells, blood undifferentiated cells and immuno undifferentiated cells. As a result, we have found that novel human Delta-1 and novel human Serrate-1 had an action of differentiation-suppressive action to primary blood undifferentiated cells, and had a physiological action to maintain undifferentiated state.

Such actions to the blood undifferentiated cells have never been reported previously, and is a new discovery. No significant toxic actions were noted in the toxicity studies on mice, and useful pharmaceutical effects were suggested. Consequently, the pharmaceutical preparations containing the molecule of the present invention, medium containing the molecule of the present invention, and the device having immobilized thereon the molecule of the present invention are novel drugs and medical materials which can maintain the blood undifferentiated cells in the undifferentiated conditions. Antibodies against human Delta-1 and human Serrate-1 are prepared by using antigens of the said human Delta-1 and human Serrate-1, and purification method of the said antibodies are established. The present invention has been completed accordingly.

The present invention further related relates to a polypeptide comprising amino acid sequence of SEQ ID NO: 1 of the sequence listing encoded in a gene of human origin, a polypeptide comprising at least amino acid sequence of SEQ ID NO: 2 or NO: 5 of the sequence listing, the polypeptide comprising amino acid sequence of SEQ ID NO: 3 of the sequence listing, the polypeptide comprising amino acid sequence of SEQ ID NO: 4 of the sequence listing, the polypeptide comprising amino acid sequence of SEQ ID NO: 6 of the sequence listing, the polypeptide comprising amino acid sequence of SEQ ID NO: 7 of the sequence listing, the polypeptide having differentiation suppressive action against undifferentiated cells, the polypeptide in which undifferentiated cells are undifferentiated cells other than those of the brain and nervous system or muscular system cells, and the polypeptide in which undifferentiated cells are the undifferentiated blood cells. The present invention also relates to a pharmaceutical composition containing the polypeptides, and the pharmaceutical composition in which use there is as a hematopoietic activator. The present invention further relates to a cell culture medium containing the polypeptides, and the cell culture medium in which the cell is the undifferentiated blood cell. The present invention still further relates to a DNA coding a polypeptide at least having amino acid sequence of SEQ ID NO: 2 or NO: 5 of the sequence listing, the DNA having DNA sequence 242–841 of SEQ ID NO: 8 or DNA sequence 502–1095 of SEQ ID NO: 10 of the sequence listing, the DNA coding the polypeptide having amino acid sequence of SEQ ID NO: 3 of the sequence listing, the DNA coding the polypeptide having amino acid sequence of SEQ ID NO: 4 of the sequence listing, the DNA having DNA sequence 242–2347 of the SEQ ID NO: 8 of the sequence listing, the DNA coding the polypeptide having amino acid sequence of SEQ ID NO: 6 of the sequence listing, the DNA having DNA sequence 502–3609 of SEQ ID NO: 10 of the sequence listing, the DNA coding the polypeptide having amino acid sequence of SEQ ID NO: 7 of the sequence listing, and the DNA having DNA sequence 502–4062 of SEQ ID NO: 10 of the sequence listing. The present invention still further relates to a recombinant DNA made by ligating a DNA selected from the groups of DNA hereinabove and a vector DNA which can express in the host cell, a cell transformed by the recombinant DNA, and a process for production of polypeptide by culturing cells and isolating the thus produced compound. The present invention still further relates to an antibody specifically recognizing the polypeptide having the amino acid sequence of SEQ ID NO: 7 of the sequence listing.

DETAILED DESCRIPTION OF THE PREFERRED EMBODIMENTS

The present invention is explained in details in the following:

Preparation of cDNA necessary for gene manipulation, expression analysis by Northern blotting, screening by hybridization, preparation of recombinant DNA, determination of DNA base sequence and preparation of cDNA library, all of which are series of molecular biological experiments, can be performed according to a description of the conventional textbook for the experiments. The above conventional textbook of the experiments is, for example, Maniatis et al. ed. Molecular Cloning, A laboratory manual, 1989, Eds., Sambrook, J., Fritsch, E. F. and Maniatis, T., Cold Spring Harbor Laboratory Press.

A polypeptide of the present invention has at least one of the polypeptides in the sequence listing SEQ ID NO: 1–7. A mutant and allele which naturally occur in the nature are included in the polypeptide of the present invention unless the polypeptides of the sequence listing, SEQ ID NO: 1–7 lose their properties. Modification and substitution of amino acids are described in details in the patent application by the name of Benntt et al. (National Unexam. Publ. WO96/2645) and can be prepared according to the description thereof.

A DNA sequence coding polypeptides of the sequence listing, SEQ ID NO: 2–4 is shown in the sequence listing, SEQ ID NO: 8, and a DNA sequence coding polypeptides of the sequence listing, SEQ ID NO: 5–7 is show in the sequence listing, SEQ ID NO: 10, together with their amino acid sequences. In these DNA sequences, even if amino acid level mutation is not generated, naturally isolated chromosomal DNA or cDNA thereof may have a possibility to mutate in the DNA base sequence as a result of degeneracy of genetic code without changing amino acid sequence coded by the DNA. A 5'-untranslated region and 3'-untranslated region are not involved in amino acid sequence determination of the polypeptide, so DNA sequences of these regions are easily mutated. The base sequence obtained by these degeneracies of genetic codes is included in the DNA of the present invention.

Undifferentiated cells in the present invention are defined as cells which can grow by specific stimulation, and cells which can be differentiated to the cells having specific functions as a result of the specific stimulations. These include undifferentiated cells of the skin tissues, undifferentiated cells of the brain and nervous systems, undifferentiated cells of the muscular systems and undifferentiated cells of the blood cells. These cells include the cells of self-replication activity which are called stem cells, and the cells having an ability to generate the cells of these lines. The differentiation-suppressive action means suppressive action for autonomous or heteronomous differentiation of the undifferentiated cells, and is an action for maintaining undifferentiated condition. The brain and nervous undifferentiated cells can be defined as cells having ability to differentiate to the cells of the brain or nerve having specific functions by specific stimulation. The undifferentiated cells of the muscular systems can be defined as cells having ability to differentiate to the muscular cells having specific functions by specific stimulation. The blood undifferentiated cells in the present invention can be defined as cell groups consisting of the blood precursor cells which are differentiated to the specific blood series identified by blood colony assay, and hematopoietic stem cells having differentiation to every series and self-replication activities.

In the sequence listing, amino acid sequence in SEQ ID NO: 1 shows general formula of common amino acid sequence of DSL domain which is a common domain structure of the Notch ligand molecules, and at least this domain structure corresponds to the sequence listing, AMINO ACIDS 158–200 of the human Delta-1, or the sequence listing AMINO ACIDS 156–198 of the human Serrate-1.

The amino acid sequence in the sequence listing, SEQ ID NO: 2 is a sequence of the active center of the present invention of human Delta-1 minus the signal peptide, i.e. amino acid sequence from the amino terminal to DSL domain, and corresponds to an amino acid No. 1 to 200 in SEQ ID NO: 4 of the mature full length amino acid sequence of human Delta-1 of the present invention. The amino acid sequence in SEQ ID NO: 3 is amino acid sequence of extracellular domain of the present invention of human Delta-1 minus the signal peptide, and corresponds to an amino acid No. 1 to 520 in SEQ ID NO: 4 of the mature full length amino acid sequence of human Delta-1 of the present invention. The amino acid sequence of SEQ ID NO: 4 is the mature full length amino acid sequence of the human Delta-1 of the present invention.

The amino acid sequence in the sequence listing, SEQ ID NO: 5 is a sequence of the active center of the present invention of human Serrate-1 minus the signal peptide, i.e. amino acid sequence from the amino terminal to DSL domain, and corresponds to an amino acid No. 1 to 198 in SEQ ID NO: 7 of the mature full length amino acid sequence of human Serrate-1 of the present invention. The amino acid sequence in SEQ ID NO: 6 is amino acid sequence of extracellular domain of the present invention of human Serrate-1 minus the signal peptide, and corresponds to an amino acid No. 1 to 1036 in SEQ ID NO: 7 of the mature full length amino acid sequence of human Serrate-1 of the present invention. The amino acid sequence of SEQ ID NO: 7 is the mature full length amino acid sequence of the human Serrate-1 of the present invention.

The sequence of SEQ ID NO: 8 is the total amino acid sequence of human Delta-1 of the present invention and cDNA coding the same, and the sequence of SEQ ID NO: 10 is total amino acid sequence of human Serrate-1 of the present invention and cDNA coding the same.

The left and right ends of the amino acid sequences in the sequence listing indicate amino terminal (hereinafter designated as N-terminal) and carboxyl terminal (hereinafter designated as C-terminal), respectively, and the left and right ends of the nucleotide sequences are 5'-terminal and 3'-terminal, respectively.

Cloning of human Notch ligand gene can be performed by the following method. During the evolution of the organisms, a part of amino acids sequences of the human Notch ligand is conserved. DNA sequence corresponding to the conserved amino acid sequence is designed, and is used as a primer of RT-PCR (Reverse Transcription Polymerase Chain reaction), then a PCR template of the human origin is amplified by PCR reaction, thereby fragments of human Notch ligand can be obtainable. Furthermore, RT-PCR primer is prepared by applying the known DNA sequence information of the Notch ligand homologue of the organisms other than humans, and the known gene fragments can be possibly obtained from PCR template of the said organisms.

In order to perform PCR for obtaining fragments of human Notch ligand, PCR for DSL sequence is considered, but a large number of combinations of DNA sequence corresponding to amino acid sequence conserved in this region can be expected, and a design for PCR is difficult. As a result, PCR of the EGF-like sequence has to be selected. As explained hereinbefore, since EFG-like sequence is conserved in a large number of molecules, to obtain the fragments and identification are extremely difficult.

We have designed and prepared about 50 PCR primer sets, for example, the primer set of the sequence shown in Example 1, PCR was performed with these primer sets by using PCR template of cDNA prepared from poly A+ RNA of various tissues of human origin, and more than 10 PCR products from each tissue were subcloned, as well as performing sequencing for more than 500 types. A clone having a desired sequence could be identified. Namely, the obtained PCR product is cloned in the cloning vector, transforming the host cells by using recombinant plasmid which contains the PCR product, culturing the host cells containing the recombinant plasmid on a large scale, purifying and isolating the recombinant-plasmid, checking the DNA sequence of PCR product which is inserted into the cloning vector, and trying to obtain the gene fragment which may have a sequence of human Delta-1 by comparing with the sequence of the known Delta of other species. We have succeeded to find out the gene fragment which contains a part of cDNA of human Delta-1, the same sequence of DNA sequence from 1012 to 1375 described in the sequence listing, SEQ ID NO: 8.

We have also designed and prepared about 50 PCR primer sets, for example, the primer set of the sequence shown in Example 3, and PCR was performed with these primer sets by using PCR template of cDNA prepared from poly A+ RNA of various tissues of human origin, and more than 10 PCR products from each tissue were subcloned, as well as performing sequencing for more that 500 types. A clone having a desired sequence could be identified. Namely, the obtained PCR product is cloned in the cloning vector, transforming the host cells by using recombinant plasmid which contains the PCR product, culturing the host cells containing the recombinant plasmid on a large scale, purifying and isolating the recombinant plasmic, checking the DNA sequence of PCR product which is inserted into the cloning vector, and trying to obtain the gene fragment which may have a sequence of human Serrate-1 by comparing with the sequence of the known Serrate of other species. We have succeeded to find out the gene fragment which contains a part of cDNA of human Serrate-1, the same sequence of DNA sequence from 1272 to 1737 described in the sequence listing, SEQ ID NO: 10.

A full length of the objective gene can be obtained form the human genomic gene library or cDNA library by using the thus obtained human Delta-1 fragment or human Serrate-1 gene fragment. The full length cloning can be made by isotope labeling and non-isotope labeling with the partial cloning gene, and screening the library by hybridization or other method. Isotope labeling can be performed by, for example, terminal labeling by using [$^{32}$p] γ-ATP and T4 polynucleotide kinase, or other labeling methods such as nick translation or primer extension method can be applied. In another method, human originated cDNA library is ligated into the expression vector, expressing by COS-7 or other cells, and screening the objective gene by expression cloning to isolate cDNA of the ligand. In the expression cloning, a cell sorter fractionation method which is applied with binding with polypeptide containing amino acid sequence of prior known 4 Notches such as TAN-1, and a detection method by film emulsion using radioisotope can be mentioned. In this specification, methods for obtaining genes of human Delta-1 and human Serrate-1 are explained, and in addition to that obtaining the Notch ligand homologue gene of the other organism is important for analysis of ligand action. This may be made by the same treatment. The obtained gene is subjected to DNA sequence determination and amino acid sequence can be estimated.

As shown in Example 2, gene fragments containing human Delta-1 PCR product are labeled with radioisotope to prepare hybridization probe screening is performed using cDNA of human placenta origin as the screening library. DNA sequences of the thus obtained clones are determined, and the clone is obtained containing DNA nucleotide sequence shown in the sequence listing. SEQ ID NO: 8, and shown to have the amino acid sequence coded in the sequence listing. SEQ ID NO: 4. We have succeeded in cloning cDNA coding full length of amino acids sequence of human Delta-1.

These sequences were compared with the data base (Genbank release 89, June, 1995), and found that these were novel sequences. The said amino acid sequence was analyzed in hydrophilic part and hydrophobic part according to a method by Kyte-Doolittle (J. Mol. Biol. 157: 105, 1982). A result indicated that human Delta-1 of the present invention is expressed on cells as a cellular membrane protein having a transmembrane domain.

As shown in Example 4, gene fragments containing human Serrate-1 PCR product are labeled with radioisotope to prepare hybridization probe, screening is performed using cDNA of human placenta origin as the screening library, DNA sequences of the thus obtained clones are determined and the clone is obtained containing DNA nucleotide sequence shown in the sequence listing, SEQ ID NO: 10, and shown to have the amino acid sequence coded in the sequence listing, SEQ ID NO: 7. In this screening, an intracellular part of gene sequence coding a full length of amino acids sequence, namely a peripheral part of termination codon cannot be cloned. Consequently, as shown in Example 4, gene cloning is performed by RACE method (rapid amplification of cDNA ends, Frohman et al., Proc. Natl. Acad. Sci. U.S.A. 85, 8998–9002, 1988) and finally succeeded in cloning of cDNA coding fill length of amino acid sequence of human Serrate-1.

These sequences were compared with the data base (Genbank release 89, June, 1995, and found that these were novel sequences. The said amino acid sequence was analyzed in hydrophilic part and hydrophobic part according to a method by Kyte-Doolittle (J. Mol. Biol. 157: 105, 1982). A result indicated that human Serrate-1 of the present invention is expressed on cells as a cellular membrane protein having a transmembrane domain.

Examples of plasmids integrated with cDNA are, for example, E. coli originated pBR322, pUC18, pUC19, pUC118 and pUC119 (Takara Shuzo Co., Japan), but other plasmids can be used if they can replicate and proliferate in the host cells. Examples of phage vectors integrated with cDNA are, for example, λgt10 and λgt11, but other vectors can be used if they can grow in the host cells. The thus obtained plasmids are transducted into suitable host cells such as genus *Escherichia* and genus *Bacillus* using calcium chloride method. Examples of the above genus *E scherichia* are *Eseherichia coli* K12HB101, MC1061, LE392 and HM109. Example of the above genus *Bacillus* is *Bacillus subtilis* MI114. Phage vector can be introduced into the proliferated *E. coli* by the in vitro packaging method (Enquist and Sternberg, Meth. Enzymol., 68, 281-, 1979).

According to the analysis of amino acid sequence of the human Delta-1, amino acid sequence of a precursor of human Delta-1 consists of 723 amino acids residue shown in the sequence listing, SEQ ID NO: 8, and the signal peptide domain is estimated to correspond to an amino acid sequence of 21 amino acids residue from No. −21 methionine to No. −1 serine of the sequence listing; extracellular domain: 520 amino acids residue from No. 521 proline to No. 552 leucine; and intracellular domain: 150 amino acids region from No. 553 glutamine to No. 702 valine. These domains are estimated domain construction from amino acid sequences, and actual presence form may differ from the above structure, and constitutional amino acids of each domain hereinabove defined may have possibility to change 5 to 10 amino acids sequence.

According to a comparison in amino acid sequence of human Delta-1 and Delta homologue of the other organisms, the homologies with *Drosophila* Delta, chick Delta and *Xenopus laevis* are 47.6%, 83.3% and 76.2%, respectively. The human Delta-1 of the present invention is different from these Deltas and is novel substance which is clarified at first by the present inventors. Search from all of organisms in the above data base indicated that polypeptides having the identical sequence of the human Delta-1 could not be found.

The homologues of Notch ligand have evolutionally conserved common sequence, i.e. repeated DSL sequence and EGF-like sequence. As a result of comparison with amino acid sequence of human Delta-1, these conserved sequence is estimated. Namely, DSL sequence corresponds to 43 amino acids residue from No. 158 cysteine to No. 200 cysteine of the amino acid sequence in the sequence listing, SEQ ID NO: 4. EGF-like sequence exists with 8 repeats wherein, in the amino acid sequence in the sequence listing SEQ ID NO: 4, the first EGF-like sequence from No. 205 cysteine to No. 233 cysteine; the second EGF-like sequence from No. 236 cysteine to No. 264 cysteine; the third EGF-like sequence from No. 271 cysteine to No. 304 cysteine; the fourth EGF-like sequence from No. 311 cysteine to No. 342 cysteine; the fifth EGF-like sequence from No. 349 cysteine to No. 381 cysteine; the sixth EGF-like sequence from No. 388 cysteine to No. 419 cysteine; the seventh EGF-like sequence from No. 426 cysteine to No. 457 cysteine; and the eighth EGF-like sequence from No. 464 cysteine to No. 495 cysteine.

A part of sugar chain attached is estimated from amino acid sequence of the human Delta-1 may be No. 456 asparagine residue in the sequence listing, SEQ ID NO: 4 as a possible binding site of N-glycoside bonding for N-acetyl-D-glucosamine. O-glycoside bond of N-acetyl-D-galactosamine is estimated to be a serine or threonine residue rich part. Protein bound with sugar chain is generally thought to be stable in vivo and to have strong physiological activity. Consequently, in the amino acid sequence of polypeptide having sequence of the sequence listing, SEQ ID NO: 2, 3 or 4, polypeptides having N-glucoside or O-glucoside bond with sugar chain of N-acetyl-D-glucosamine or N-acetyl-D-galactosamine is included in the present invention.

According to the analysis of amino acid sequence of the human Serrate-1, amino acid sequence of a precursor of human Serrate-1 consists of 1218 amino acids residue shown in the sequence listing, SEQ ID NO: 10, and the signal peptide domain is estimated to correspond 31 amino acids residue in the amino acid sequence from No. −31 methionine to No. −1 alanine of the sequence listing; extracellular domain: 10366 amino acids residue from No. 1 serine to No. 1036 asparagine; transmembrane domain: 26 amino acids residue from No. 1037 phenylalanine to No. 1062 leucine; and intracellular domain: 106 amino acids domain from No. 1063 arginine to No. 1187 valine. These domains are estimated domain construction from amino acid sequences, and actual presence form may differ from the above structure, and constitutional amino acids of each domain hereinabove defined may have possibility to change 5 to 10 amino acids sequence.

According to a comparison in amino acid sequence of human serrate-1 and Serrate homologue of the other organisms, the homologies with *Drosophila* Serrate, and rat Jagged are 32.1% and 95.3%, respectively. The human Serrate-1 of the present invention is different from these Serrates and is novel substance which is clarified at first by the present inventors. Search from all of organisms in the above data base indicated that polypeptides having the identical sequence of the human Serrate-1 could not find out.

The homologues of Notch ligand have evolutionally conserved common sequence, i.e. repeated DSL sequence and EGF-like sequence. As a result of comparison with amino acid sequence of human Serrate-1 and other Notch ligand homologues, these conserved sequence is estimated. Namely, DSL sequence corresponds to 43 amino acids residue from No. 156 cysteine to No. 198 cysteine of the amino acid sequence in the sequence listing, SEQ ID NO: 7. EGF-like sequence exists with 16 repeats wherein, in the amino acid sequence in the sequence listing, SEQ ID NO: 7, the first EGF-like sequence from No. 205 cysteine to No. 231 cysteine; the second EGF-like sequence from No. 234 cysteine to No. 262 cysteine; the third EGF-like sequence from No. 269 cysteine to No. 302 cysteine; the fourth EGF-like sequence from No. 309 cysteine to No. 340 cysteine; the fifth EGF-like sequence from No. 356 cysteine to No. 378 cysteine; the sixth EGF-like sequence from No. 423 cysteine to No. 453 cysteine; the eighth EGF-like sequence from No. 462 cysteine to No. 453 cysteine; the nineth EGF-like sequence from No. 498 cysteine to No. 529 cysteine; the $10^{th}$ EGF-like sequence from No. 536 cysteine to No. 595 cysteine; the 11th EGF-like sequence from No. 602 cysteine to No. 633 cysteine; the $12^{th}$ EGF-like sequence from No. 640 cysteine to No. 671 cysteine; the $13^{th}$ EGF-like sequence from No. 678 cysteine to No. 709 cysteine; the $14^{th}$ EGF-like sequence from No. 717 cysteine to No. 748 cysteine; and the $16^{th}$ EGF-like sequence from No. 793 cysteine to No. 824 cysteine. However, the $10^{th}$ EGF-like sequence has irregular sequence containing 10 residues of cysteine.

A part of sugar chain attached is estimated from amino acid Sequence of the human Serrate-1 may be No. 112, 131, 186, 351, 528, 554, 714, 1014 and 1033 asparagine residue in the sequence listing. SEQ ID NO: 7 as a possible binding site of N-glycoside bonding for N-acetyl-D-glycosamine. O-glycoside bond of N-acetyl-D-galactosamine is estimated to be a serine or threonine residue rich part, Protein bound with sugar chain is generally thought to be stable in vivo and to have strong physiological activity. Consequently, in the amino acid sequence of polypeptide having sequence of the sequence listing, SEQ ID NO: 5, 6 or 7, polypeptides having N-glucoside or O-glucoside bond with sugar chain of N-acetyl-D-glucosamine or N-acetyJ-D-galactosamine is included in the present invention.

As a result of studies on binding of *Drosophila* Notch and its ligand, amino acid region necessary for binding with ligand of *Drosophila* Notch with the Notch is from N-terminal to DSL sequence of the matured protein, in which signal peptide is removed (Japan. Pat. PCT Unexam. Publ. No. 7-503121). This fact indicates that a domain necessary for expression of ligand action of human Notch ligand molecule is at least the DSL domain, i.e. a domain containing amino acid sequence of the sequence listing. SEQ ID NO: 1, and a domain at least necessary for expression of ligand action of human Delta-1 is novel amino acid sequence shown in the sequence listing, SEQ ID NO: 2, and further a domain at least necessary for expression of ligand action of human Serrate-1 is novel amino acid sequence shown in the sequence listing, SEQ ID NO: 5.

An mRNA of human Delta-1 can be detected by using DNA coding a part or all of gene sequence in the sequence listing, SEQ ID NO: 8, and an mRNA of human Serrate-1 can be detected by using DNA coding a part or all of gene sequence in the sequence listing, SEQ ID NO: 10. For example, a method for detection of expression of these genes can be achieved by applying with hybridization or PCR by using complementary nucleic acids of above 12 mer or above 16 mer, preferably above 18 mer having nucleic acid sequence of a part of sequence in the sequence listing, SEQ ID NO: 8 or 10 i.e. antisense DNA or antisense RNA, its methylated, methylphosphated, deaminated, or thiophosphated derivatives. By the same method, detection of homologues of the gene of other organisms such as mice or gene cloning can be achieved. Further cloning of genes in the genome including humans can be made. Using these genes cloned by such like methods, further detailed functions of the human Delta-1 or human Serrate-1 of the present invention can be clarified. For example, using the modern gene manipuration techniques, every methods including transgenic mouse, gene targeting mouse or double knockout mouse in which genes relating to the gene of the present invention are inactivated, can be applied. If abnormalities in the genome of the present gene is found, application to gene diagnosis and gene therapy can be made.

A transformant in which vector pUCDL-1F, which contains cDNA coding total animo acid sequence of human Delta-1 of the present invention, is transformed into *E. coli* JM109, has been deposited in the National Institute of Bioscience and Human-Technology, Agency of Industrial Science and Technology, MITI, of 1–1–3, Higasi, Tsukuba-shi, Ibaragi-ken, Japan, as *E. coli*: JM109-pUCDL-1F. Date of deposit was Oct. 28, 1996, and deposition No. is FBRM BP-5728. A transformant in which vector pUCSR-1, which contains cDNA coding total animo acid sequence of human Serrate-1 of the present invention, is transformed into *E. coli* JM109, has been deposited in the National Institute of Bioscience and Human-Technology, Agency of industrial Science and Technology, MITI, of 1–1–3, Higasi, Tsukuba-shi, Ibaragi-ken, Japan, as *E. coli*:JM109-pUCSR-1. Date of deposit was Oct. 28, 1996, and deposition No. is FBRM BP-5726.

Exprssion and purification of various forms of human Delta-1 and human Serrate-1 using cDNA coding amino acid sequence of human Delta-1 and human Serrate-1 isolated by the above methods are known in the references (Kriegler, Gene Transfer and Expression—A Laboratory Manual Stockton Press. 1990 and Yokota et al. Biomanual Series 4, Gene transfer and expression and analysis, Yodosha Co., 1994). A cDNA coding the amino acid sequence of the isolated said human Delta-1 and human Serrate-1 is ligated to preferable expression vector and is produced in the host cells of eukaryotic cells such as animal cells and insect cells or prokaryotic cells such as bacteria.

In the expression of human Delta-1 and human Serrate-1 of the present invention, DNA coding polypeptide of the present invention may have the translation initiation codon in 5'-terminal and translation termination codon in 3'-terminal. These translation initiation codon and translation termination codon can be added by using preferable synthetic DNA adapter. Further for expression of the said DNA, promoter is linkaged in the upstream of the DNA sequence. Examples of vector are plasmid originated from *Bacillus*, plasmid originated from yeast or bacteriophage such as λ-phage and animal virus such as retrovirus and vaccinia virus.

Examples of promoters used in the present invention are any promoters preferable for corresponding to the host cells used in gene expression.

In case that the host cell in the transformation is genus *Eseherichia*, tac-promoter, trp-promoter and lac-promoter are preferable, and in case of host of genus *Bacillus*, SP01 promoter and SP02 promoter are preferable, and in case of host of yeast, PGK promoter, GAP promoter and ADH promoter are preferable.

In case that the host cell is animal cells, a promoter originated from SV40 such as SRα promoter as described in Example 51 promoter of retrovirus, metallothionein promoter and heatshock promoter can be applied.

Polypeptide of the present invention can be expressed by using the expression vector having ability to be used by any person skilled in the arts.

Expression of the polypeptide of the present invention can be made by using only DNA coding the amino acid sequence of the sequence listing, SEQ ID NO: 2, 3, 4, 5, 6 or 7. However, the protein added with specific function can be produced by using DNA, to which added cDNA coding the known antigen epitope for easier detection of the produced polypeptide or added cDNA coding the immunoglobulin Fc for forming multimer.

As shown in Example 5, we have prepared expression vectors, which express extracellular proteins of human Delta-1, as follows:

1) DNA coding the amino acids from No. 1 to 520 in amino acid sequence in the sequence listing, SEQ ID NO: 3,
2) DNA coding chimera protein to which added polypeptide having 8 amino acid, i.e. an amino acid sequence consisting of Asp Tyr Lys Asp Asp Asp Asp Lys (hereinafter designates FLAG sequence, the sequence listing, SEQ ID NO: 12), in the C-terminal of the amino acids from No. 1 to 520 in amino acid sequence in the sequence listing, SEQ ID NO: 3, and
3) DNA coding chimera protein to which added Fc sequence below the hinge region of human IgG1 (refer to International Patent Publ. WO96/11221 in the C-terminal of the amino acids from No. 1 to 520 in amino acid sequence in the sequence listing, SEQ ID NO:3, and to have dimer structure by disulfide bond in the hinge region, are ligated individually with the expression vector pMKIT-Neo (Maruyama et al. Japan Molecular Biology Soc. Meeting Preliminary lecture record, obtainable from Dr. Maruyama in Tokyo Medical and Dental College, containing promoter SRα) to prepare extracellular expression vectors of human Delta-1.

The full-length expression vectors of the human Delta-1 as the expression vectors, which express full-length proteins of the human Delta-1, can be prepared as follows.

4) DNA coding amino acids from No. 1 to 702 in the sequence listing, SEQ ID NO: 4 and
5) DNA coding chimera protein to which added polypeptide having FLAG sequence in the C-terminal of amino acids from No. 1 to 702 in the sequence listing, SEQ ID NO: 4 are ligated individually with the expression vector pMKIT-Neo to prepare the full-length expression vectors of human Delta-1. The transformant is prepared by using expression plasmid containing DNA coding the thus constructed said human Delta-1.

As shown in Example 6, we have prepared expression vectors, which express extracellular proteins of human Serrate-1, as follows.

6) DNA coding the amino acids from No. 1 to 1036 in amino acid sequence in the sequence listing, SEQ ID NO: 6,
7) DNA coding chimera protein to which added polypeptide having FLAG sequence in the C-terminal of the amino acids from No. 1 to 1036 in amino acid sequence in the sequence listing, SEQ ID NO: 6, and
8) DNA coding chimera protein to which added said Fc sequence in the C-terminal of the amino acids from No. 1 to 1036 in amino acid sequence in the sequence listing, SEQ ID NO: 6, and to have dimer structure by disulfide bond in the hinge region, are ligated individually with the expression vector pMKIT-Neo to prepare extracellular expression vectors of human Serrate-1.

The full-length expression vectors of the human Serrate-1 as the expression vectors, which express full-length proteins of the human Serrate-1, can be prepared as follows.

9) DNA coding amino acids from No. 1 to 1187 in the sequence listing, SEQ ID NO: 7 and
10) DNA coding chimera protein to which added polypeptide having FLAG sequence in the C-terminal of amino acids from No. 1 to 1187 in the sequence listing, SEQ ID NO: 7 are ligated individually with the expression vector pMKIT-Neo to prepare the full-length expression vectors of human Serrate-1. The transformant is prepared by using expression plasmid containing DNA coding the thus constructed said human Serrate-1.

Examples of the host are genus *Escherichia*, genus *Bacillus*, yeast and animal cells. Examples of animal cells are simian cell COS-7 and Vero, Chinese hamster cell CHO and silk worm cell SF9.

As shown in Example 7, the above expression vectors 1)–10) are transduced individually; the human Delta-1 or human Serrate-1 are expressed in COS-7 cell (obtainable from the Institute of Physical and Chemical Research. Cell Development Bank, RCB0539), and the transformants which were transformed by these expression plasmids, can be obtained. Further, human Delta-1 polypeptide and human Serrate-1 polypeptide can be produced by culturing the transformants under preferable culture condition in medium by known culture method.

As shown in Example 8, human Delta-1 polypeptide and human Serrate-1 polypeptide can be isolated and purified from the above cultured mass, in general, by the following methods.

For extraction of the substance from cultured microbial cells or cells, microbial cells or cells are collected by known method such as centrifugation after the cultivation, suspended in preferable buffer solution, disrupted the microbial cells or cells by means of ultrasonication, lysozyme and/or freeze-thawing and collected crude extract by centrifugation or filtration. The buffer solution may contain protein-denaturing agents such as urea and guanidine hydrochloride or surface active agents such as Triton-X. In case of secretion in the cultured solution, the cultured mass is separated by the known method such as centrifugation to separate from microbial cells or cells and the supernatant solution is collected.

The thus obtained human Delta-1 or human Serrate-1, which are contained in the cell extracts or cell supernatants, can be purified by known protein purification methods. During the purification process, for confirmation of existence of the protein, in case of the fused proteins of the above FLAG and human IgGFc, they can be detected by immunoassay using antibody against known antigen epitope and can be purified. In case of not to express as such the fused protein, the antibody in Example 9 can be used for detection.

Antibodies, which specifically recognize human Delta-1 and human Serrate-1, can be prepared as shown in Example 9. Antibodies can be prepared by the methods described in the reference (Antibodies a laboratory manual, E. Harlow et al., Cold Spring Harbor Laboratory) or recombinant antibodies expressed in cells by using immunoglobulin genes isolated by gene cloning method. The thus prepared antibodies can be used for purification of human Delta-1 and human Serrate-1. The human Delta-1 or human Serrate-1 can be detected and assayed by using antibodies which recognize specifically human Delta-1 or human Serrate-1 as shown in Example 9, and can be used for diagnostic agents for diseases accompanied with abnormal differentiation of cells such as malignant tumors.

More useful purification method is the affinity chromatography using antibody. Antibodies used in this case are antibodies described in Example 9. For fused protein, antibodies against FLAG in the case of FLAG, and protein G or protein A in the case of human IgGFc as shown in Example 8.

Any fused protein other than the protein as shown hereinabove can be used. For example, histidine Tag and myc-tag can be mentioned. Any fused proteins can be prepared by using methods of present day genetic engineering techniques other than the known methods, and peptides of the present invention derived from those fused proteins are in the scope of the present invention.

Physiological functions of the thus purified human Delta-1 and human Serrate-1 proteins can be identified by various assay methods, for example, physiological activity assaying methods using cell lines and animals such as mice and rats, assay methods of intracellular signal transduction based on molecular biological means, binding with Notch receptor etc.

We have observed actions for blood undifferentiated cells by using IgG1 chimera proteins of human Delta-1 and human Serrate-1.

As a result, we have found that, as shown in Example 10, in the umbilical cord blood derived blood undifferentiated cells, in which CD34 positive cell fraction is concentrated, polypeptides of the present invention have suppressive action of colony forming action against blood undifferentiated cells, which shows colony formation in the presence of cytokines. The suppressive action is only observed in the presence of SCF. This kind of effect has never been known.

As shown in Example 11, we have found that a maintenance of colony forming cells is significantly extended by addition of IgG1 chimera protein of human Delta-1 or human Serrate-1 in the long term (8 weeks) liquid culture in the presence of cytokines such as SCF, IL-3, IL-6, GM-CSF and Epo. Further we have found that the polypeptides of the present invention had an action not to suppress growth of the colony forming cells. A cytokine, MIP-1α having migration and differentiation suppressive action of blood cells (Verfaillie et al., J. Exp. Med. 179, 643–649, 1994), has no action for maintaining undifferentiation for blood undifferentiated cells.

Further as shown in Example 12, we have found that as a result of adding IgG1 chimera protein of human Delta-1 or human Serrate-1 to the liquid culture in the presence of cytokines, the human Delta-1 and human Serrate-1 had activities for significantly maintaining LTC-IC (Long-Term Culture-Initiating Cells) number, which is positioned most undifferentiated blood stem cells in the human blood undifferentiated cells.

These results indicate that the human Delta-1 and human Serrate-1 suppress differentiation of blood undifferentiated cells, and these actions spread from blood stem cells to colony forming cells. These physiological actions are essential for in vitro expansion of blood undifferentiated cells. Cells cultured in the medium containing human Delta-1 or human Serrate-1 are efficient in recovery of suppresion of bone marrow after administration of antitumor agents, accordingly in vitro growth of hemopoietic stem cells may be possible if other conditions would be completed. Further pharmaceuticals containing the polypeptide of the present invention have action protection and release of the bone marrow suppressive action, which is observed in adverse effects of antitumor agents.

Suppressive action for differentiation of cells in the undifferentiated cells other than blood cells is expected and stimulating action for tissue regeneration can be expected.

In the pharmaceutical use, polypeptides of the present invention are lyophilized with adding preferable stabilizing agents such as human serum albumin, and is used in dissolved or suspended condition with distilled water for injection when it is in use. For example, preparation for injection or infusion at the concentration of 0.1–1000 μg/ml may be provided. A mixture of the compound of the present invention 1 mg/ml and human serum albumin 1 mg/ml divided in a vial could maintain activity of the said compound for long term. For culturing and activating cells in vitro, lyophilized preparation or liquid preparation of the polypeptide of the present invention are prepared and are added to the medium or immobilized in the vessel for culture. Toxicity of the polypeptide of the present invention was tested. Any polypeptide, 10 mg/kg was administered intraperitoneally in mice, but no death of mice was observed.

In vitro physiological activity of the polypeptide of the present invention can be evaluated by administering to disease model mice or its resembled disease rats or monkeys, and examining recovery of physical and physiological functions and abnormal findings. For example, in case of searching abnormality in relation to hemopoietic cells, bone marrow suppressive model mice are prepared by administering 5-FU series of antitumor agents, and bone marrow cell counts, peripheral blood cell counts and physiological functions are examined in the administered group or the non administered group of mice. Further, in case of searching in vitro cultivation and growth of hemopoietic undifferentiated cells including hemopoietic stem cells, the bone marrow cells of mice are cultured in the groups with or without addition of the compound of the present invention, and the cultured cells are transferred into the lethal dose irradiated mice. Result of recovery is observed with the indications of survival rate and variation of blood counts. These results can be extrapolated to the humans, and accordingly useful effective data for evaluation of the pharmacological activities of the compound of the present invention can be obtained.

Applications of the compound of the present invention for pharmaceuticals include diseases with abnormal differentiation of cells, for example leukemia and malignant tumors. These are cell therapy, which is performed by culturing human derived cells in vitro while maintaining their original functions or adding new functions, and a therapy, which is performed by regenerating without damaging the functions originally existing in the tissues by administering the compound of the present invention under the regeneration after tissue injury. Amount of administration may differ in the type of preparation and ranges from 10 μg/kg to 10 mg/kg.

Further strong physiological activity can be achieved by expression of forming multimer of the polypeptide of the present invention.

As shown in Example 10, since the suppressive action of human Delta-1 and human Serrate-1 is stronger in the IgG chimera protein having dimer structure, a form of stronger physiological activity is preferably expressed in the form of multimer formation.

Human Delta-1 and human Serrate-1 having multimer structure can be produced by a method of expressing chimera protein with human IgG Fc region as described in the example and expressing the multimer having disulfide bond with hinge region of the antibody, or a method expressing chimera protein, in which antibody recognition region is expressed in the C-terminal or N-terminal, and reacting with the polypeptide containing extracellular part of the thus said Delta-1 and Human Serrate-1 and/the antibody which recognize specifically the antibody recognition region in the C-terminal or N-terminal. In the other methods, a method, in which a fused-protein expressed with only the hinge region of the antibody and the dimerized by disulfide bond, can be mentioned. The multimer of human Delta-1 and human Serrate-1 having higher specific activity than the dimer can be obtained. The said multimer is constructed by fused protein which is prepared for expressing the peptide in the C-terminal, N-terminal or other region. The protein is prepared in the form of forming disulfide bond without effecting in any activities of the other human Delta-1 or human Serrate-1. The multimer structure can also be expressed by arranging one or more peptide, which is selected from polypeptides containing amino acids sequence of the sequence listing, SEQ ID NO: 2, 3, 5 or 6, with genetic engineering method in series or in parallel. Other known methods for providing multimer structure having dimer or higher can be applied. Accordingly, the present invention includes any polypeptides containing amino acid sequences described in the sequence listing, SEQ ID NO: 2, 3, 5 or 6 in the form of dimer or higher more structure prepared by genetic engineering technique.

Further in the other method, multimerization method using chemical cross-linker can be mentioned. For example, dimethylsuberimidate dihydrochloride for cross-linking lysine residue, N-(γ-maleimidebutyryloxy) succinimide for cross-linking thiol group of cysteine residue and glutaraldehyde for cross-linking between amino groups can be mentioned. The multimer with dimer or more can be synthesized by applying these cross-linking reactions. Accordingly, the present invention includes any polypeptides containing amino acid sequences described in the sequence listing, SEQ ID NO: 2, 3, 5 or 6 in the form of dimer or more structure prepared by chemical cross-linking agents.

In application of medical care in which cells are proliferated and activated in vitro and are returned to the body, human Delta-1 or human Serrate-1 of the form hereinabove can be added directly in the medium, but immobilization can also be made. Immobilization method includes applying amino group or carboxyl group in the peptide, using suitable spacers or the above mentioned cross-linkers, and the polypeptide can be covalently bound to the culture vessels. Accordingly, the present invention includes any polypeptides containing amino acid sequences described in the sequence listing, SEQ ID NO: 2, 3, 5 or 6 in the form of existing on the solid surface.

Since the natural human Delta-1 and human Serrate-1 are cell membrane proteins, differentiation suppressive action in the Examples can be expressed by cocultivating with cells expressing these molecules and blood undifferentiated cells. Consequently, this invention includes cocultivation method with transformed cells by using DNA coding amino acid sequences in the sequence listing, SEQ ID NO: 2–7 and undifferentiated cells.

Expressed cell may be COS-7 cell as shown in Examples, but cells of human origin are preferable, and further expressed cells may be cell line or any of human in vivo blood cells and somatic cells. Consequently, the polypeptide can be expressed in vivo by integrated into vectors for gene therapy.

As shown in Example 10, FLAG chimera protein of human Delta-1 or human Serrate-1, both of which are low concentrated monomer, shows not a colony formation suppressive action but a colony formation stimulating action. This action may be involved in expressing Notch receptor and Notch ligand in the occasion of cell division of blood undifferentiated cells and acting the polypeptide of the present invention as an antagonist for that action. This suggests that the polypeptide having amino acid sequence of the sequence listing, SEQ ID NO: 1, 2, 4 or 5, shows colony formation stimulation action by controlling the concentration of its action.

This fact suggests that inhibition of binding the polypeptide having amino acid sequence in the sequence listing, SEQ ID NO: 2–7 and these receptors can be used for finding out molecules and compounds for stimulating cell differentiation. The methods include binding experiment using radio isotope, luciferase assay using transcriptional control factors, a down stream molecule of the Notch receptor, and simulation on the computer by X-ray structural analysis. Accordingly, the present invention includes screening method for pharmaceuticals using polypeptide in the sequence listing, SEQ ID NO: 2–7.

As shown in Example 13, specific leukemia cells can be differentiated by using IgG chimera protein of human Delta-1 or human Serrate-1. Consequently, the present invention can be applied for diagnostic reagents for leukemia or isolation of specific blood cells. This result indicates that human Delta-1 or human Serrate-1 molecule binds specifically with its receptor, a Notch receptor molecule. For example, expression of Notch receptor can be detected by using fused protein with the above extracellular region and human IgGFc. Notch is known to involve in some type of leukemia (Ellisen et al., Cell 66, 649–661, 1991). Accordingly, the polypeptide having amino acids sequence in the sequence listing, SEQ ID NO: 2, 3, 5 and 6 can be used for diagnostic reagents for in vitro or in vivo.

BRIEF EXPLANATION OF THE DRAWINGS

FIG. 1: Alignment of DSL domain of Notch ligand identified in various organisms including the molecules of the present invention, wherein the consensus sequence is SEQ ID NO: 40, hDelta-1.DSL is SEQ ID NO: 41, dDelta.DSL is SEQ ID NO: 42, xDelta.DSL is SEQ ID NO: 43, cDelta-1.DSL is SEQ ID NO: 44, mDelta-1.DSL is SEQ ID NO: 45, hSerrate-1.DSL is SEQ ID NO: 46, dSerrate.DSL is SEQ ID NO: 47, and rJagged.DSL is SEQ ID NO: 48.

FIGS. 2A and 2B: Suppression of colony formation of the blood undifferentiated cells using the molecules of the present invention.

FIG. 4: A graph showing calculation of LTC-1 after liquid culture using the molecules of the present invention.

FIGS. 5A and 5B: Cells stained by the molecules of the present invention.

EXAMPLES

Figure 3:
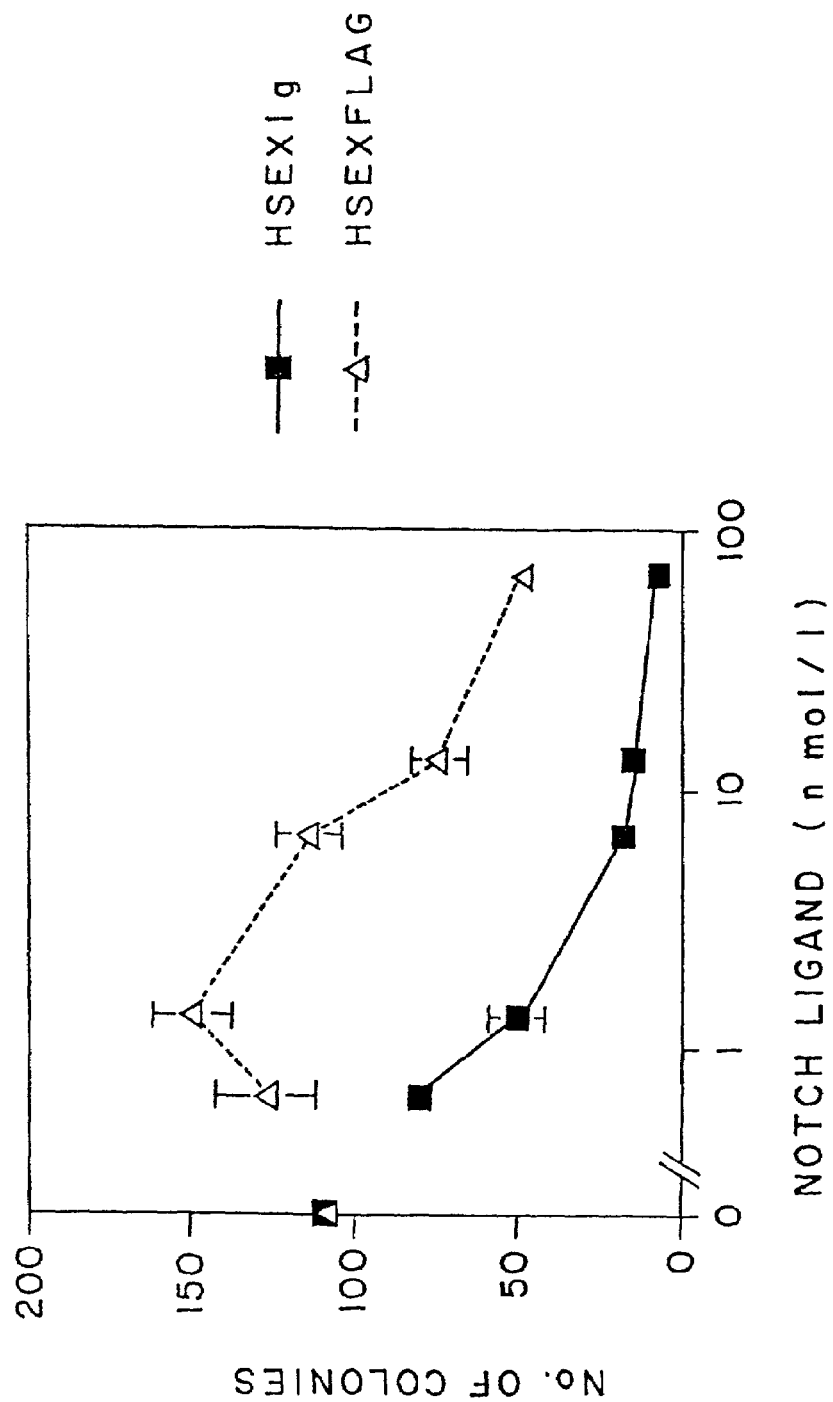
FIG. 3: Concentration dependency of colony formation suppression of the blood undifferentiated cells using the molecules of the present invention.

Following examples illustrate the embodiments of the present invention but are not construed as limiting these examples.

Example 1

Cloning of PCR Products using Human Delta-1 Primer and Determination of Base Sequence A mixed primer corresponding to amino acid sequence conserved in C-Delta-1 and X-Delta-1, i. e. sense primer DLTS1 (sequence listing, SEQ ID NO: 14) and antisense primer DLTA2 (sequence listing, SEQ ID NO: 15), were used.

A synthetic oligonucleotide was prepared by using automatic DNA synthesizer with the principle of immobilized method. The automatic DNA synthesizer used was 391PCR-MATE of Applied Biosystems Inc., U.S.A. Nucleotide, carrier immobilized with 3'-nucleotide, solution and reagents are used according to the instructions by the same corporation. Oligonucleotide was isolated from the carrier after finishing the designated coupling reaction and treating the oligonucleotide carrier, from which protective group of 5'-teminal was removed, with concentrated liquid ammonia at room temperature for one hour. For removing the protective groups of nucleic acid and phosphoric acid, the reactant solution containing nucleic acid was allowed to stand in the concentrated ammonium solution in the sealed vial at 55° C. for over 14 hours. Each oligonucleotide, from which the carrier and protective groups were removed, was purified by using OPC cartridge of the Applied Biosystems Inc., and detrytilated by using 2% trifluoracetic acid. Primer was dissolved in deionized water to set final concentration of 100 pmol/µl after purification.

Amplification of these primers by PCR was performed as follows. Human fetal brain originated cDNA mixed solution (QUICK-Clone cDNA, CLONTECH Inc., U.S.A.) 1 µl was used. 10×buffer solution [500 mM KCl, 100 mM Tris-HCl (pH 8.3), 15 mM $MgCl_2$, 0.01% gelatin] 5 µl dNTP mixture (Takara Shuzo Co., Japan) 4 µl, sense primer DLTS1 (100 pmol/µl) 5 µl which was specific to the above vertebrates and antisense primer DLTA2 (100 pmol/µl) 5 µl and TaqDNA polymerase (AmpliTaq, Takara Shuzo Co., Japan, 5 U/µl) 0.2 µl were added thereto, and finally deionized water was added to set up total 50 µl. PCR was performed by 5 cycles of a cycle consisting of treatment at 95° C. for 45 seconds, at 42° C. for 45 seconds and 72° C. for 2 minutes, further 35 cycles of a cycle consisting of treatment at 95° C. for 45 seconds, at 50° C. for 45 seconds and 72° C. for 2 minutes, and finally allowed to stand at 72° C. for 7 minutes. A part of the PCR products was subjected to 2% agarose gel electrophoresis, stained with ethidium bromide (Nippon Gene Co., Japan), and observed under ultraviolet light to confirm amplification of about 400 bp DNA.

Total amount of PCR product was subjected to electrophoresis with 2% agarose gel prepared by low melting point agarose (GIBCO BRL Inc., U.S.A.), stained by ethidium bromide, cutting out about 400 bp bands of PCR products by the Delta primer under the UV light, adding distilled water of the same volume of the gel, heating at 65° C. for 10 minutes, and completely dissolving the gel. The dissolved gel was centrifuged at 15000 rpm for 5 minutes to separate supernatant solution after adding equal volume of TE saturated phenol (Nippon Gene Co., Japan) and the same separation operation was performed after adding TE saturated phenol : chloroform (1:1) solution and chloroform. DNA was recovered from the final solution by ethanol precipitation.

A vector, pCRII vector (Invitorogen Inc., U.S.A., hereinafter designates as pCRII) was used. The vector and the above DNA in molar ratio of 1:3 were mixed and DNA was ligated into the vector by using T4 DNA ligase (Invitorogen Inc., U.S.A.). The pCRII, to which DNA was integrated, was subjected to gene transduction into *E. coli* one shot competent cells (Invitorogen Inc., U.S.A.) and was spread on the semi-solid medium plate of L-Broth (Takara Shuzo Co., Japan) containing ampicillin (Sigma Corp., U.S.A.) 50 µg/ml and allowed to stand at 37° C. for about 12 hours. The resulting colonies were randomly selected, inoculated in the L-Broth liquid medium 2 ml containing same concentration of ampicillin and shake cultured at 37° C. for about 18 hours. The cultured bacterial cells were recovered and the plasmid was separated by using Wizard Miniprep (Promega Inc., U.S.A.) according to the attached explanation sheet. The plasmid was digested by restriction enzyme EcoRI. Integration of the said PCR product was confirmed by incision of about 400 bp DNA. Base sequence of the incorporated DNA in the confirmed clone was determined by the fluorescent DNA sequencer (Model 373S, Applied System Inc., U.S.A.)

Example 2

Cloning of Full Length Novel Human Delta-1 and its Analysis

A screening of clones having full length cDNA was performed by hybridization from human placenta origin cDNA library (inserted cDNA in λgt-11, CLONTECH Inc., U.S.A.) in plaques corresponding to $1\times10^6$ plaques. Generated plaques were transferred onto nylon filter (Hybond N+: Amersham Inc., U.S.A.). The transcribed nylon filter was subjected to alkaline treatment [allow to stand for 7 minutes on the filter paper permeated with a mixture of 1.5 M NaCl and 0.5 M NaOH], followed by two neutralizing treatments [allow to stand for 3 minutes on the filter paper permeated with a mixture of 1.5 M NaCl, 0.5 M Tris-HCl (pH 7.2) and 1 mM EDTA]. Subsequently, the filter was shaken for 5 minutes in the 2-fold concentrated SSPE solution [0.36 M NaCl, 0.02 M sodium phosphate (pH 7.7) and 2 mM EDTA], washed and air-dried. Then the filter was allowed to stand for 20 minutes on the filter paper, which was permeated with 0.4 M NaOH, shaken for 5 minutes with 5-fold concentrated SSPE solution and washed, then again air-dried. Screening was conducted in the human Delta-1 probe labeled with radioisotope $^{32}$P using these filters.

DNA probe prepared in Example 1 was labeled with $^{32}$P as follows. A DNA fragment was cutted out by EcoRI from pCRII, inserted a purified PCR product (about 400 bp) by human Delta-1 primer and determined gene sequence, and was isolated from low melting point agarose gel. The thus obtained DNA fragment was labeled by DNA labeling kit (Megaprime DNA labeling system: Amersham, U.S.A.). The primer solution 5 µl and deionized water were added to DNA 25 ng to set up total volume of 33 µl which was treated for 5 minutes in boiling water bath. Reaction buffer solution 10 µl containing dNTP, $\alpha$-$^{32}$P-dCTP 5 µl and T4 DNA polynucleotide kinase solution 2 µl were added thereto, treated at 37° C. for 10 minutes in water bath. Subsequently, the mixture was purified by Sephadex column (Quick Spin Column Sephadex G-50: Boehringer Mannheim Inc., Germany), then treated for 5 minutes in boiling water bath and ice-cooled for 2 minutes for use.

Hybridization was performed as follows. The prepared filter hereinabove was immersed into the prehybridization solution consisting of SSPE solution, in which final concentration of each component is set at 5-fold concentration, 5-fold concentration of Denhardt's solution (Wako Pure Chemicals, Japan), 0.5% SDS (sodium dodecyl sulfate, Wako Pure Chemicals, Japan) and salmon sperm DNA (Sigma, U.S.A.) 10 µg/ml denatured by boiling water, and shaken at 65° C. for 2hours, then the filter was immersed into the hybridization solution of the same composition with the above prehybridization solution with the $^{32}$P-labeled probe above mentioned and shaken at 65° C. for 2 hours for 16 hours to perform hybridization.

The filter was immersed into SSPE solution containing 0.1% SDS, shaken at 55° C. and washed twice, further immersed into 10-fold dilution of SSPE solution containing 0.1% SDS and washed four times at 55° C. An autoradiography of the washed filter was performed using intensified screen. Clones of strongly exposed part were collected and the plaques obtained were again spread and screened by the same method hereinbefore to separate complete single clones.

The thus isolated phage clones were seven clones. Phage of all of these clones was prepared to about $1\times10^9$ pfu, purified the phage DNA, digested by restriction enzyme EcoRI and inserted into pBluescript (Stratagene Inc., U.S.A.) which was digested EcoRI in the same way. DNA sequences of the both ends of these clones were analyzed by DNA sequencer. Three clones of D5, D6 and D7 were the clone containing DNA sequence from No. 1 to 2244 in the sequence listing, SEQ ID NO: 8. A clone D4 was a clone containing DNA sequence from No. 999 to 2663 in the sequence listing, SEQ ID NO: 8. The clones D5 and D4 prepared the deletion mutant by using kilosequence deletion kit (Takara Shuzo Co., Japan) according to a description of the attached paper. Full-length cDNA base sequence of the present invention was determined using the DNA sequencer from both direction of 5'-direction and 3'-direction.

By applying with XhoI site at No. 1214 in DNA sequence in the sequence listing, SEQ ID NO: 8, D4 and D5 were digested by restriction enzyme XhoI to prepare plasmid pBSDel-1 containing full length of DNA sequence in the sequence listing, SEQ ID NO: 8.

Example 3

Cloning of Human Serrate-1 Specific PCR Product and Determination of Base Sequence A mixed primer, which corresponded to amino acid sequence conserved in *Drosophila* Serrate and rat Jagged, i.e. sense primer SRTS 1 (the sequence listing. SEQ ID NO: 16 ) and antisense primer SRTA2 (the sequence listing, SEQ ID NO: 17), was used. Preparation was conducted by the same way as described in Example 1.

Amplification by PCR using these primers was performed as follows. To the human fetal brain originated cDNA mixed solution hereinbefore 1 μl was added 10× buffer solution (described in Example 1) 5 μl, said dNTP mixture 4 μl, sense primer SRTS1 (100 pmol/μl) 5 μl and antisense primer SRTA2 (100 pmol/μl) 5 μl specific to Serrate-1 homologue hereinbefore, and said TaqDNA polymerase 0.2 μl, and finally added deionized water to set up total volume 50 μl. The mixture was treated for 5 cycles of a cycle consisting of at 95° C. for 45 seconds, at 42° C. for 45 seconds and 72° C. for 2 minutes, and 35 cycles of a cycle consisting of at 95° C. for 45 seconds, at 50° C. for 45 seconds and 72° C. for 2 minutes, and finally allowed to stand at 72° C. for 7 minutes to perform PCR. A part of the PCR product was subjected to 2% agarose gel elctrophoresis, stained by ethidium bromide, and observed under ultraviolet light to confirm amplification of about 500 bp cDNA.

Total amount of PCR product was subjected to electrophoresis with 2% agarose gel prepared by low melting point agarose, stained by ethidium bromide, cutting out about 500 bp bands under the UV light, adding distilled water of the equal volume of the gel, heating at 65° C. for 10 minutes, and completely dissolving the gel. The dissolved gel was centrifuged at 15000 rpm for 5 minutes to separate supernatant solution after adding equal volume of TE saturated phenol and the same separation operation was performed after adding TE saturated phenol:chloroform (1:1) solution and chloroform. DNA was recovered from the final solution by ethanol precipitation.

A vector, pCRII vector was used. The vector and the above DNA were mixed in molar ratio of 1:3 and DNA fragment was ligated into the vector pCRII by the same method in Example 1. The pCRII, to which DNA was integrated, was subjected to gene transduction into *E. coli*. The resulting colonies were randomly selected and were inoculated in liquid medium L-Broth 2 ml containing the same concentration of ampicillin and shake cultured at 37° C. for about 18 hours. The cultured bacterial cells were recovered and the plasmid was separated by using the Wizard Miniprep according to the attached explanatory sheet. The plasmid was digested by restriction enzyme EcoRI. Integration of the said PCR product was confirmed by incision of about 500 bp DNA. Base sequence of the incorporated DNA in the confirmed clone was determined by the fluorescent DNA sequencer.

Example 4

Cloning of Full Length Novel Human Serrate-1 and its Analysis

A screening of clones having full length cDNA was performed by hybridization from the human placenta origin cDNA library hereinbefore in plaques corresponding to 1×10$^6$ plaques. Preparation of the filter was performed by the same method as described in Example 2. Screening was conducted in the human Serrate-1 probe labeled with radioisotope $^{32}$P using the filter.

The above DNA probe labeled with $^{32}$P was prepared by a method described in Example 2, and hybridization, washing of the filter and isolation of the clone were performed by the description in Example 2.

The thus isolated phage clones were 22 clones. Phage of all of these clones was prepared to about 1×10$^9$ pfu, purified the phage DNA, digested by restriction enzyme EcoRI and inserted into pBluescript which was digested EcoRI in the same way. DNA sequences of the both ends of these clones were analyzed by DNA sequencer. Two clones of S16 and S20 were the clone containing DNA sequence from No. 1 to 1873 in the sequence listing, SEQ ID NO: 10. Two clones S5 and S14 were the clones containing DNA sequence from No.990 to 4005 in the sequence listing, SEQ ID NO: 10. These clones prepared the deletion mutants by using the kilosequence deletion kit according to a description of the attached leaflet. The cDNA base sequence coding the polypeptide of the present invention was determined using the DNA sequencer from both direction of 5'-direction and 3'-direction.

By applying with BglII site at No.1293 in DNA sequence in the sequence listing, SEQ ID NO: 10. S20 and S5 were digested by restriction enzyme BglII, and DNA of gene sequence from-No.1 to 4005 in the sequence listing SEQ ID NO: 10 was subcloned in *E. coli* vector pBluescript. This plasmid is named as pBSSRT.

Since the termination codon was not found in the C-terminal and the intracellular region coding C-terminal amino acids was not cloned, cloning of the full length gene was performed using the 3' RACE system kit, GIBCO-BRL, U.S.A., according to the description of the attached leaflet. The cloning of cDNA gene for 3'-direction was performed in polyA$^+$ RNA (CLONTECH Inc., U.S.A.) originated from human placenta to determine the gene sequence.

The thus cloned three gene fragments by applying with BglII site in DNA sequence No. 1293 and AccI site in DNA sequence No. 3943 and a plasmid containing full length of DNA sequence in the sequence listing, SEQ ID NO: 5 were inserted between EcoRI and Xbal in the multi-cloning site of pUC18 to prepare pUCSR-1 containing full length gene of human Serrate-1. This gene sequence as well as its amino acid sequence is shown in the sequence listing, SEQ ID NO: 10.

Example 5

Preparation of Expression Vectors of Human Delta-1

Using the gene consisting of DNA sequence described in the sequence listing, SEQ ID NO: 7, expression vectors of human Delta-1 protein mentioned in the following 1)–5) were prepared. Addition of restriction enzyme sites and insertion of short gene sequence were performed using ExSite PCR-Based Site-Directed Mutagenesis Kit (Stratagene Inc., U.S.A.) according to the operating manual.

1) Expression Vector of Soluble Human Delta-1 Protein (HDEX)

The cDNA coding polypeptide of amino acid sequence form No. 1 to 520 in the sequence listing, SEQ ID NO: 3 was ligated with expression vector pMKITNeo containing SRα promoter and neomycin resistance gene to prepare expression vector.

For preparation of expression vector of human Delta-1, in order to stable expression from gene product, EcoRI site was added in the 20 bp upper stream for 5'-direction of the initiation codon (gene sequence No. 179 in the sequence listing, SEQ ID NO: 8). Using the above Mutagenesis Kit, a plasmid pBSDel-1, which contained DNA sequence in sequence listing, SEQ ID NO: 8 and full length cDNA of human Delta-1 were set as the template, and oligonucleotides having gene sequence in sequence listing, SEQ ID NO: 18 and SEQ ID NO: 19 was set as the primers. Then DNA adding EcoRI site in the 20 bp upper stream for 5'-direction was prepared. Hereinafter this plasmid is designated as pBS/Eco-Delta.

The pBS/Eco-Delta was used as a template. In order to add the termination codon and restriction enzyme MluI site after a C-terminal position, using the Mutagenesis Kit, and setting oligonucleotides having gene sequences in the sequence listing, SEQ ID NO: 20 and SEQ ID NO: 21 as primers, addition of the termination codon and MluI site were performed. The resulted vector was digested by EcoRI and MluI, and about 1600 bp splitted gene fragment was ligated in pMKITNeo, which was treated by the same restriction enzyme, to construct the expression vector. This vector was designated as pHDEX.

2) Expression Vector of FLAG Chimera Protein of Soluble Human Delta-1 (HDEXFLAG)

The cDNA coding chimera protein, to which cDNA coding FLAG sequence was added to the C-terminal of polypeptide from No. 1 to 520 of amino acid sequence in the sequence listing, SEQ ID NO: 3, was ligated to the expression vector pMKITNeo containing SRα promoter and neomycin resistance gene to prepare the expression vector.

Using pBS/Eco-Delta as template, FLAG sequence was added in the extracellular C-terminal, i.e. after Gly at No. 520 in the sequence listing, SEQ ID NO: 3. In order to add the termination condon and restriction enzyme MluI site, using the Mutagenesis Kit, and setting oligonucleotides having gene sequence in the sequence listing, SEQ ID NO: 22 and SEQ ID NO: 21 as primers, a gene coding FLAG sequence and termination codon and MluI site were added in the C-terminal. This vector was digested by EcoRI and MluI, and about 1700 bp splitted gene fragment was ligated to the similarly restriction enzyme treated pMKITNeo to construct the expression vector. This vector was designated as pHDEXFLAG.

3) Expression Vector of IgG1Fc Chimera Protein of Soluble Human Delta-1 (HDEXIg)

A gene sequence coding polypeptide, to which amino acid sequence of Fc region below the hinge part of human IgG1 was added to the C-terminal of polypeptide having amino acid sequence in the sequence listing, SEQ ID NO: 3.

Preparation of fused protein with immunoglobulin Fc protein was performed according to the method of Zettlmeissl et al. (Zettlmeissl et al., DNA cell Biol., 9, 347–354, 1990). A gene using genome DNA with intron was applied and the said gene was prepared by using PCR. Human genome was used as a template. An oligonucleotide of the sequence in the sequence listing, SEQ ID NO: 23 with restriction enzyme BamHI site and an oligonucleotide of the sequence in the sequence listing, SEQ ID NO: 24 with restriction enzyme XbaI site were used as primers. PCR was performed using the primers and human genomic DNA as template. About 1.4 kbp band was purified, treated by restriction enzyme BamHI and XbaI (Takara Shuzo Co., Japan), and genes were ligated to pBluescript, which was similarly treated by restriction enzyme, by using T4 DNA ligase to prepare subcloning. Later, the plasmid DNA was purified and sequenced to confirm gene sequence, then the said gene sequence was confirmed as genomic DNA in the hinge region of heavy chain of the human IgG1. (The sequence is referred to Kabat et al., Sequence of Immunological Interest, NIH Publication No. 91-3242, 1991). Hereinafter this plasmid is designated as pBShIgFc.

Using the said pBS/Eco-Delta as template, and using the Mutagenesis Kit, restriction enzyme BamHI site was added in the extracellular C-terminal, i.e. after Gly at No. 520 in the sequence listing, SEQ ID NO: 3. Furthermore, in order to add restriction enzyme XbaI and MluI sites to the downstream, and setting the oligonucleotides having gene sequence in the sequence listing, SEQ ID NO: 25 and SEQ ID NO: 26, using the Mutagenesis Kit, BamHI, XbaI and MluI sites were added. This vector digested by XbaI and BamHI and about 1200 bp of gene fragment digested from the above pBShIgFc by XbaI and BamHI were ligated to prepare vector containing gene fragments coding the final objective soluble human Delta-1 IgG1Fc chimera protein. Finally, this vector was digested by EcoRI and MluI and about 3000 bp splitted gene fragments were ligated with the similarly restriction enzyme treated pMKITNeo to construct the expression vector. This vector was designated as pHDEXIg.

4) Expression Vector of Full Length Human Delta-1 Protein (HDF)

The cDNA coding polypeptide from No. 1 to 702 of amino acid sequence in the sequence listing, SEQ ID NO: 4, was ligated to the expression vector pMKITNeo containing SR α promoter and neomycin resistance gene to prepare the expression vector.

In order to add the termination codon in C-terminal of the full length sequence, i.e. after Val at No.702 in the sequence listing, SEQ ID NO: 4 and restriction enzyme MluI site, using the Mutagenesis Kit and pBS/Eco-Delta as template and setting oligonucleotides having gene sequence in the sequence listing, SEQ ID NO: 27 and SEQ ID NO: 28 as primers, the termination codon and MluI site were added in the C-terminal. This vector was digested by EcoRI and MluI, and about 2200 bp splitted gene fragment was ligated to the similar restriction enzyme treated pMKITNeo to construct the expression vector. This vector was designated as pHDF.

5) Expression Vector of FLAG Chimera Protein (HDFLAG) of Full Length Human Delta-1

The cDNA coding chimera protein, to which cDNA coding FLAG sequence was added to the C-terminal of polypeptide from No.1 to 702 of amino acid sequence in the sequence listing, SEQ ID NO: 4, was ligated to the expression vector pMKITNeo containing SRα promoter and neomycin resistance gene to prepare the expression vector.

In order to add FLAG sequence in the C-terminal, the termination codon and restriction enzyme MluI site, setting oligonucleotides having gene sequence in the sequence listing, SEQ ID NO: 29 and SEQ ID NO: 28 as primers and using pBS/Eco-Delta as template, a gene coding FLAG sequence and termination codon and MluI site were added in the C-terminal. From this vector, DNA coding full length of human Delta-1 was cloned in *E. coli* vector pUC19 to prepare vector pUCDL-1F coding full length of human Delta-1. This vector was digested by EcoRI and MluI, and about 2200 bp splitted gene fragments were ligated to the similar restriction enzyme treated pMKITNeo to construct the expression vector. This vector was designated as pHDFLAG.

Example 6

Preparation of Expression Vectors of Human Serrate-1

Using the gene consisting of DNA sequence described in the sequence listing, SEQ ID NO: 10 expression vectors of human Serrate-1 protein mentioned in the following 6)–10) were prepared. Addition of restriction enzyme sites and insertion of short gene sequence were performed by using the ExSite PCR-Based Site-Directed Mutagenesis Kit as well as according to the operating manual.

6) Expression Vector of Soluble Human Serrate-1 Protein (HSEX)

The cDNA coding polypeptide of amino acid sequence form No. 1 to 1036 in the sequence listing, SEQ ID NO: 6 was ligated with expression vector pMKITNeo to prepare expression vector.

For preparation of expression vector of polypeptide expression cells having amino acid sequence from No. 1 to 1036 in the sequence listing, SEQ ID NO: 6, in order to express gene product more stably EcoRI site was added in the 10 bp upper stream region for 5'-direction of the initiation codon (gene sequence No. 409 in the sequence listing, SEQ ID NO; 10). Using the above Mutagenesis Kit, a plasmid pBSSRT, which contained cDNA of human Serrate-1 from No. 1 to 4005 of DNA sequence in the sequence listing. SEQ ID NO: 10, was set as the template, and oligonucleotide having gene sequence in sequence listing, SEQ ID NO: 30 and oligonucleotide having gene sequence in sequence listing, SEQ ID NO: 31 were set as the primers. Then DNA adding EcoRI site in the 10 bp upper stream for 5'- direction was prepared.

The thus prepared vector (hereinafter designates as pBS/Eco-Serrate-1) was used as a template. In order to add the termination codon and further restriction enzyme MluI site in the extracellular C-terminal region, i.e. C-terminal of polypeptide in the sequence listing, SEQ ID NO: 6, using the Mutagenesis Kit, and setting oligonucleotide having gene sequence in the sequence listing, SEQ ID NO: 32 and oligonucleotide having gene sequence in the sequence listing, SEQ ID NO: 33, as primers, the termination codon and MluI site were added. The resulting vector was digested by EcoRI and MluI, and about 3200 bp splitted gene fragment was ligated in pMKITNeo, which was treated by the same restriction enzyme, to construct the expression vector. This vector was designated as pHSEX.

7) Expression Vector of FLAG Chimera Protein of Soluble Human Serrate-1 (HSEXFLAG)

The cDNA coding FLAG chimera protein, which had FLAG sequence in the C-terminal of polypeptide from No. 1 to 1036 of amino acid sequence in the sequence listing, SEQ ID NO: 6, was ligated to the expression vector pMKIT-Neo containing SRα promoter and neomycin resistance gene to prepare the expression vector.

Using pBS/Eco-Serrate-1 as a template, FLAG sequence was added in the extracellular C-terminal, i.e. the C-terminal of polypeptide in the sequence listing, SEQ ID NO: 6. In order to add the termination codon and further restriction enzyme MluI site, using the Mutagenesis Kit, and setting oligonucleotide having gene sequence in the sequence listing, SEQ ID NO: 34 and oligonucleotide having gene sequence in the sequence listing, SEQ ID NO: 33 as primers, a gene coding FLAG sequence and termination codon and MluI site were added in the C-terminal. This vector was digested by EcoRI and MluI, and about 3200 bp splitted gene fragment was ligated to the similarly restriction enzyme treated pMKITNeo to construct the exprssion vector. This vector was designated as pHSEXFLAG.

8) Expression Vector of IgG1Fc Chimera Protein of Soluble Human Serrate-1 (HSEXIg)

A gene sequence coding polypeptide, to which amino acid sequence of Fc region below the hinge part of human IgG1 was added to the C-terminal of polypeptide having amino acid sequence in the sequence listing, SEQ ID NO: 6.

In order to add restriction enzyme BamHI site in the extracellular C-terminal, i.e. after the polypeptide having the sequence in the sequence listing, SEQ ID NO: 6 and further restriction enzyme XbaI and MluI sites to its downstream, BamHI, XbaI and MluI sites were added Using pBS/Eco-Serrate-1 as a template by the Mutagenesis Kit, using oligonucleotide having gene sequence in the sequence listing, SEQ ID NO: 35 and oligonucleotide having gene sequence in the sequence listing, SEQ ID NO: 36 as primers. This vector digested by XbaI and BamHI and about 1200 bp of gene fragment digested from the above pBShIgFc by XbaI and BamHI were ligated to finally prepare a vector, which contained gene fragments coding IgG1Fc chimera protein of the soluble human Serrate-1. Finally, this vector was digested by EcoRI and MluI, and splitted about 4400 bp gene fragment was ligated to pMKITNeo to construct the expression vector. This vector was designated as pHSEXIg.

9) Expression Vector of Full Length Human Serrate-1 Protein (HSF)

The cDNA coding polypeptide from No. 1 to 1187 of amino acid sequence in the sequence listing, SEQ ID NO: 7 was ligated with expression vector pMKITNeo containing SRα promoter and neomycin resistance gene to prepare expression vector.

For preparation of the full length expression vector about 900 bp splitted gene fragment from pBS/Eco-Serrate-1 digested by restriction enzyme EcoRI and BglII, and pUCSR-1 digested by the same restriction enzyme were ligated, and a vector pUC/Eco-Serrate-1 coding full length gene of human Serrate-1 was prepared.

In order to add the termination codon to the site after Val at No.1187 in the sequence listing, SEQ ID NO: 7, and further add the restriction enzyme MluI site, using the Mutagenesis Kit, the termination codon and MluI site were added to the C-terminal using oligonucleotides having gene sequence in the sequence listing, SEQ ID NO: 37 and SEQ ID NO: 38 as primers and the pBS/Eco-Serrate-1 as a template. The resulting vector was digested by EcoRI and MulI, and about 3700 bp splitted gene fragments were ligated in pMKITNeo, which was treated by the same restriction enzyme, to construct the expression vector. This vector was designated as pHSF.

10) Expression Vector of FLAG Chimera Protein of Full Length Human Serrate-1 (HSFLAG)

The cDNA coding chimera protein, to which cDNA coding FLAG sequence was added in the C-terminal of polypeptide from No. 1 to 1187 of amino acid sequence in the sequence listing, SEQ ID NO: 7, was ligated to the expression vector pMKITNeo containing SRα promoter and neomycin resistance gene to prepare the expression vector.

In order to add FLAG sequence in the C-terminal the termination codon and further restriction enzyme MluI site, setting oligonucleotides having gene sequence in the sequence listing, SEQ ID NO: 39 and SEQ ID NO: 38 as primers, using pBS/Eco-Serrate-1 as a template a gene coding FLAG sequence, the termination codon and the MluI site were added in the C-terminal as same as similar manner. This vector was digested by EcoRI and MluI, and about 3700 bp splitted gene fragments were ligated to the similarly restriction enzyme treated pMKITNeo to construct the expression vector. This vector was designated as pHSFLAG.

Example 7

Expression and Gene Transfer of the Expression Vectors into Cells

The expression vectors prepared in Examples 5 and 6 were transduced into COS-7 cell (obtained from RIKEN Cell Bank, Physical and Chemical Research Institute, Japan, RCB0539).

Cell culture before gene transduction was performed by culturing in D-MEM (Dulbecco modified Eagle's medium, GIBCO-BRL Inc., U.S.A.) 10% FCS. On a day before gene transduction, medium of cells was changed to set cell counts $5\times10^5$ cells/ml and cultured for overnight. On the day of gene transduction, cells were sedimented by centrifugation, centrifugally washed twice with PBS(−) and prepared the cells to $1\times10^7$ cells/ml in 1 mM $MgCl_2$ and PBS(−). Gene transfer was performed by electroporation using gene transduction device Gene-pulsar (Bio-Rad Inc., U.S.A.). The above cell suspension 500 µl was collected in the cell for electroporation (0.4 cm), added expression vector 20 µg, and allowed to stand in ice for 5 minutes. Electroporation was performed under the condition 3 µF. 450 V twice, during the twice electroporation cell mixture was allowed to stand at room temperature. After 5 minutes stayed in ice, cells were spread in the culture medium, diameter 10 cm previously added 10 ml of medium, and cultured at 37° C. in 5% carbon dioxide incubator.

The next day, the culture supernatant solution was removed, washed the cells adhered to the dish twice with PBS(−) 10 ml. In case of expression vector pHDEX, pHDEXFLAG, pHDEXIg, pHSEX, pHSEXFLAG,and pHSEXIg, serum-free D-MEM 10 ml was added and cultured for 7 days. Culture supernatant solution was recovered and was replaced the buffer to PBS(−) by Centricon 30 (Amicon Inc., U.S.A.) and simultaneously the solution was concentrated to 10-fold to obtain cell culture supernatant solution.

In case of pHDF, pHDFLAG, pHSF,and pHSFLAG, medium was changed by D-MEM containing 10% FCS, and cultured further 3 days to prepare cell lysate. Thus, $2 \times 10^6$ cells were suspended in the cell lysis buffer [50 mM Hepes (pH 7.5), 1% Triton X100, 10% glycerol, 4 mM EDTA, 50 µg/ml Aprotinin, 100 µM Leupeptin, 25 µM Pepstatin A and 1 mM PMSF] 200 µl, allowed to stand in ice for 20 minutes and centrifuged at 14000 rpm for 20 minutes to remove supernatant solution to obtain cell lysate.

Expression of proteins were detected by Western blotting.

Concentrated cultured supernatants or cell lysates were subjected to SDS-PAGE using an electrophoresis tank and polyacrylamide gel for SDS-PAGE (gradient gel 5–15%) (ACI Japan Inc., Japan) according to the manufacturer's construction. Samples were prepared by treatment in boiling water for 5 min. with 2-mercaptoethanol (2-ME) for reduction, and non-reduced condition without taking the above treatment. As a marker, Rainbow Marker (high molecular weight, Amersham Inc.) was used. Sample buffer solution and electrophoresis buffer were prepared with reference to the attached leaflet. When the SDS-PAGE was finished, acrylamide gel was transcribed to PVDF membrane filter (BioRad Inc., U.S.A.) using the Mini Trans Blot Cell (Bio-Rad Inc.).

The thus prepared filter was shaken overnight at 4° C. in the Blockace (Dainippon Pharm. Co., Japan), TBS-T [20 mM Tris, 137 mM NaCl (pH 7.6) and 0.1% Tween 20] to blocking. According to the explanation of the attached leaflet of ECL Western blotting detection system (Amersham Inc., U.S.A.); in case that the objective protein was human Delta-1 origin, anti-human Delta-1 mouse monoclonal antibody described in Example 9 was used as primary antibody; in case that protein was human Serrate-1 origin, anti-human Serrate-1 mouse monoclonal antibody described in Example 9 was used as primary antibody; and in case that protein was FLAG chimera, anti-FLAG M2 mouse monoclonal antibody (Eastman Kodak, U.S.A.) was used as primary antibody, and peroxidase labeled anti-mouse Ig sheep antibodies (Amersham Inc., U.S.A.) was reacted. In case of IgG chimera, peroxidase labeled anti-human Ig sheep antibodies (Amersham Inc., U.S.A.) was reacted.

Reaction time for antibodies was 1 hour at room temperature, and at an interval of each reaction, washing was performed by shaking in TBS-T at room temperature for 10 minutes for three times. After the final washing, the filter was immersed in the reaction solution of ECL-Western blotting detection system (Amersham Inc., U.S.A.) for 5 minutes, and wrapped in polyvinylidene chloride wrap to expose X-ray film.

As the result, in the sample with treatment of reduction, the bands showing protein obtained by transduction of pHDEX and pHDEXFLAG was detetcd about 65 kD ; protein obtained by transduction of pHDEXIg was detected about 95 kD, and protein obtained by transduction of pHDF and pHDFLAG was detected about 85 kD. In the non-reduced sample, the bands showing protein obtained by transduction of pHDEXIg was detected slightly smeared bands at 120 kD to 200 kD, mainly about 180 kD, which showed about 2-fold of the reduction stage, consequently, dimer was formed.

And also, in the sample with treatment of reduction, the bands showing protein obtained by transduction of pHSEX and pHSEXFLAG was detected about 140 kD; protein obtained by transduction of pHSEXIg was detected about 170 kD, and protein obtained by transduction of pHSF and pHSFLAG was detected about 150 kD. In the non-reduced sample, the bands showing protein obtained by transduction of pHSEXIg was detected slightly smeared bands at 250 kD to 400 kD, mainly about 300 kD, which showed about 2-fold of the reduction stage, consequently, dimer was formed.

In these experiments, however cell lysate and cultured supernatant of COS-7 cells, to which pMKITNeo vector was transduced as a control was tested., no bands reacted against anti-human Delta-1 mouse monoclonal antibody, anti-human Serrate-1 mouse monoclonal antibody, anti-FLAG antibody, and anti-human Ig antibody were detected.

Therefore, this ten-expression vector can produce the objective polypeptides.

Example 8

Purification of Soluble Human Delta-1 and Human Serrate-1 Proteins of Gene Transduction Cells Cultured supernatant of COS-7 cells consisting of HDBX-FLAG, HDBXIg, HSEXFLAG and HSEXIg, all of which expression was detected by a method in Example 7, were prepared on large scale, and each chimera protein was purified by affinity column chromatography.

In case of HDEXFLAG and HSEXFLAG, 2 liter of the cultured supernatant obtained by the method in Example 7 was passed through a column packed with Anti-FLAG M2 Affinity Gel (Eastman Kodak, U.S.A.). The chimera protein was adsorbed in a column by a reaction of affinity of anti-FLAG antibody of the gel and FLAG sequence of the chimera protein. Column, inner diameter 10 mm, disposable column (BioRad Inc., U.S.A.) was used with packing the above gel 5 ml. A circulation system consisting of medium bottle→column→peristaltic pump medium bottle was set up. The circulation was run by a flow 1 ml/min. for 72 hours. Thereafter the column was washed with PBS (−) 35 ml and eluted by 0.5 M Tris-glycine (pH 3.0) 50 ml. The eluate of 25 fractions, each 2 ml, was collected into the tube, and each fraction was neutralized by 200 µl of 0.5 M Tris-HCl (pH 9.5) previously added in each tube.

The eluate fraction, each 10 µl of the secretor FLAG chimera protein which was purified by the above method was subjected to reduction treatment described in Example 7. SDS-PAGE electrophoresis by 5–10% gradient polyacrylamide gel was performed. After finishing the electrophoresis, silver staining was conducted by using Wako silver stain kit II (Wako Pure Chemicals, Japan) according to the explanation of the attached leaflet. Fractions from No. 4 to 8 showed detectable bands in HSFLAG. The size is identical with the result of Western blotting of anti-FLAG antibody obtained in Example 6 in both of HDEXFLAG and HSEX-FLAG. Therefore, purified HDEXFLAG and HSEFLAG were obtained.

In the IgG1Fc chimera protein, i. e. HDEXIg and HSEXIg, the cultured supernatant solution 2 liter was adsorbed in Protein A Sepharose colulnn (Pharmacia Inc., Sweden) according to the same method as of FLAG chimera protein to collect the eluate fractions. Using a part of eluate as same as in FLAG chimera protein, a determination of the eluate fraction, identification of the size and detection of the purity were performed by SDS-PAGE electrophoresis and silver staining in the reduced condition. Therefore, the eluate fraction from No. 4 to 15 were the detected bands. The size thereof is identical with the result of Western blotting using anti-human Ig antibody in both of HDEXIg and HSEXIg. Therefore, purified HDEXIg and HSEXIg were obtained.

Example 9

Preparation of Antibodies Recognizing Human Delta-1 and Human Serrate-1

HDEXFLAG and HSEXFLAG, purified by the method in Example 8, were used as immunogen, and rabbits were immunized. After assaying antibody titer, whole blood was collected and serum was obtained. Anti-human Delta-1 rabbit polyclonal antibody and anti-human Serrate-1 rabbit polyclonal antibody were purified by using the econopack serum IgG purification kit (BioRad Inc., U.S.A. ) with reference to the attached explanation leaflet.

HDEXFLAG and HSEXFLAG purified by a method described in Example 8 were used as Immunogens, and mouse monoclonal antibodies were prepared according to the explanation of the textbook. The purified HDEXFLAG or HSEXFLAG was administered in Balb/c mice (Nippon SLC CO., Japan) separately, 10 μg/mouse, immunized intracutaneously and subcutaneously. After second immunization increased serum titer was confirmed by collecting blood ophthalmologically, the third immunization was performed. Subsequently, the spleen of mice was collected and fused with mouse myeloma cells P3×63Ag8 (ATCC TIB9) using polyethylene glycol. Hybridoma was selected by HAT medium (Immunological and Biological Research Institute, Japan) , and the hybridoma strains which produced antibody specifically recognizing extracellular region of human Delta-1 or human Serrate-1 in the medium, were isolated by enzyme immunoassay. The hybridoma strains producing mouse monoclonal antibody, which specifically recognized human Delta-1 or human Serrate-1, were established.

Anti-human Delta-1 monoclonal antibody and anti-human Serrate-1 monoclonal antibody were purified and prepared by using Mab Trap GII (Pharmacia Inc., Sweden) and according to the explanation of the leaflet, from the supernatant of the thus established hybridoma.

Affinity column was prepared by using these monoclonal antibodies. Preparation of the affinity column was performed according to the explanation attached to the CNBr activated Sephadex 4B (Pharmacia Inc., Sweden). A column, 2 cm$^2$×1 cm, containing gel 2 ml. was prepared.

A concentrated solution of the supernatant of the cultured COS-7 cells, to which pHDEX was gene transduced, was passed through the column for which anti-human Delta-1 monoclonal antibody was bound. A concentrated solution of the supernatant of the cultured COS-7 cells, to which pHSEX was gene transduced, was passed through the column, for which anti-human Serrate-1 monoclonal antibody was bound. Each supernatant solution was passed at 20 ml/hr, subsequently PBS (−) 15 ml was passed at the same flow rate and washed the column. Finally, the products were eluted by a mixture of 0.1 M sodium acetate and 0.5 M NaCl (pH 4.0). The eluate, each 1 ml fraction, was collected, and was neutralized by adding 1M Tris-HCl (pH 9.1) 200 μl for each fraction.

SDS-PAGE of each purified protein was conducted under reduced condition according to the method described in Example 8, followed by silver staining and Western blotting to estimate molecular weight. HDEX, about 65 kD, was purified from concentrated supernatant of the cultured COS-7 cells, to which pHDEX was gene transduced, and HDSEX, about 140 kD, was purified from concentrated supernatant of the cultured COS-7 cells, to which pHSEX was gene transduced. Consequently, human Delta-1 and human Serrate-1 can be purified by these affinity columns.

Example 10

Effects of HDEXIg and HSEXIg to Colony Formation of Blood Undifferentiated Cells In order to observe physiological action of HDEXIg and HSEXIg on blood undifferentiated cells, CD34 positive cells were cultured in the serum-free semi solid medium in the presence of HDEXIg and HSEXIg and known cytokines, and number of colony forming cells were observed.

Human umbilical cord blood or adult human normal bone marrow blood was treated by the silica solution (Immunological and Biological Research Institute, Japan) according to the attached explanation leaflet. Thereafter the low density cellular fraction (<1.077 g/ml) was fractionated by densitometric centrifugation of Ficoll pack (Pharmacia Inc., Sweden) to prepare mononuclear cells. CD34 positive cells of human umbilical cord blood or human normal bone marrow blood was isolated from the mononuclear cells.

Separation of CD34 positive cells was performed by using Micro-Selector System (AIS Inc., U.S.A.) or Dynabeads M-450 CD34 and DETACHa-BEADS CD34 (Dynal Inc., Norway) according to attached explanation leaflets. After separation, the purity was measured as follows. Cells were stained by FITC labeled CD34 antibody HPCA2 (Beckton-Deckinson Inc., U.S.A.) and examined by a flow-cytometer (FACSCalibur, Beckton-Deckinson, U.S.A.). Purity above 85% was confirmed for use.

The thus isolated CD34 positive cells were suspended homogeneously to form 400 cells/ml of the medium hereinbelow, and spread in the 35 mm dish (Falcon Inc., U.S.A.), then cultured for 2 weeks in carbon dioxide incubator at 37° C. under 5% carbon dioxide, 5% oxygen, 90% nitrogen and 100% humidity. The formed blood colonies were counted under the invert microscope.

A medium used is α-medium (GIBCO-BRL, U.S.A.), containing 2% deionized bovine serum albumin (BSA, Sigma, U.S.A.), 10 μg /ml human insulin (Sigma, U.S.A.) 200 μg/ml transferrin (Sigma, U.S.A.). $10^{-5}$M 2-mercaptoethanol (Nakarai Tesk Co., Japan), 160 μg/ml soybean lectin (Sigma, U.S.A.), 96 μg/ml cholesterol (Sigma, U.S.A. ) and 0.9% methylcellulose (Wako Pure Chemicals, Japan).

To the above medium under the following three conditions of cytokines, human Delta-1 extracellular Ig chimera protein (HDEXIg) or human Serrate-1 extracellular Ig chimera protein (HSEXIg) were added to the final concentration of 1 μg/ml. For control, human IgG1 (Ahens Research and Technology Inc., U.S.A.) was added with the same concentration in order to observe effect of IgGFc region.

Conditions of cytokines are as follows.
1 : 100 µg/ml, human SCF(Intergen Inc., U.S.A.), 10 ng/ml humnan IL-3 (Intergen Inc., U.S.A.), 100 ng/ml human IL-6 (Intergen Inc., U.S.A. )
2 : 100 ng/ml human SCF, 10 ng/ml human IL-3, 4 ng/ml human thrombopoietin (Pepro Tech Inc., U.S.A.)
3 : 100 ng/ml human SCF, 10 ng/ml human IL-3, 100 ng/ml human IL-6 2 U/ml Epo (Chugai Seiyaku Co., Japan) 10 ng/ml human G-CSF (Chugai Seiyaku Co., Japan)

Results are shown in FIG. 2. In FIG. 2, A is a case of human Delta-1 extracellular Ig chimera protein (HDEXIg), and B is a case of human Serrate-1 extracellular Ig chimera protein (HSEXIg). For A and B, each different origin human umbilical cord blood CD34 positive cell was used. The vertical axis:number of colonies. White:control, black:HDEXIg or HSEXIg. Both HDEXIg and HSEXIg have suppressive action of colony formation. No differences of the activities on the types of colonies were noted. Therefore, the molecular of the present invention has suppressive action for colony formation against colony forming cells of blood undifferentiated cells, i.e. diferentiation-suppressive action. Comparison with or without SCF on the activity indicated that the suppressive action tended to occur only in the presence of SCF.

Dose-dependent manner of the activity was studied. Comparison with dimer HSEXIg and monomer HSEXFLAG was performed. Result is shown in FIG. 3. Concentration in this case is indicated as molar concentration. For comparison with dimer and monomer, dimer HSEXIg was indicated by exact two molar concentrations, and was plotted equivalent molar concentration of the human Serrate-1. Vertical axis indicates colony forming counts and horizontal axis indicates molar concentration. Colony forming counts without Notch ligand were plotted on the vertical axis in the zero concentration. For comparison, colony forming counts of human IgG1 1 µg/ml, was about 100 colonies.

This result indicated that HSEXIg and HSEXFLAG suppressed colony formation in dose-dependent manner. Activity of dimer HSEXIg was stronger than the monomer. A monomer HSEXFLAG showed stimulative action for colony formation in the low concentration area.

Example 11

Actions of HDEXIg and HSEXIg on Long Term Liquid Culture of Colony Forming Blood Undifferentiated Cells For observing physiological action of HDEXIg and HSEXIg on the blood undifferentiated cells, umbilical cord blood CD34 positive cells were culture for long term in the serum-free liquid medium in the presence of HDEXIg or HSEXIg and known cytokines, and numbers of colony forming cells were observed.

The umbilical cord blood mononuclear CD34 positive cells separated by a method described in Example 10 were liquid cultured at 1000 cells/well in the 24 well cell culture plate (Falcon Inc., U.S.A.). Culture was performed at 37° C. in the carbon dioxide incubator under 5% carbon dioxide and 100% humidity. Liquid culture medium was Iscove's modified Dulbecco's medium (IMDM, GIBCO-BRL, U.S.A.) added with 2% BSA, 10 µg/ml human insulin, 200 µg/ml transferrin. 40 µg/ml low density lipoprotein (GIBCO-BRL, U.S.A.), $10^{-5}$ M 2-mercaptoethanol, 50 ng/ml human SCF, 5 ng/ml human IL-3, 10 ng/ml human IL-6, 5 ng/ml human GM-CSF (Intergen Inc., U.S.A.), and 3 U/ml Epo. If necessary,XDEXIg-$^{500}$ ng HSEX1 g or 50 ng/ml MIP-1α Intergen Inc., U.S.A.) was added. The medium was added 1 ml/well and half of the medium was changed three times in a week. After culturing 2, 4, 6 and 8 weeks, all cells were collected from wells by using cell scraper in 1.5 ml micro tube. Cells were precipitated by centrifugation and resuspended in a fresh IMDM 1 ml, counted the cell counts by using hemocytometer, and in 5000 cells/ml, blood cell colony forming assay was performed.

Blood cell colony forming assay was performed using the Iscove's methylcellulose complete ready mix (Stem Cell Technologies Inc., Canada), and each 1 ml was inoculated in two plates of 35 mm dish (Falcon Inc., U.S.A.) and incubated for 2 weeks in the carbon dioxide incubator. Blood colonies were counted CFU-GM and BFU-E in the invert microscope, and total was counted as CFU-C. CFU-C counts and cell counts obtained by hemocytometer were multiplied to obtain CFU-C count/1000 cells inoculated in the liquid culture.

In Table 1 result of HDEXIg and in Table 2, result of HSEXIg are shown. Experiments were conducted at n=3, values obtained were shown by (mean±SD). In the table, ND means no detection of colony.

TABLE 1

Colony forming cell maintenance action in the long-term liquid culture of human Delta-1 of the present invention

| | Cytokines | | |
|---|---|---|---|
| Week | — | MIP-1 α | HDEXIg |
| 0 | 69 ± 9 | 68 ± 9 | 68 ± 9 |
| 2 | 1440 ± 120 | 720 ± 110 | 1280 ± 230 |
| 4 | 340 ± 40 | 420 ± 80 | 410 ± 90 |
| 6 | 28 ± 6 | 96 ± 17 | 290 ± 60 |
| 8 | ND | ND | 88 ± 13 |

TABLE 2

Colony forming cell maintenance action in the long-term liquid culture of human Serrate-1 of the present invention

| | Cytokines | | |
|---|---|---|---|
| Week | — | MIP-1 α | HSEXIg |
| 0 | 68 ± 9 | 68 ± 9 | 68 ± 9 |
| 2 | 1440 ± 120 | 720 ± 110 | 1360 ± 280 |
| 4 | 340 ± 40 | 420 ± 80 | 560 ± 70 |
| 6 | 28 ± 6 | 96 ± 17 | 220 ± 50 |
| 8 | ND | ND | 130 ± 50 |

CFU-C could only be observed until $6^{th}$ week of cultivation under the condition without cytokines for maintaining undifferentiated condition, and under the condition with MIP-1α. It could be observed at $8^{th}$ week in the presence of HDEXIg or HSEXIg. In comparison with MIP-1α and HDEXIg and HSEXIg, MIP-1α strongly suppressed colony formation at 2 weeks of culture, however no suppression in HDEXIg and HSEXIg were observed. In maintenance of CFU-C counts at 6 and 8 weeks of culture, HDBXIg and HSEXIg were superior.

Example 12

Effects of HDEXIg and HSEXIg on Liquid Culture of Blood Undifferentiated Cell LTC-IC In order to observing physiological action of HDEXIg and HSEXIg on the blood undifferentiated cells, umbilical cord blood CD34 positive cells were cultured for two weeks in the serum-free liquid medium in the presence of HDEXIg or HSEX1g and known cytokines, and numbers of LTC-IC, which was thought to be most undifferentiated blood cells at present were observed.

The umbilical cord blood monocyte CD34 positive cells, 100000 to 20000 cells, separated by a method described in Example 10 were cultured in the following medium for 2 weeks. Numbers of LTC-IC in 4 experimental groups, which include a group before cultivation, a group of HDEXIg, a group of HSEXIg and a control group, were determined. Media used in liquid culture medium were α-medium added with 2% BSA, 10 µg/ml human insulin, 200 µg/ml transferrin, 40 µg/ml low density lipoprotein, and $10^{-5}$M 2-mercaptoethanol, further added with 100 ng/ml human SCF, 10 ng/ml human IL-3, and 100 ng/ml human IL-6. HDEXIg or HSEXIg 1 µg/ml were added to the above medium. In the control group, human IgG1 was added in the equal concentration.

Preparation of human bone marrow stromal cell layer used for LTC-IC, and quantitative assay of frequency of LTC-IC by a limit dilution were performed according to a method of Sutherland et al. (Blood, 74, 1563-, 1989 and Proc, Natl. Acad. Sci, USA, 87, 3584-, 1990)

The bone marrow mononuclear cells, $1-2\times10^7$ cells, obtained in Example 10 before the separation and without the silica solution treatment, were cultured in LTC medium (MyeloCul, Stem Cell Technologies Inc., Canada) 5 ml added with hydrocortisone 1 µM (Upjohn Japan Co., Japan ) in T-25 flask (Falcon Inc., U.S.A.) at 37° C. under 5% carbon dioxide and 100% humidity in the carbon dioxide incubator. Culture was conducted until the adhesive cell layers of the stromal cell formation spread more than 80% of the bottom area of the culture. Detachment of the cell layer was performed by treating with EDTA solution (Cosmobio Co., Japan). Cells were plated in the 96 well plate (Beckton-Deckinson Inc., U.S.A.), about $2\times10^4$ cells/well and re-cultivation was continued in the same medium. X-ray, 15 Gy, 250 KV peak was irradiated after reconstituted stromal cell layer. Growth of stromal cells was stopped and blood cells in the stromal cells were removed by this treatment. The thus prepared stromal cells were used as stromal cell layer for the experiments.

In the assay of LTC-IC, cell counts in each group were adjusted within the ranges of 25–400 cells/well for CD34 positive cells before the cultivation, and 625–20000 cells/well for the cells after the cultivation, and cells were diluted for six step-dilution within these ranges. Each dilution step of cells was co-cultured with the above stromal cell layer in the 96 well plate, for 16 wells/cells of one dilution step. Culture was performed in the same medium as used in stromal formation, at 37° C. under 5% carbon dioxide and 100% humidity in the carbon dioxide gas incubator for 5 weeks. Cells in suspension and in attachment after cultivation were recovered in each well. Collected cells were transferred to the semi-solid culture medium consisting of α-medium added with 0.9% methylcellulose, 30% fetal calf serum (FCS, ICN Biomedical Japan), 1% BSA, $10^{-5}$M 2-mercaptoethanol, 100 ng/ml human SCF, 10 ng/ml human IL-3, 100 ng/ml human IL-6, 2U/ml Epo and 10 ng/ml human G-CSF. After 2 weeks of cultivation, colony forming cells were detected as the same was as described in Example 10 and 11, and numbers of well, in which colony forming cells were found, were detected. Incidence of LTC-IC was calculated according to the method of Taswell et al. (J. Immunol. 126, 1614-, 1981) based on the above data.

Graph used for calculation is shown in FIG. 4. In FIG. 4, calculation curves after liquid culture is shown. A vertical axis shows ratio of well for no colonies were observed, and a horizontal axis shows number of cells/well. In each experimental group, numbers of well, for which colonies were not observed, and numbers of cells were plotted, then regression curve was calculated by the least square method. Number of cells corresponding to number of 0.37 (a reciprocal of a base of natural logarithm) for which colonies did not appeared, was calculated. A reciprocal of that number of cells is a frequency of LTC-IC. Further, absolute number of LTC-IC was calculated from initial number of cells and frequency of LTC-IC.

The result indicated that 243 LTC-IC were found in 25000 cells before the liquid culture. In the control group number of cells during 2 weeks of cultivation increased to 1,510,000 cells, and LTC-IC was decreased to 49 cells. However, culturing with human Delta-1, i.e. HDEXIg or human Serrate-1, i.e. HSEXIg, numbers of cells were maintained in 1,310,000 and 1,140,000, respectively, and numbers of LTC-IC were slightly decreased to 115 and 53. Consequently, polypeptide of the present invention, especially human Delta-1 could have an activity for maintenance of number of LTC-IC in the liquid culture.

Example 13

Binding of HDEXIg and HSEXIg for Blood Cells

Binding of Notch ligands with various blood cells was studied using specific binding of Notch ligands to Notch receptors.

Blood cell lines tested were Jurkat (ATCC TIB-152), Namalwa (ATCC CRL-1432), HL-60 (ATCC CRL-1964), K562 (ATCC CCL-243), THO-1 (ATCC TIB-2 02), UT-7 (Komatsu et al., Cancer Res.,51, 341–348, 1991), Mo7e (Avanzi et al. Br. J. Haematol., 69, 359-, 1988) and CMK (Sato et al. Exp. Hematol., 15, 495–502, 1987). Culturing media for these cells were found in the reference or ATCC CELL LIMES & HYBRIDOMAS, $8^{th}$ Ed. (1994).

Cells, $1\times10^6$ cells, were suspended in Hank's balanced salt solution containing 2% FCS and 10 mM Hepes. HDEXIg or HSEXIg 1 µg/ml were added therein and allowed to stand at 4° C. for overnight. Cells were washed twice with the Hank's solution. PE labeled sheep anti-human IgG monoclonal antibody 1 µg/ml was added, allow to stand in ice-cooling for 30 minutes, washed twice with the Hank's solution, and suspended in the Hank's solution 1 ml. Analysis was performed using the flow cytometer (FACS-Calibur). Control groups were used with human IgG1 staining in place of HDEXIg or HSEXIg staining.

Results are shown in FIG. 5. A vertical axis indicates cell counts and a horizontal axis indicates fluorescence intensity. Staining with HDEXIg or HSEXIg is shown by solid line and control, a staining with human IgG1 is shown by a broken line. In FIG. 5, the left column shows HDEXIg and the right column shows HSEXIg. As shown in FIG. 5, results indicate that Jurkat: reacted, Namalwa: non-reacted, HL-60: non-reacted, K562: non-reacted, THP-1: non-reacted, UT-7: reacted, Mo7e: non-reacted and CMK: reacted. Since the same results in HDEXIg and HSEXIg were obtained, both recognized the identical molecule and these cells can be differentiated.

Effect of the Invention

Notch ligand molecules of the present invention can be used for maintenance of undifferentiated-suppressive substances, and in the preparation of pharmaceuticals.

The invention claimed is:

1. A method for culturing blood precursor cells and/or hematopoietic stem cells in vitro, comprising contacting said cells in vitro with Stem Cell Factor (SCF) and a serrate-1 peptide, and wherein said peptide comprises SEQ ID NO: 5.

2. A method for culturing blood precursor cells and/or hematopoietic stem cells in vitro, comprising contacting said cells in vitro with Stem Cell Factor (SCF) and a serrate-1 peptide, and wherein said peptide comprises SEQ ID NO: 6.

3. A method for culturing blood precursor cells and/or hematopoietic stem cells in vitro, comprising contacting said cells in vitro with Stem Cell Factor (SCF) and a serrate-1 peptide, and wherein said peptide comprises SEQ ID NO: 7.

4. A method for culturing CD 34 positive blood precursor cells in vitro, comprising contacting said cells in vitro with Stem Cell Factor (SCF) and a serrate-1 peptide, and wherein said peptide is selected from the group consisting of SEQ ID NO: 5, SEQ ID NO: 6, and SEQ ID NO: 7.

5. The method according to claim 4, wherein said peptide is SEQ ID NO: 5.

6. The method according to claim 4, wherein said peptide is SEQ ID NO: 6.

7. The method according to claim 4, wherein said peptide is SEQ ID NO: 7.

* * * * *

SEQUENCE LISTING

<160> NUMBER OF SEQ ID NOS: 48

<210> SEQ ID NO 1
<211> LENGTH: 43
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Unknown amino acid
<220> FEATURE:
<221> NAME/KEY: MOD_RES
<222> LOCATION: (7)..(9)
<223> OTHER INFORMATION: Unknown amino acid
<220> FEATURE:
<221> NAME/KEY: MOD_RES
<222> LOCATION: (11)..(13)
<223> OTHER INFORMATION: Unknown amino acid
<220> FEATURE:
<221> NAME/KEY: MOD_RES
<222> LOCATION: (20)
<223> OTHER INFORMATION: Unknown amino acid
<220> FEATURE:
<221> NAME/KEY: MOD_RES
<222> LOCATION: (24)..(25)
<223> OTHER INFORMATION: Unknown amino acid
<220> FEATURE:
<221> NAME/KEY: MOD_RES
<222> LOCATION: (27)..(29)
<223> OTHER INFORMATION: Unknown amino acid
<220> FEATURE:
<221> NAME/KEY: MOD_RES
<222> LOCATION: (31)..(33)
<223> OTHER INFORMATION: Unknown amino acid
<220> FEATURE:
<221> NAME/KEY: MOD_RES
<222> LOCATION: (35)..(36)
<223> OTHER INFORMATION: Unknown amino acid
<220> FEATURE:
<221> NAME/KEY: MOD_RES
<222> LOCATION: (39)
<223> OTHER INFORMATION: Unknown amino acid
<220> FEATURE:
<221> NAME/KEY: MOD_RES
<222> LOCATION: (41)..(42)
<223> OTHER INFORMATION: Unknown amino acid

<400> SEQUENCE: 1

Cys Xaa Xaa Xaa Tyr Tyr Xaa Xaa Xaa Cys Xaa Xaa Xaa Cys Arg Pro
 1               5                  10                  15

Arg Asx Asp Xaa Phe Gly His Xaa Xaa Cys Xaa Xaa Xaa Gly Xaa Xaa
                20                  25                  30

Xaa Cys Xaa Xaa Gly Trp Xaa Gly Xaa Xaa Cys
        35                  40

<210> SEQ ID NO 2
<211> LENGTH: 200
<212> TYPE: PRT
<213> ORGANISM: Homo sapiens

<400> SEQUENCE: 2

Ser Gly Val Phe Glu Leu Lys Leu Gln Glu Phe Val Asn Lys Lys Gly
 1               5                  10                  15

Leu Leu Gly Asn Arg Asn Cys Cys Arg Gly Gly Ala Gly Pro Pro Pro
                20                  25                  30

Cys Ala Cys Arg Thr Phe Phe Arg Val Cys Leu Lys His Tyr Gln Ala
        35                  40                  45

Ser Val Ser Pro Glu Pro Pro Cys Thr Tyr Gly Ser Ala Val Thr Pro

```
            50                  55                  60
Val Leu Gly Val Asp Ser Phe Ser Leu Pro Asp Gly Gly Ala Asp
 65                  70                  75                  80

Ser Ala Phe Ser Asn Pro Ile Arg Phe Pro Phe Gly Phe Thr Trp Pro
                 85                  90                  95

Gly Thr Phe Ser Leu Ile Ile Glu Ala Leu His Thr Asp Ser Pro Asp
                100                 105                 110

Asp Leu Ala Thr Glu Asn Pro Glu Arg Leu Ile Ser Arg Leu Ala Thr
                115                 120                 125

Gln Arg His Leu Thr Val Gly Glu Thr Ser Gln Asp Leu His Ser
            130                 135                 140

Ser Gly Arg Thr Asp Leu Lys Tyr Ser Tyr Arg Phe Val Cys Asp Glu
145                 150                 155                 160

His Tyr Tyr Gly Glu Gly Cys Ser Val Phe Cys Arg Pro Arg Asp Asp
                165                 170                 175

Ala Phe Gly His Phe Thr Cys Gly Glu Arg Gly Glu Lys Val Cys Asn
                180                 185                 190

Pro Gly Trp Lys Gly Pro Tyr Cys
            195                 200

<210> SEQ ID NO 3
<211> LENGTH: 520
<212> TYPE: PRT
<213> ORGANISM: Homo sapiens

<400> SEQUENCE: 3

Ser Gly Val Phe Glu Leu Lys Leu Gln Glu Phe Val Asn Lys Gly
 1               5                  10                  15

Leu Leu Gly Asn Arg Asn Cys Cys Arg Gly Gly Ala Gly Pro Pro
                20                  25                  30

Cys Ala Cys Arg Thr Phe Phe Arg Val Cys Leu Lys His Tyr Gln Ala
                35                  40                  45

Ser Val Ser Pro Glu Pro Pro Cys Thr Tyr Gly Ser Ala Val Thr Pro
             50                  55                  60

Val Leu Gly Val Asp Ser Phe Ser Leu Pro Asp Gly Gly Ala Asp
 65                  70                  75                  80

Ser Ala Phe Ser Asn Pro Ile Arg Phe Pro Phe Gly Phe Thr Trp Pro
                 85                  90                  95

Gly Thr Phe Ser Leu Ile Ile Glu Ala Leu His Thr Asp Ser Pro Asp
                100                 105                 110

Asp Leu Ala Thr Glu Asn Pro Glu Arg Leu Ile Ser Arg Leu Ala Thr
                115                 120                 125

Gln Arg His Leu Thr Val Gly Glu Trp Ser Gln Asp Leu His Ser
            130                 135                 140

Ser Gly Arg Thr Asp Leu Lys Tyr Ser Tyr Arg Phe Val Cys Asp Glu
145                 150                 155                 160

His Tyr Tyr Gly Glu Gly Cys Ser Val Phe Cys Arg Pro Arg Asp Asp
                165                 170                 175

Ala Phe Gly His Phe Thr Cys Gly Glu Arg Gly Glu Lys Val Cys Asn
                180                 185                 190

Pro Gly Trp Lys Gly Pro Tyr Cys Thr Glu Pro Ile Cys Leu Pro Gly
            195                 200                 205

Cys Asp Glu Gln His Gly Phe Cys Asp Lys Pro Gly Glu Cys Lys Cys
210                 215                 220
```

```
Arg Val Gly Trp Gln Gly Arg Tyr Cys Asp Glu Cys Ile Arg Tyr Pro
225                 230                 235                 240

Gly Cys Leu His Gly Thr Cys Gln Gln Pro Trp Gln Cys Asn Cys Gln
            245                 250                 255

Glu Gly Trp Gly Gly Leu Phe Cys Asn Gln Asp Leu Asn Tyr Cys Thr
        260                 265                 270

His His Lys Pro Cys Lys Asn Gly Ala Thr Cys Thr Asn Thr Gly Gln
    275                 280                 285

Gly Ser Tyr Thr Cys Ser Cys Arg Pro Gly Tyr Thr Gly Ala Thr Cys
290                 295                 300

Glu Leu Gly Ile Asp Glu Cys Asp Pro Ser Pro Cys Lys Asn Gly Gly
305                 310                 315                 320

Ser Cys Thr Asp Leu Glu Asn Ser Tyr Ser Cys Thr Cys Pro Pro Gly
            325                 330                 335

Phe Tyr Gly Lys Ile Cys Glu Leu Ser Ala Met Thr Cys Ala Asp Gly
        340                 345                 350

Pro Cys Phe Asn Gly Gly Arg Cys Ser Asp Ser Pro Asp Gly Gly Tyr
    355                 360                 365

Ser Cys Arg Cys Pro Val Gly Tyr Ser Gly Phe Asn Cys Glu Lys Lys
370                 375                 380

Ile Asp Tyr Cys Ser Ser Ser Pro Cys Ser Asn Gly Ala Lys Cys Val
385                 390                 395                 400

Asp Leu Gly Asp Ala Tyr Leu Cys Arg Cys Gln Ala Gly Phe Ser Gly
            405                 410                 415

Arg His Cys Asp Asp Asn Val Asp Asp Cys Ala Ser Ser Pro Cys Ala
        420                 425                 430

Asn Gly Gly Thr Cys Arg Asp Gly Val Asn Asp Phe Ser Cys Thr Cys
    435                 440                 445

Pro Pro Gly Tyr Thr Gly Arg Asn Cys Ser Ala Pro Val Ser Arg Cys
450                 455                 460

Glu His Ala Pro Cys His Asn Gly Ala Thr Cys His Glu Arg Gly His
465                 470                 475                 480

Arg Tyr Val Cys Glu Cys Ala Arg Gly Tyr Gly Gly Pro Asn Cys Gln
            485                 490                 495

Phe Leu Leu Pro Glu Leu Pro Pro Gly Pro Ala Val Val Asp Leu Thr
        500                 505                 510

Glu Lys Leu Glu Gly Gln Gly Gly
    515                 520

<210> SEQ ID NO 4
<211> LENGTH: 702
<212> TYPE: PRT
<213> ORGANISM: Homo sapiens

<400> SEQUENCE: 4

Ser Gly Val Phe Glu Leu Lys Leu Gln Glu Phe Val Asn Lys Lys Gly
1               5                   10                  15

Leu Leu Gly Asn Arg Asn Cys Cys Arg Gly Gly Ala Gly Pro Pro Pro
            20                  25                  30

Cys Ala Cys Arg Thr Phe Phe Arg Val Cys Leu Lys His Tyr Gln Ala
        35                  40                  45

Ser Val Ser Pro Glu Pro Pro Cys Thr Tyr Gly Ser Ala Val Thr Pro
    50                  55                  60

Val Leu Gly Val Asp Ser Phe Ser Leu Pro Asp Gly Gly Gly Ala Asp
65                  70                  75                  80
```

-continued

```
Ser Ala Phe Ser Asn Pro Ile Arg Phe Pro Phe Gly Phe Thr Trp Pro
                85                  90                  95
Gly Thr Phe Ser Leu Ile Ile Glu Ala Leu His Thr Asp Ser Pro Asp
               100                 105                 110
Asp Leu Ala Thr Glu Asn Pro Glu Arg Leu Ile Ser Arg Leu Ala Thr
               115                 120                 125
Gln Arg His Leu Thr Val Gly Glu Glu Trp Ser Gln Asp Leu His Ser
   130                 135                 140
Ser Gly Arg Thr Asp Leu Lys Tyr Ser Tyr Arg Phe Val Cys Asp Glu
145                 150                 155                 160
His Tyr Tyr Gly Glu Gly Cys Ser Val Phe Cys Arg Pro Arg Asp Asp
                   165                 170                 175
Ala Phe Gly His Phe Thr Cys Gly Glu Arg Gly Glu Lys Val Cys Asn
               180                 185                 190
Pro Gly Trp Lys Gly Pro Tyr Cys Thr Glu Pro Ile Cys Leu Pro Gly
               195                 200                 205
Cys Asp Glu Gln His Gly Phe Cys Asp Lys Pro Gly Glu Cys Lys Cys
   210                 215                 220
Arg Val Gly Trp Gln Gly Arg Tyr Cys Asp Glu Cys Ile Arg Tyr Pro
225                 230                 235                 240
Gly Cys Leu His Gly Thr Cys Gln Gln Pro Trp Gln Cys Asn Cys Gln
                   245                 250                 255
Glu Gly Trp Gly Gly Leu Phe Cys Asn Gln Asp Leu Asn Tyr Cys Thr
               260                 265                 270
His His Lys Pro Cys Lys Asn Gly Ala Thr Cys Thr Asn Thr Gly Gln
           275                 280                 285
Gly Ser Tyr Thr Cys Ser Cys Arg Pro Gly Tyr Thr Gly Ala Thr Cys
   290                 295                 300
Glu Leu Gly Ile Asp Glu Cys Asp Pro Ser Pro Cys Lys Asn Gly Gly
305                 310                 315                 320
Ser Cys Thr Asp Leu Glu Asn Ser Tyr Ser Cys Thr Cys Pro Pro Gly
               325                 330                 335
Phe Tyr Gly Lys Ile Cys Glu Leu Ser Ala Met Thr Cys Ala Asp Gly
               340                 345                 350
Pro Cys Phe Asn Gly Gly Arg Cys Ser Asp Ser Pro Asp Gly Gly Tyr
           355                 360                 365
Ser Cys Arg Cys Pro Val Gly Tyr Ser Gly Phe Asn Cys Glu Lys Lys
   370                 375                 380
Ile Asp Tyr Cys Ser Ser Ser Pro Cys Ser Asn Gly Ala Lys Cys Val
385                 390                 395                 400
Asp Leu Gly Asp Ala Tyr Leu Cys Arg Cys Gln Ala Gly Phe Ser Gly
               405                 410                 415
Arg His Cys Asp Asp Asn Val Asp Asp Cys Ala Ser Ser Pro Cys Ala
           420                 425                 430
Asn Gly Gly Thr Cys Arg Asp Gly Val Asn Asp Phe Ser Cys Thr Cys
           435                 440                 445
Pro Pro Gly Tyr Thr Gly Arg Asn Cys Ser Ala Pro Val Ser Arg Cys
   450                 455                 460
Glu His Ala Pro Cys His Asn Gly Ala Thr Cys His Glu Arg Gly His
465                 470                 475                 480
Arg Tyr Val Cys Glu Cys Ala Arg Gly Tyr Gly Gly Pro Asn Cys Gln
               485                 490                 495
```

```
Phe Leu Leu Pro Glu Leu Pro Pro Gly Pro Ala Val Val Asp Leu Thr
            500                 505                 510
Glu Lys Leu Glu Gly Gln Gly Gly Pro Phe Pro Trp Val Ala Val Cys
            515                 520                 525
Ala Gly Val Ile Leu Val Leu Met Leu Leu Gly Cys Ala Ala Val
        530                 535                 540
Val Val Cys Val Arg Leu Arg Leu Gln Lys His Arg Pro Pro Ala Asp
545                 550                 555                 560
Pro Cys Arg Gly Glu Thr Glu Thr Met Asn Asn Leu Ala Asn Cys Gln
                565                 570                 575
Arg Glu Lys Asp Ile Ser Val Ser Ile Gly Ala Thr Gln Ile Lys
            580                 585                 590
Asn Thr Asn Lys Lys Ala Asp Phe His Gly Asp His Ser Ala Asp Lys
            595                 600                 605
Asn Gly Phe Lys Ala Arg Tyr Pro Ala Val Asp Tyr Asn Leu Val Gln
        610                 615                 620
Asp Leu Lys Gly Asp Asp Thr Ala Val Arg Asp Ala His Ser Lys Arg
625                 630                 635                 640
Asp Thr Lys Cys Gln Pro Gln Gly Ser Ser Gly Glu Glu Lys Gly Thr
                645                 650                 655
Pro Thr Thr Leu Arg Gly Gly Glu Ala Ser Glu Arg Lys Arg Pro Asp
            660                 665                 670
Ser Gly Cys Ser Thr Ser Lys Asp Thr Lys Tyr Gln Ser Val Tyr Val
            675                 680                 685
Ile Ser Glu Glu Lys Asp Glu Cys Val Ile Ala Thr Glu Val
        690                 695                 700

<210> SEQ ID NO 5
<211> LENGTH: 198
<212> TYPE: PRT
<213> ORGANISM: Homo sapiens

<400> SEQUENCE: 5

Ser Gly Gln Phe Glu Leu Glu Ile Leu Ser Met Gln Asn Val Asn Gly
 1               5                   10                  15
Glu Leu Gln Asn Gly Asn Cys Cys Gly Gly Ala Arg Asn Pro Gly Asp
                20                  25                  30
Arg Lys Cys Thr Arg Asp Glu Cys Asp Thr Tyr Phe Lys Val Cys Leu
            35                  40                  45
Lys Glu Tyr Gln Ser Arg Val Thr Ala Gly Gly Pro Cys Ser Phe Gly
        50                  55                  60
Ser Gly Ser Thr Pro Val Ile Gly Gly Asn Thr Phe Asn Leu Lys Ala
65                  70                  75                  80
Ser Arg Gly Asn Asp Arg Asn Arg Ile Val Leu Pro Phe Ser Phe Ala
                85                  90                  95
Trp Pro Arg Ser Tyr Thr Leu Leu Val Glu Ala Trp Asp Ser Ser Asn
                100                 105                 110
Asp Thr Val Gln Pro Asp Ser Ile Ile Glu Lys Ala Ser His Ser Gly
            115                 120                 125
Met Ile Asn Pro Ser Arg Gln Trp Gln Thr Leu Lys Gln Asn Thr Gly
        130                 135                 140
Val Ala His Phe Glu Tyr Gln Ile Arg Val Thr Cys Asp Asp Tyr Tyr
145                 150                 155                 160
Tyr Gly Phe Gly Cys Asn Lys Phe Cys Arg Pro Arg Asp Asp Phe Phe
                165                 170                 175
```

```
Gly His Tyr Ala Cys Asp Gln Asn Gly Asn Lys Thr Cys Met Glu Gly
            180                 185                 190

Trp Met Gly Pro Glu Cys
        195

<210> SEQ ID NO 6
<211> LENGTH: 1036
<212> TYPE: PRT
<213> ORGANISM: Homo sapiens

<400> SEQUENCE: 6

Ser Gly Gln Phe Glu Leu Glu Ile Leu Ser Met Gln Asn Val Asn Gly
  1               5                  10                  15

Glu Leu Gln Asn Gly Asn Cys Cys Gly Gly Ala Arg Asn Pro Gly Asp
             20                  25                  30

Arg Lys Cys Thr Arg Asp Glu Cys Asp Thr Tyr Phe Lys Val Cys Leu
         35                  40                  45

Lys Glu Tyr Gln Ser Arg Val Thr Ala Gly Gly Pro Cys Ser Phe Gly
     50                  55                  60

Ser Gly Ser Thr Pro Val Ile Gly Gly Asn Thr Phe Asn Leu Lys Ala
 65                  70                  75                  80

Ser Arg Gly Asn Asp Arg Asn Arg Ile Val Leu Pro Phe Ser Phe Ala
                 85                  90                  95

Trp Pro Arg Ser Tyr Thr Leu Leu Val Glu Ala Trp Asp Ser Ser Asn
            100                 105                 110

Asp Thr Val Gln Pro Asp Ser Ile Ile Glu Lys Ala Ser His Ser Gly
        115                 120                 125

Met Ile Asn Pro Ser Arg Gln Trp Gln Thr Leu Lys Gln Asn Thr Gly
    130                 135                 140

Val Ala His Phe Glu Tyr Gln Ile Arg Val Thr Cys Asp Asp Tyr Tyr
145                 150                 155                 160

Tyr Gly Phe Gly Cys Asn Lys Phe Cys Arg Pro Arg Asp Asp Phe Phe
                165                 170                 175

Gly His Tyr Ala Cys Asp Gln Asn Gly Asn Lys Thr Cys Met Glu Gly
            180                 185                 190

Trp Met Gly Pro Glu Cys Asn Arg Ala Ile Cys Arg Gln Gly Cys Ser
        195                 200                 205

Pro Lys His Gly Ser Cys Lys Leu Pro Gly Asp Cys Arg Cys Gln Tyr
    210                 215                 220

Gly Trp Gln Gly Leu Tyr Cys Asp Lys Cys Ile Pro His Pro Gly Cys
225                 230                 235                 240

Val His Gly Ile Cys Asn Glu Pro Trp Gln Cys Leu Cys Glu Thr Asn
                245                 250                 255

Trp Gly Gly Gln Leu Cys Asp Lys Asp Leu Asn Tyr Cys Gly Thr His
            260                 265                 270

Gln Pro Cys Leu Asn Gly Gly Thr Cys Ser Asn Thr Gly Pro Asp Lys
        275                 280                 285

Tyr Gln Cys Ser Cys Pro Glu Gly Tyr Ser Gly Pro Asn Cys Glu Ile
    290                 295                 300

Ala Glu His Ala Cys Leu Ser Asp Pro Cys His Asn Arg Gly Ser Cys
305                 310                 315                 320

Lys Glu Thr Ser Leu Gly Phe Glu Cys Glu Cys Ser Pro Gly Trp Thr
                325                 330                 335

Gly Pro Thr Cys Ser Thr Asn Ile Asp Asp Cys Ser Pro Asn Asn Cys
```

-continued

```
                340                 345                 350
Ser His Gly Gly Thr Cys Gln Asp Leu Val Asn Gly Phe Lys Cys Val
            355                 360                 365
Cys Pro Pro Gln Trp Thr Gly Lys Thr Cys Gln Leu Asp Ala Asn Glu
        370                 375                 380
Cys Glu Ala Lys Pro Cys Val Asn Ala Lys Ser Cys Lys Asn Leu Ile
385                 390                 395                 400
Ala Ser Tyr Tyr Cys Asp Cys Leu Pro Gly Trp Met Gly Gln Asn Cys
                405                 410                 415
Asp Ile Asn Ile Asn Asp Cys Leu Gly Gln Cys Gln Asn Asp Ala Ser
            420                 425                 430
Cys Arg Asp Leu Val Asn Gly Tyr Arg Cys Ile Cys Pro Pro Gly Tyr
        435                 440                 445
Ala Gly Asp His Cys Glu Arg Asp Ile Asp Glu Cys Ala Ser Asn Pro
450                 455                 460
Cys Leu Asn Gly Gly His Cys Gln Asn Glu Ile Asn Arg Phe Gln Cys
465                 470                 475                 480
Leu Cys Pro Thr Gly Phe Ser Gly Asn Leu Cys Gln Leu Asp Ile Asp
                485                 490                 495
Tyr Cys Glu Pro Asn Pro Cys Gln Asn Gly Ala Gln Cys Tyr Asn Arg
            500                 505                 510
Ala Ser Asp Tyr Phe Cys Lys Cys Pro Glu Asp Tyr Glu Gly Lys Asn
        515                 520                 525
Cys Ser His Leu Lys Asp His Cys Arg Thr Thr Pro Cys Glu Val Ile
        530                 535                 540
Asp Ser Cys Thr Val Ala Met Ala Ser Asn Asp Thr Pro Glu Gly Val
545                 550                 555                 560
Arg Tyr Ile Ser Ser Asn Val Cys Gly Pro His Gly Lys Cys Lys Ser
                565                 570                 575
Gln Ser Gly Gly Lys Phe Thr Cys Asp Cys Asn Lys Gly Phe Thr Gly
            580                 585                 590
Thr Tyr Cys His Glu Asn Ile Asn Asp Cys Glu Ser Asn Pro Cys Arg
        595                 600                 605
Asn Gly Gly Thr Cys Ile Asp Gly Val Asn Ser Tyr Lys Cys Ile Cys
    610                 615                 620
Ser Asp Gly Trp Glu Gly Ala Tyr Cys Glu Thr Asn Ile Asn Asp Cys
625                 630                 635                 640
Ser Gln Asn Pro Cys His Asn Gly Thr Cys Arg Asp Leu Val Asn
                645                 650                 655
Asp Phe Tyr Cys Asp Cys Lys Asn Gly Trp Lys Gly Lys Thr Cys His
                660                 665                 670
Ser Arg Asp Ser Gln Cys Asp Glu Ala Thr Cys Asn Asn Gly Gly Thr
        675                 680                 685
Cys Tyr Asp Glu Gly Asp Ala Phe Lys Cys Met Cys Pro Gly Gly Trp
        690                 695                 700
Glu Gly Thr Thr Cys Asn Ile Ala Arg Asn Ser Ser Cys Leu Pro Asn
705                 710                 715                 720
Pro Cys His Asn Gly Gly Thr Cys Val Val Asn Gly Glu Ser Phe Thr
                725                 730                 735
Cys Val Cys Lys Glu Gly Trp Glu Gly Pro Ile Cys Ala Gln Asn Thr
            740                 745                 750
Asn Asp Cys Ser Pro His Pro Cys Tyr Asn Ser Gly Thr Cys Val Asp
        755                 760                 765
```

```
Gly Asp Asn Trp Tyr Arg Cys Glu Cys Ala Pro Gly Phe Ala Gly Pro
        770                 775                 780

Asp Cys Arg Ile Asn Ile Asn Glu Cys Gln Ser Ser Pro Cys Ala Phe
785                 790                 795                 800

Gly Ala Thr Cys Val Asp Glu Ile Asn Gly Tyr Arg Cys Val Cys Pro
                    805                 810                 815

Pro Gly His Ser Gly Ala Lys Cys Gln Glu Val Ser Gly Arg Pro Cys
            820                 825                 830

Ile Thr Met Gly Ser Val Ile Pro Asp Gly Ala Lys Trp Asp Asp Asp
        835                 840                 845

Cys Asn Thr Cys Gln Cys Leu Asn Gly Arg Ile Ala Cys Ser Lys Val
850                 855                 860

Trp Cys Gly Pro Arg Pro Cys Leu Leu His Lys Gly His Ser Glu Cys
865                 870                 875                 880

Pro Ser Gly Gln Ser Cys Ile Pro Ile Leu Asp Asp Gln Cys Phe Val
                    885                 890                 895

His Pro Cys Thr Gly Val Gly Glu Cys Arg Ser Ser Ser Leu Gln Pro
            900                 905                 910

Val Lys Thr Lys Cys Thr Ser Asp Ser Tyr Tyr Gln Asp Asn Cys Ala
        915                 920                 925

Asn Ile Thr Phe Thr Phe Asn Lys Glu Met Met Ser Pro Gly Leu Thr
930                 935                 940

Thr Glu His Ile Cys Ser Glu Leu Arg Asn Leu Asn Ile Leu Lys Asn
945                 950                 955                 960

Val Ser Ala Glu Tyr Ser Ile Tyr Ile Ala Cys Glu Pro Ser Pro Ser
                    965                 970                 975

Ala Asn Asn Glu Ile His Val Ala Ile Ser Ala Glu Asp Ile Arg Asp
            980                 985                 990

Asp Gly Asn Pro Ile Lys Glu Ile Thr Asp Lys Ile Ile Asp Leu Val
        995                 1000                1005

Ser Lys Arg Asp Gly Asn Ser Ser Leu Ile Ala Ala Val Ala Glu Val
    1010                1015                1020

Arg Val Gln Arg Arg Pro Leu Lys Asn Arg Thr Asp
1025                1030                1035

<210> SEQ ID NO 7
<211> LENGTH: 1187
<212> TYPE: PRT
<213> ORGANISM: Homo sapiens

<400> SEQUENCE: 7

Ser Gly Gln Phe Glu Leu Glu Ile Leu Ser Met Gln Asn Val Asn Gly
  1               5                  10                  15

Glu Leu Gln Asn Gly Asn Cys Cys Gly Gly Ala Arg Asn Pro Gly Asp
                20                  25                  30

Arg Lys Cys Thr Arg Asp Glu Cys Asp Thr Tyr Phe Lys Val Cys Leu
            35                  40                  45

Lys Glu Tyr Gln Ser Arg Val Thr Ala Gly Gly Pro Cys Ser Phe Gly
        50                  55                  60

Ser Gly Ser Thr Pro Val Ile Gly Gly Asn Thr Phe Asn Leu Lys Ala
 65                  70                  75                  80

Ser Arg Gly Asn Asp Arg Asn Arg Ile Val Leu Pro Phe Ser Phe Ala
                85                  90                  95

Trp Pro Arg Ser Tyr Thr Leu Leu Val Glu Ala Trp Asp Ser Ser Asn
```

-continued

```
              100                 105                  110
Asp Thr Val Gln Pro Asp Ser Ile Ile Glu Lys Ala Ser His Ser Gly
            115                 120                 125

Met Ile Asn Pro Ser Arg Gln Trp Gln Thr Leu Lys Gln Asn Thr Gly
        130                 135             140

Val Ala His Phe Glu Tyr Gln Ile Arg Val Thr Cys Asp Asp Tyr Tyr
145                 150                 155                 160

Tyr Gly Phe Gly Cys Asn Lys Phe Cys Arg Pro Arg Asp Phe Phe
                165                 170             175

Gly His Tyr Ala Cys Asp Gln Asn Gly Asn Lys Thr Cys Met Glu Gly
            180                 185                 190

Trp Met Gly Pro Glu Cys Asn Arg Ala Ile Cys Arg Gln Gly Cys Ser
        195                 200                 205

Pro Lys His Gly Ser Cys Lys Leu Pro Gly Asp Cys Arg Cys Gln Tyr
    210                 215                 220

Gly Trp Gln Gly Leu Tyr Cys Asp Lys Cys Ile Pro His Pro Gly Cys
225                 230                 235                 240

Val His Gly Ile Cys Asn Glu Pro Trp Gln Cys Leu Cys Glu Thr Asn
                245                 250                 255

Trp Gly Gly Gln Leu Cys Asp Lys Asp Leu Asn Tyr Cys Gly Thr His
            260                 265                 270

Gln Pro Cys Leu Asn Gly Gly Thr Cys Ser Asn Thr Gly Pro Asp Lys
        275                 280                 285

Tyr Gln Cys Ser Cys Pro Glu Gly Tyr Ser Gly Pro Asn Cys Glu Ile
    290                 295                 300

Ala Glu His Ala Cys Leu Ser Asp Pro Cys His Asn Arg Gly Ser Cys
305                 310                 315                 320

Lys Glu Thr Ser Leu Gly Phe Glu Cys Glu Cys Ser Pro Gly Trp Thr
                325                 330                 335

Gly Pro Thr Cys Ser Thr Asn Ile Asp Asp Cys Ser Pro Asn Asn Cys
            340                 345                 350

Ser His Gly Gly Thr Cys Gln Asp Leu Val Asn Gly Phe Lys Cys Val
        355                 360                 365

Cys Pro Pro Gln Trp Thr Gly Lys Thr Cys Gln Leu Asp Ala Asn Glu
    370                 375                 380

Cys Glu Ala Lys Pro Cys Val Asn Ala Lys Ser Cys Lys Asn Leu Ile
385                 390                 395                 400

Ala Ser Tyr Tyr Cys Asp Cys Leu Pro Gly Trp Met Gly Gln Asn Cys
                405                 410                 415

Asp Ile Asn Ile Asn Asp Cys Leu Gly Gln Cys Gln Asn Asp Ala Ser
            420                 425                 430

Cys Arg Asp Leu Val Asn Gly Tyr Arg Cys Ile Cys Pro Pro Gly Tyr
        435                 440                 445

Ala Gly Asp His Cys Glu Arg Asp Ile Asp Glu Cys Ala Ser Asn Pro
    450                 455                 460

Cys Leu Asn Gly Gly His Cys Gln Asn Glu Ile Asn Arg Phe Gln Cys
465                 470                 475                 480

Leu Cys Pro Thr Gly Phe Ser Gly Asn Leu Cys Gln Leu Asp Ile Asp
                485                 490                 495

Tyr Cys Glu Pro Asn Pro Cys Gln Asn Gly Ala Gln Cys Tyr Asn Arg
            500                 505                 510

Ala Ser Asp Tyr Phe Cys Lys Cys Pro Glu Asp Tyr Glu Gly Lys Asn
        515                 520                 525
```

-continued

```
Cys Ser His Leu Lys Asp His Cys Arg Thr Thr Pro Cys Glu Val Ile
        530                 535                 540
Asp Ser Cys Thr Val Ala Met Ala Ser Asn Asp Thr Pro Glu Gly Val
545                 550                 555                 560
Arg Tyr Ile Ser Ser Asn Val Cys Gly Pro His Gly Lys Cys Lys Ser
                565                 570                 575
Gln Ser Gly Gly Lys Phe Thr Cys Asp Cys Asn Lys Gly Phe Thr Gly
            580                 585                 590
Thr Tyr Cys His Glu Asn Ile Asn Asp Cys Glu Ser Asn Pro Cys Arg
        595                 600                 605
Asn Gly Gly Thr Cys Ile Asp Gly Val Asn Ser Tyr Lys Cys Ile Cys
    610                 615                 620
Ser Asp Gly Trp Glu Gly Ala Tyr Cys Glu Thr Asn Ile Asn Asp Cys
625                 630                 635                 640
Ser Gln Asn Pro Cys His Asn Gly Gly Thr Cys Arg Asp Leu Val Asn
                645                 650                 655
Asp Phe Tyr Cys Asp Cys Lys Asn Gly Trp Lys Gly Lys Thr Cys His
            660                 665                 670
Ser Arg Asp Ser Gln Cys Asp Glu Ala Thr Cys Asn Asn Gly Gly Thr
        675                 680                 685
Cys Tyr Asp Glu Gly Asp Ala Phe Lys Cys Met Cys Pro Gly Gly Trp
    690                 695                 700
Glu Gly Thr Thr Cys Asn Ile Ala Arg Asn Ser Ser Cys Leu Pro Asn
705                 710                 715                 720
Pro Cys His Asn Gly Gly Thr Cys Val Val Asn Gly Glu Ser Phe Thr
                725                 730                 735
Cys Val Cys Lys Glu Gly Trp Glu Gly Pro Ile Cys Ala Gln Asn Thr
            740                 745                 750
Asn Asp Cys Ser Pro His Pro Cys Tyr Asn Ser Gly Thr Cys Val Asp
        755                 760                 765
Gly Asp Asn Trp Tyr Arg Cys Glu Cys Ala Pro Gly Phe Ala Gly Pro
    770                 775                 780
Asp Cys Arg Ile Asn Ile Asn Glu Cys Gln Ser Ser Pro Cys Ala Phe
785                 790                 795                 800
Gly Ala Thr Cys Val Asp Glu Ile Asn Gly Tyr Arg Cys Val Cys Pro
                805                 810                 815
Pro Gly His Ser Gly Ala Lys Cys Gln Glu Val Ser Gly Arg Pro Cys
            820                 825                 830
Ile Thr Met Gly Ser Val Ile Pro Asp Gly Ala Lys Trp Asp Asp Asp
        835                 840                 845
Cys Asn Thr Cys Gln Cys Leu Asn Gly Arg Ile Ala Cys Ser Lys Val
    850                 855                 860
Trp Cys Gly Pro Arg Pro Cys Leu Leu His Lys Gly His Ser Glu Cys
865                 870                 875                 880
Pro Ser Gly Gln Ser Cys Ile Pro Ile Leu Asp Asp Gln Cys Phe Val
                885                 890                 895
His Pro Cys Thr Gly Val Gly Glu Cys Arg Ser Ser Ser Leu Gln Pro
            900                 905                 910
Val Lys Thr Lys Cys Thr Ser Asp Ser Tyr Tyr Gln Asp Asn Cys Ala
        915                 920                 925
Asn Ile Thr Phe Thr Phe Asn Lys Glu Met Met Ser Pro Gly Leu Thr
    930                 935                 940
```

-continued

```
Thr Glu His Ile Cys Ser Glu Leu Arg Asn Leu Asn Ile Leu Lys Asn
945                 950                 955                 960

Val Ser Ala Glu Tyr Ser Ile Tyr Ile Ala Cys Glu Pro Ser Pro Ser
            965                 970                 975

Ala Asn Asn Glu Ile His Val Ala Ile Ser Ala Glu Asp Ile Arg Asp
        980                 985                 990

Asp Gly Asn Pro Ile Lys Glu Ile Thr Asp Lys Ile Ile Asp Leu Val
    995                 1000                1005

Ser Lys Arg Asp Gly Asn Ser Ser Leu Ile Ala Ala Val Ala Glu Val
1010                1015                1020

Arg Val Gln Arg Arg Pro Leu Lys Asn Arg Thr Asp Phe Leu Val Pro
1025                1030                1035                1040

Leu Leu Ser Ser Val Leu Thr Val Ala Trp Ile Cys Cys Leu Val Thr
                1045                1050                1055

Ala Phe Tyr Trp Cys Leu Arg Lys Arg Lys Pro Gly Ser His Thr
            1060                1065                1070

His Ser Ala Ser Glu Asp Asn Thr Thr Asn Asn Val Arg Glu Gln Leu
        1075                1080                1085

Asn Gln Ile Lys Asn Pro Ile Glu Lys His Gly Ala Asn Thr Val Pro
    1090                1095                1100

Ile Lys Asp Tyr Glu Asn Lys Asn Ser Lys Met Ser Lys Ile Arg Thr
1105                1110                1115                1120

His Asn Ser Glu Val Glu Glu Asp Asp Met Asp Lys His Gln Gln Lys
                1125                1130                1135

Ala Arg Phe Ala Lys Gln Pro Ala Tyr Thr Leu Val Asp Arg Glu Glu
            1140                1145                1150

Lys Pro Pro Asn Gly Thr Pro Thr Lys His Pro Asn Trp Thr Asn Lys
        1155                1160                1165

Gln Asp Asn Arg Asp Leu Glu Ser Ala Gln Ser Leu Asn Arg Met Glu
    1170                1175                1180

Tyr Ile Val
1185

<210> SEQ ID NO 8
<211> LENGTH: 2663
<212> TYPE: DNA
<213> ORGANISM: Homo sapiens
<220> FEATURE:
<221> NAME/KEY: CDS
<222> LOCATION: (179)..(2347)

<400> SEQUENCE: 8
cttgggaaga ggcggagacc ggcttttaaa gaaagaagtc ctgggtcctg cggtctgggg    60
cgaggcaagg gcgcttttct gcccacgctc ccgtggccc atcgatcccc cgcgcgtccg    120
ccgctgttct aaggagagaa gtgggggccc cccaggctcg cgcgtggagc gaagcagc     178 atg ggc agt cgg tgc gcg ctg gcc ctg gcg gtg ctc tcg gcc ttg ctg    226
Met Gly Ser Arg Cys Ala Leu Ala Leu Ala Val Leu Ser Ala Leu Leu
1               5                   10                  15 tgt cag gtc tgg agc tct ggg gtg ttc gaa ctg aag ctg cag gag ttc    274
Cys Gln Val Trp Ser Ser Gly Val Phe Glu Leu Lys Leu Gln Glu Phe
            20                  25                  30 gtc aac aag aag ggg ctg ctg ggg aac cgc aac tgc tgc cgc ggg ggc    322
Val Asn Lys Lys Gly Leu Leu Gly Asn Arg Asn Cys Cys Arg Gly Gly
        35                  40                  45 gcg ggg cca ccg ccg tgc gcc tgc cgg acc ttc ttc cgc gtg tgc ctc    370
Ala Gly Pro Pro Pro Cys Ala Cys Arg Thr Phe Phe Arg Val Cys Leu
```

```
                        50                      55                      60
aag cac tac cag gcc agc gtg tcc ccc gag ccg ccc tgc acc tac ggc              418
Lys His Tyr Gln Ala Ser Val Ser Pro Glu Pro Pro Cys Thr Tyr Gly
 65                  70                      75                  80 agc gcc gtc acc ccc gtg ctg ggc gtc gac tcc ttc agt ctg ccc gac              466
Ser Ala Val Thr Pro Val Leu Gly Val Asp Ser Phe Ser Leu Pro Asp
                     85                      90                  95 ggc ggg ggc gcc gac tcc gcg ttc agc aac ccc atc cgc ttc ccc ttc              514
Gly Gly Gly Ala Asp Ser Ala Phe Ser Asn Pro Ile Arg Phe Pro Phe
                100                     105                     110 ggc ttc acc tgg ccg ggc acc ttc tct ctg att att gaa gct ctc cac              562
Gly Phe Thr Trp Pro Gly Thr Phe Ser Leu Ile Ile Glu Ala Leu His
                115                     120                     125 aca gat tct cct gat gac ctc gca aca gaa aac cca gaa aga ctc atc              610
Thr Asp Ser Pro Asp Asp Leu Ala Thr Glu Asn Pro Glu Arg Leu Ile
130                     135                     140 agc cgc ctg gcc acc cag agg cac ctg acg gtg ggc gag gag tgg tcc              658
Ser Arg Leu Ala Thr Gln Arg His Leu Thr Val Gly Glu Glu Trp Ser
145                     150                     155                     160 cag gac ctg cac agc agc ggc cgc acg gac ctc aag tac tcc tac cgc              706
Gln Asp Leu His Ser Ser Gly Arg Thr Asp Leu Lys Tyr Ser Tyr Arg
                165                     170                     175 ttc gtg tgt gac gaa cac tac tac gga gag ggc tgc tcc gtt ttc tgc              754
Phe Val Cys Asp Glu His Tyr Tyr Gly Glu Gly Cys Ser Val Phe Cys
                180                     185                     190 cgt ccc cgg gac gat gcc ttc ggc cac ttc acc tgt ggg gag cgt ggg              802
Arg Pro Arg Asp Asp Ala Phe Gly His Phe Thr Cys Gly Glu Arg Gly
                195                     200                     205 gag aaa gtg tgc aac cct ggc tgg aaa ggg ccc tac tgc aca gag ccg              850
Glu Lys Val Cys Asn Pro Gly Trp Lys Gly Pro Tyr Cys Thr Glu Pro
210                     215                     220 atc tgc ctg cct gga tgt gat gag cag cat gga ttt tgt gac aaa cca              898
Ile Cys Leu Pro Gly Cys Asp Glu Gln His Gly Phe Cys Asp Lys Pro
225                     230                     235                     240 ggg gaa tgc aag tgc aga gtg ggc tgg cag ggc cgg tac tgt gac gag              946
Gly Glu Cys Lys Cys Arg Val Gly Trp Gln Gly Arg Tyr Cys Asp Glu
                245                     250                     255 tgt atc cgc tat cca ggc tgt ctc cat ggc acc tgc cag cag ccc tgg              994
Cys Ile Arg Tyr Pro Gly Cys Leu His Gly Thr Cys Gln Gln Pro Trp
                260                     265                     270 cag tgc aac tgc cag gaa ggc tgg ggg ggc ctt ttc tgc aac cag gac             1042
Gln Cys Asn Cys Gln Glu Gly Trp Gly Gly Leu Phe Cys Asn Gln Asp
                275                     280                     285 ctg aac tac tgc aca cac cat aag ccc tgc aag aat gga gcc acc tgc             1090
Leu Asn Tyr Cys Thr His His Lys Pro Cys Lys Asn Gly Ala Thr Cys
                290                     295                     300 acc aac acg ggc cag ggg agc tac act tgc tct tgc cgg cct ggg tac             1138
Thr Asn Thr Gly Gln Gly Ser Tyr Thr Cys Ser Cys Arg Pro Gly Tyr
305                     310                     315                     320 aca ggt gcc acc tgc gag ctg ggg att gac gag tgt gac ccc agc cct             1186
Thr Gly Ala Thr Cys Glu Leu Gly Ile Asp Glu Cys Asp Pro Ser Pro
                325                     330                     335 tgt aag aac gga ggg agc tgc acg gat ctc gag aac agc tac tcc tgt             1234
Cys Lys Asn Gly Gly Ser Cys Thr Asp Leu Glu Asn Ser Tyr Ser Cys
                340                     345                     350 acc tgc cca ccc ggc ttc tac ggc aaa atc tgt gaa ttg agt gcc atg             1282
Thr Cys Pro Pro Gly Phe Tyr Gly Lys Ile Cys Glu Leu Ser Ala Met
                355                     360                     365 acc tgt gcg gac ggc cct tgc ttt aac ggg ggt cgg tgc tca gac agc             1330
```

-continued

```
        Thr Cys Ala Asp Gly Pro Cys Phe Asn Gly Gly Arg Cys Ser Asp Ser
            370                 375                 380 ccc gat gga ggg tac agc tgc cgc tgc ccc gtg ggc tac tcc ggc ttc        1378
Pro Asp Gly Gly Tyr Ser Cys Arg Cys Pro Val Gly Tyr Ser Gly Phe
385                 390                 395                 400 aac tgt gag aag aaa att gac tac tgc agc tct tca ccc tgt tct aat        1426
Asn Cys Glu Lys Lys Ile Asp Tyr Cys Ser Ser Ser Pro Cys Ser Asn
                405                 410                 415 ggt gcc aag tgt gtg gac ctc ggt gat gcc tac ctg tgc cgc tgc cag        1474
Gly Ala Lys Cys Val Asp Leu Gly Asp Ala Tyr Leu Cys Arg Cys Gln
            420                 425                 430 gcc ggc ttc tcg ggg agg cac tgt gac gac aac gtg gac gac tgc gcc        1522
Ala Gly Phe Ser Gly Arg His Cys Asp Asp Asn Val Asp Asp Cys Ala
        435                 440                 445 tcc tcc ccg tgc gcc aac ggg ggc acc tgc cgg gat ggc gtg aac gac        1570
Ser Ser Pro Cys Ala Asn Gly Gly Thr Cys Arg Asp Gly Val Asn Asp
    450                 455                 460 ttc tcc tgc acc tgc ccg cct ggc tac acg ggc agg aac tgc agt gcc        1618
Phe Ser Cys Thr Cys Pro Pro Gly Tyr Thr Gly Arg Asn Cys Ser Ala
465                 470                 475                 480 ccc gtc agc agg tgc gag cac gca ccc tgc cac aat ggg gcc acc tgc        1666
Pro Val Ser Arg Cys Glu His Ala Pro Cys His Asn Gly Ala Thr Cys
                485                 490                 495 cac gag agg ggc cac cgc tat gtg tgc gag tgt gcc cga ggc tac ggg        1714
His Glu Arg Gly His Arg Tyr Val Cys Glu Cys Ala Arg Gly Tyr Gly
            500                 505                 510 ggt ccc aac tgc cag ttc ctg ctc ccc gag ctg ccc ccg ggc cca gcg        1762
Gly Pro Asn Cys Gln Phe Leu Leu Pro Glu Leu Pro Pro Gly Pro Ala
        515                 520                 525 gtg gtg gac ctc act gag aag cta gag ggc cag ggc ggg cca ttc ccc        1810
Val Val Asp Leu Thr Glu Lys Leu Glu Gly Gln Gly Gly Pro Phe Pro
    530                 535                 540 tgg gtg gcc gtg tgc gcc ggg gtc atc ctt gtc ctc atg ctg ctg ctg        1858
Trp Val Ala Val Cys Ala Gly Val Ile Leu Val Leu Met Leu Leu Leu
545                 550                 555                 560 ggc tgt gcc gct gtg gtg gtc tgc gtc cgg ctg agg ctg cag aag cac        1906
Gly Cys Ala Ala Val Val Val Cys Val Arg Leu Arg Leu Gln Lys His
                565                 570                 575 cgg ccc cca gcc gac ccc tgc cgg ggg gag acg gag acc atg aac aac        1954
Arg Pro Pro Ala Asp Pro Cys Arg Gly Glu Thr Glu Thr Met Asn Asn
            580                 585                 590 ctg gcc aac tgc cag cgt gag aag gac atc tca gtc agc atc atc ggg        2002
Leu Ala Asn Cys Gln Arg Glu Lys Asp Ile Ser Val Ser Ile Ile Gly
        595                 600                 605 gcc acg cag atc aag aac acc aac aag aag gcg gac ttc cac ggg gac        2050
Ala Thr Gln Ile Lys Asn Thr Asn Lys Lys Ala Asp Phe His Gly Asp
    610                 615                 620 cac agc gcc gac aag aat ggc ttc aag gcc cgc tac cca gcg gtg gac        2098
His Ser Ala Asp Lys Asn Gly Phe Lys Ala Arg Tyr Pro Ala Val Asp
625                 630                 635                 640 tat aac ctc gtg cag gac ctc aag ggt gac gac acc gcc gtc agg gac        2146
Tyr Asn Leu Val Gln Asp Leu Lys Gly Asp Asp Thr Ala Val Arg Asp
                645                 650                 655 gcg cac agc aag cgt gac acc aag tgc cag ccc cag ggc tcc tca ggg        2194
Ala His Ser Lys Arg Asp Thr Lys Cys Gln Pro Gln Gly Ser Ser Gly
            660                 665                 670 gag gag aag ggg acc ccg acc aca ctc agg ggt gga gaa gca tct gaa        2242
Glu Glu Lys Gly Thr Pro Thr Thr Leu Arg Gly Gly Glu Ala Ser Glu
        675                 680                 685
```

-continued

```
aga aaa agg ccg gac tcg ggc tgt tca act tca aaa gac acc aag tac      2290
Arg Lys Arg Pro Asp Ser Gly Cys Ser Thr Ser Lys Asp Thr Lys Tyr
        690             695                 700 cag tcg gtg tac gtc ata tcc gag gag aag gat gag tgc gtc ata gca      2338
Gln Ser Val Tyr Val Ile Ser Glu Glu Lys Asp Glu Cys Val Ile Ala
705                 710                 715                 720 act gag gtg taaaatggaa gtgagatggc aagactcccg tttctcttaa              2387
Thr Glu Val aataagtaaa attccaagga tatatgcccc aacgaatgct gctgaagagg agggaggcct    2447
cgtggactgc tgctgagaaa ccagttcag accgagcagg ttctcctcct gaggtcctcg     2507
acgcctgccg acagcctgtc gcggcccggc cgcctgcggc actgccttcc gtgacgtcgc    2567
cgttgcacta tggacagttg ctcttaagag aatatatatt taaatgggtg aactgaatta    2627
cgcataagaa gcatgcactg cctgagtgta tatttt                              2663
```

<210> SEQ ID NO 9
<211> LENGTH: 723
<212> TYPE: PRT
<213> ORGANISM: Homo sapiens

<400> SEQUENCE: 9

```
Met Gly Ser Arg Cys Ala Leu Ala Leu Ala Val Leu Ser Ala Leu Leu
 1               5                  10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
            35                  40                  45

Ala Gly Pro Pro Pro Cys Ala Cys Arg Thr Phe Phe Arg Val Cys Leu
        50                  55                  60

Lys His Tyr Gln Ala Ser Val Ser Pro Glu Pro Pro Cys Thr Tyr Gly
 65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270
```

-continued

```
Gln Cys Asn Cys Gln Glu Gly Trp Gly Gly Leu Phe Cys Asn Gln Asp
                275                 280                 285

Leu Asn Tyr Cys Thr His His Lys Pro Cys Lys Asn Gly Ala Thr Cys
        290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
                340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
        370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
                420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
        450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
                500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
                565                 570                 575

Arg Pro Pro Ala Asp Pro Cys Arg Gly Glu Thr Glu Thr Met Asn Asn
                580                 585                 590

Leu Ala Asn Cys Gln Arg Glu Lys Asp Ile Ser Val Ser Ile Ile Gly
        595                 600                 605

Ala Thr Gln Ile Lys Asn Thr Asn Lys Lys Ala Asp Phe His Gly Asp
        610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
                660                 665                 670

Glu Glu Lys Gly Thr Pro Thr Thr Leu Arg Gly Gly Glu Ala Ser Glu
        675                 680                 685
```

-continued

```
        Arg Lys Arg Pro Asp Ser Gly Cys Ser Thr Ser Lys Asp Thr Lys Tyr
            690                 695                 700

Gln Ser Val Tyr Val Ile Ser Glu Glu Lys Asp Glu Cys Val Ile Ala
        705                 710                 715                 720

Thr Glu Val

<210> SEQ ID NO 10
<211> LENGTH: 4208
<212> TYPE: DNA
<213> ORGANISM: Homo sapiens
<220> FEATURE:
<221> NAME/KEY: CDS
<222> LOCATION: (409)..(4062)

<400> SEQUENCE: 10
ggccggcccg cgagctaggc tggttttttt ttttctcccc tccctccccc cttttccat        60 gcagctgatc taaaagggaa taaaaggctg cgcataatca taataataaa agaaggggag      120
cgcgagagaa ggaaagaaag ccgggaggtg aagaggagg gggagcgtct caaagaagcg       180
atcagaataa taaaaggagg ccgggctctt tgccttctgg aacgggccgc tcttgaaagg      240
gcttttgaaa agtggtgttg ttttccagtc gtgcatgctc caatcggcgg agtatattag     300
agccgggacg cggcggccgc aggggcagcg gcgacggcag caccggcggc agcaccagcg     360
cgaacagcag cggcggcgtc ccgagtgccc gcggcgcgcg gcgcagcg atg cgt tcc       417
                                                    Met Arg Ser
                                                      1 cca cgg acg cgc ggc cgg tcc ggg cgc ccc cta agc ctc ctg ctc gcc       465
Pro Arg Thr Arg Gly Arg Ser Gly Arg Pro Leu Ser Leu Leu Leu Ala
      5                  10                  15 ctg ctc tgt gcc ctg cga gcc aag gtg tgt ggg gcc tcg ggt cag ttc       513
Leu Leu Cys Ala Leu Arg Ala Lys Val Cys Gly Ala Ser Gly Gln Phe
 20                  25                  30                  35 gag ttg gag atc ctg tcc atg cag aac gtg aac ggg gag ctg cag aac       561
Glu Leu Glu Ile Leu Ser Met Gln Asn Val Asn Gly Glu Leu Gln Asn
                 40                  45                  50 ggg aac tgc tgc ggc ggc gcc cgg aac ccg gga gac cgc aag tgc acc       609
Gly Asn Cys Cys Gly Gly Ala Arg Asn Pro Gly Asp Arg Lys Cys Thr
             55                  60                  65 cgc gac gag tgt gac aca tac ttc aaa gtg tgc ctc aag gag tat cag       657
Arg Asp Glu Cys Asp Thr Tyr Phe Lys Val Cys Leu Lys Glu Tyr Gln
         70                  75                  80 tcc cgc gtc acg gcc ggg ggg ccc tgc agc ttc ggc tca ggg tcc acg       705
Ser Arg Val Thr Ala Gly Gly Pro Cys Ser Phe Gly Ser Gly Ser Thr
     85                  90                  95 cct gtc atc ggg ggc aac acc ttc aac ctc aag gcc agc cgc ggc aac       753
Pro Val Ile Gly Gly Asn Thr Phe Asn Leu Lys Ala Ser Arg Gly Asn
100                 105                 110                 115 gac cgc aac cgc atc gtg ctg cct ttc agt ttc gcc tgg ccg agg tcc       801
Asp Arg Asn Arg Ile Val Leu Pro Phe Ser Phe Ala Trp Pro Arg Ser
                120                 125                 130 tat acg ttg ctt gtg gag gcg tgg gat tcc agt aat gac acc gtt caa       849
Tyr Thr Leu Leu Val Glu Ala Trp Asp Ser Ser Asn Asp Thr Val Gln
            135                 140                 145 cct gac agt att att gaa aag gct tct cac tcg ggc atg atc aac ccc       897
Pro Asp Ser Ile Ile Glu Lys Ala Ser His Ser Gly Met Ile Asn Pro
        150                 155                 160 agc cgg cag tgg cag acg ctg aag cag aac acg ggc gtt gcc cac ttt       945
Ser Arg Gln Trp Gln Thr Leu Lys Gln Asn Thr Gly Val Ala His Phe
    165                 170                 175
```

-continued

| | | |
|---|---|---|
| gag tat cag atc cgc gtg acc tgt gat gac tac tac tat ggc ttt ggc<br>Glu Tyr Gln Ile Arg Val Thr Cys Asp Asp Tyr Tyr Tyr Gly Phe Gly<br>180                185                190                195 | 993 |
| tgc aat aag ttc tgc cgc ccc aga gat gac ttc ttt gga cac tat gcc<br>Cys Asn Lys Phe Cys Arg Pro Arg Asp Asp Phe Phe Gly His Tyr Ala<br>                200                205                210 | 1041 |
| tgt gac cag aat ggc aac aaa act tgc atg gaa ggc tgg atg ggc ccc<br>Cys Asp Gln Asn Gly Asn Lys Thr Cys Met Glu Gly Trp Met Gly Pro<br>215                220                225 | 1089 |
| gaa tgt aac aga gct att tgc cga caa ggc tgc agt cct aag cat ggg<br>Glu Cys Asn Arg Ala Ile Cys Arg Gln Gly Cys Ser Pro Lys His Gly<br>230                235                240 | 1137 |
| tct tgc aaa ctc cca ggt gac tgc agg tgc cag tac ggc tgg caa ggc<br>Ser Cys Lys Leu Pro Gly Asp Cys Arg Cys Gln Tyr Gly Trp Gln Gly<br>245                250                255 | 1185 |
| ctg tac tgt gat aag tgc atc cca cac ccg gga tgc gtc cac ggc atc<br>Leu Tyr Cys Asp Lys Cys Ile Pro His Pro Gly Cys Val His Gly Ile<br>260                265                270                275 | 1233 |
| tgt aat gag ccc tgg cag tgc ctc tgt gag acc aac tgg ggc ggc cag<br>Cys Asn Glu Pro Trp Gln Cys Leu Cys Glu Thr Asn Trp Gly Gly Gln<br>                      280                285                290 | 1281 |
| ctc tgt gac aaa gat ctc aat tac tgt ggg act cat cag ccg tgt ctc<br>Leu Cys Asp Lys Asp Leu Asn Tyr Cys Gly Thr His Gln Pro Cys Leu<br>295                300                305 | 1329 |
| aac ggg gga act tgt agc aac aca ggc cct gac aaa tat cag tgt tcc<br>Asn Gly Gly Thr Cys Ser Asn Thr Gly Pro Asp Lys Tyr Gln Cys Ser<br>310                315                320 | 1377 |
| tgc cct gag ggg tat tca gga ccc aac tgt gaa att gct gag cac gcc<br>Cys Pro Glu Gly Tyr Ser Gly Pro Asn Cys Glu Ile Ala Glu His Ala<br>325                330                335 | 1425 |
| tgc ctc tct gat ccc tgt cac aac aga ggc agc tgt aag gag acc tcc<br>Cys Leu Ser Asp Pro Cys His Asn Arg Gly Ser Cys Lys Glu Thr Ser<br>340                345                350                355 | 1473 |
| ctg ggc ttt gag tgt gag tgt tcc cca ggc tgg acc ggc ccc aca tgc<br>Leu Gly Phe Glu Cys Glu Cys Ser Pro Gly Trp Thr Gly Pro Thr Cys<br>                      360                365                370 | 1521 |
| tct aca aac att gat gac tgt tct cct aat aac tgt tcc cac ggg ggc<br>Ser Thr Asn Ile Asp Asp Cys Ser Pro Asn Asn Cys Ser His Gly Gly<br>375                380                385 | 1569 |
| acc tgc cag gac ctg gtt aac gga ttt aag tgt gtg tgc ccc cca cag<br>Thr Cys Gln Asp Leu Val Asn Gly Phe Lys Cys Val Cys Pro Pro Gln<br>390                395                400 | 1617 |
| tgg act ggg aaa acg tgc cag tta gat gca aat gaa tgt gag gcc aaa<br>Trp Thr Gly Lys Thr Cys Gln Leu Asp Ala Asn Glu Cys Glu Ala Lys<br>405                410                415 | 1665 |
| cct tgt gta aac gcc aaa tcc tgt aag aat ctc att gcc agc tac tac<br>Pro Cys Val Asn Ala Lys Ser Cys Lys Asn Leu Ile Ala Ser Tyr Tyr<br>420                425                430                435 | 1713 |
| tgc gac tgt ctt ccc ggc tgg atg ggt cag aat tgt gac ata aat att<br>Cys Asp Cys Leu Pro Gly Trp Met Gly Gln Asn Cys Asp Ile Asn Ile<br>                      440                445                450 | 1761 |
| aat gac tgc ctt ggc cag tgt cag aat gac gcc tcc tgt cgg gat ttg<br>Asn Asp Cys Leu Gly Gln Cys Gln Asn Asp Ala Ser Cys Arg Asp Leu<br>455                460                465 | 1809 |
| gtt aat ggt tat cgc tgt atc tgt cca cct ggc tat gca ggc gat cac<br>Val Asn Gly Tyr Arg Cys Ile Cys Pro Pro Gly Tyr Ala Gly Asp His<br>470                475                480 | 1857 |
| tgt gag aga gac atc gat gaa tgt gcc agc aac ccc tgt ttg aat ggg<br>Cys Glu Arg Asp Ile Asp Glu Cys Ala Ser Asn Pro Cys Leu Asn Gly<br>485                490                495 | 1905 |

```
ggt cac tgt cag aat gaa atc aac aga ttc cag tgt ctg tgt ccc act       1953
Gly His Cys Gln Asn Glu Ile Asn Arg Phe Gln Cys Leu Cys Pro Thr
500                 505                 510                 515 ggt ttc tct gga aac ctc tgt cag ctg gac atc gat tat tgt gag cct       2001
Gly Phe Ser Gly Asn Leu Cys Gln Leu Asp Ile Asp Tyr Cys Glu Pro
            520                 525                 530 aat ccc tgc cag aac ggt gcc cag tgc tac aac cgt gcc agt gac tat       2049
Asn Pro Cys Gln Asn Gly Ala Gln Cys Tyr Asn Arg Ala Ser Asp Tyr
535                 540                 545 ttc tgc aag tgc ccc gag gac tat gag ggc aag aac tgc tca cac ctg       2097
Phe Cys Lys Cys Pro Glu Asp Tyr Glu Gly Lys Asn Cys Ser His Leu
        550                 555                 560 aaa gac cac tgc cgc acg acc ccc tgt gaa gtg att gac agc tgc aca       2145
Lys Asp His Cys Arg Thr Thr Pro Cys Glu Val Ile Asp Ser Cys Thr
565                 570                 575 gtg gcc atg gct tcc aac gac aca cct gaa ggg gtg cgg tat att tcc       2193
Val Ala Met Ala Ser Asn Asp Thr Pro Glu Gly Val Arg Tyr Ile Ser
580                 585                 590                 595 tcc aac gtc tgt ggt cct cac ggg aag tgc aag agt cag tcg gga ggc       2241
Ser Asn Val Cys Gly Pro His Gly Lys Cys Lys Ser Gln Ser Gly Gly
            600                 605                 610 aaa ttc acc tgt gac tgt aac aaa ggc ttc acg gga aca tac tgc cat       2289
Lys Phe Thr Cys Asp Cys Asn Lys Gly Phe Thr Gly Thr Tyr Cys His
                615                 620                 625 gaa aat att aat gac tgt gag agc aac cct tgt aga aac ggt ggc act       2337
Glu Asn Ile Asn Asp Cys Glu Ser Asn Pro Cys Arg Asn Gly Gly Thr
                630                 635                 640 tgc atc gat ggt gtc aac tcc tac aag tgc atc tgt agt gac ggc tgg       2385
Cys Ile Asp Gly Val Asn Ser Tyr Lys Cys Ile Cys Ser Asp Gly Trp
645                 650                 655 gag ggg gcc tac tgt gaa acc aat att aat gac tgc agc cag aac ccc       2433
Glu Gly Ala Tyr Cys Glu Thr Asn Ile Asn Asp Cys Ser Gln Asn Pro
660                 665                 670                 675 tgc cac aat ggg ggc acg tgt cgc gac ctg gtc aat gac ttc tac tgt       2481
Cys His Asn Gly Gly Thr Cys Arg Asp Leu Val Asn Asp Phe Tyr Cys
            680                 685                 690 gac tgt aaa aat ggg tgg aaa gga aag acc tgc cac tca cgt gac agt       2529
Asp Cys Lys Asn Gly Trp Lys Gly Lys Thr Cys His Ser Arg Asp Ser
            695                 700                 705 cag tgt gat gag gcc acg tgc aac aac ggt ggc acc tgc tat gat gag       2577
Gln Cys Asp Glu Ala Thr Cys Asn Asn Gly Gly Thr Cys Tyr Asp Glu
            710                 715                 720 ggg gat gct ttt aag tgc atg tgt cct ggc ggc tgg gaa gga aca acc       2625
Gly Asp Ala Phe Lys Cys Met Cys Pro Gly Gly Trp Glu Gly Thr Thr
725                 730                 735 tgt aac ata gcc cga aac agt agc tgc ctg ccc aac ccc tgc cat aat       2673
Cys Asn Ile Ala Arg Asn Ser Ser Cys Leu Pro Asn Pro Cys His Asn
740                 745                 750                 755 ggg ggc aca tgt gtg gtc aac ggc gag tcc ttt acg tgc gtc tgc aag       2721
Gly Gly Thr Cys Val Val Asn Gly Glu Ser Phe Thr Cys Val Cys Lys
            760                 765                 770 gaa ggc tgg gag ggg ccc atc tgt gct cag aat acc aat gac tgc agc       2769
Glu Gly Trp Glu Gly Pro Ile Cys Ala Gln Asn Thr Asn Asp Cys Ser
            775                 780                 785 cct cat ccc tgt tac aac agc ggc acc tgt gtg gat gga gac aac tgg       2817
Pro His Pro Cys Tyr Asn Ser Gly Thr Cys Val Asp Gly Asp Asn Trp
            790                 795                 800 tac cgg tgc gaa tgt gcc ccg ggt ttt gct ggg ccc gac tgc aga ata       2865
Tyr Arg Cys Glu Cys Ala Pro Gly Phe Ala Gly Pro Asp Cys Arg Ile
```

-continued

| | |
|---|---|
| aac atc aat gaa tgc cag tct tca cct tgt gcc ttt gga gcg acc tgt<br>Asn Ile Asn Glu Cys Gln Ser Ser Pro Cys Ala Phe Gly Ala Thr Cys<br>820                     825                     830                     835 | 2913 |
| gtg gat gag atc aat ggc tac cgg tgt gtc tgc cct cca ggg cac agt<br>Val Asp Glu Ile Asn Gly Tyr Arg Cys Val Cys Pro Pro Gly His Ser<br>                     840                     845                     850 | 2961 |
| ggt gcc aag tgc cag gaa gtt tca ggg aga cct tgc atc acc atg ggg<br>Gly Ala Lys Cys Gln Glu Val Ser Gly Arg Pro Cys Ile Thr Met Gly<br>855                     860                     865 | 3009 |
| agt gtg ata cca gat ggg gcc aaa tgg gat gat gac tgt aat acc tgc<br>Ser Val Ile Pro Asp Gly Ala Lys Trp Asp Asp Asp Cys Asn Thr Cys<br>                     870                     875                     880 | 3057 |
| cag tgc ctg aat gga cgg atc gcc tgc tca aag gtc tgg tgt ggc cct<br>Gln Cys Leu Asn Gly Arg Ile Ala Cys Ser Lys Val Trp Cys Gly Pro<br>885                     890                     895 | 3105 |
| cga cct tgc ctg ctc cac aaa ggg cac agc gag tgc ccc agc ggg cag<br>Arg Pro Cys Leu Leu His Lys Gly His Ser Glu Cys Pro Ser Gly Gln<br>900                     905                     910                     915 | 3153 |
| agc tgc atc ccc atc ctg gac gac cag tgc ttc gtc cac ccc tgc act<br>Ser Cys Ile Pro Ile Leu Asp Asp Gln Cys Phe Val His Pro Cys Thr<br>                     920                     925                     930 | 3201 |
| ggt gtg ggc gag tgt cgg tct tcc agt ctc cag ccg gtg aag aca aag<br>Gly Val Gly Glu Cys Arg Ser Ser Ser Leu Gln Pro Val Lys Thr Lys<br>935                     940                     945 | 3249 |
| tgc acc tct gac tcc tat tac cag gat aac tgt gcg aac atc aca ttt<br>Cys Thr Ser Asp Ser Tyr Tyr Gln Asp Asn Cys Ala Asn Ile Thr Phe<br>                     950                     955                     960 | 3297 |
| acc ttt aac aag gag atg atg tca cca ggt ctt act acg gag cac att<br>Thr Phe Asn Lys Glu Met Met Ser Pro Gly Leu Thr Thr Glu His Ile<br>965                     970                     975 | 3345 |
| tgc agt gaa ttg agg aat ttg aat att ttg aag aat gtt tcc gct gaa<br>Cys Ser Glu Leu Arg Asn Leu Asn Ile Leu Lys Asn Val Ser Ala Glu<br>980                     985                     990                     995 | 3393 |
| tat tca atc tac atc gct tgc gag cct tcc cct tca gcg aac aat gaa<br>Tyr Ser Ile Tyr Ile Ala Cys Glu Pro Ser Pro Ser Ala Asn Asn Glu<br>                     1000                  1005                  1010 | 3441 |
| ata cat gtg gcc att tct gct gaa gat ata cgg gat gat ggg aac ccg<br>Ile His Val Ala Ile Ser Ala Glu Asp Ile Arg Asp Asp Gly Asn Pro<br>1015                  1020                  1025 | 3489 |
| atc aag gaa atc act gac aaa ata atc gat ctt gtt agt aaa cgt gat<br>Ile Lys Glu Ile Thr Asp Lys Ile Ile Asp Leu Val Ser Lys Arg Asp<br>1030                  1035                  1040 | 3537 |
| gga aac agc tcg ctg att gct gcc gtt gca gaa gta aga gtt cag agg<br>Gly Asn Ser Ser Leu Ile Ala Ala Val Ala Glu Val Arg Val Gln Arg<br>1045                  1050                  1055 | 3585 |
| cgg cct ctg aag aac aga aca gat ttc ctt gtt ccc ttg ctg agc tct<br>Arg Pro Leu Lys Asn Arg Thr Asp Phe Leu Val Pro Leu Leu Ser Ser<br>1060                  1065                  1070                  1075 | 3633 |
| gtc tta act gtg gct tgg atc tgt tgc ttg gtg acg gcc ttc tac tgg<br>Val Leu Thr Val Ala Trp Ile Cys Cys Leu Val Thr Ala Phe Tyr Trp<br>1080                  1085                  1090 | 3681 |
| tgc ctg cgg aag cgg cgg aag ccg ggc agc cac aca cac tca gcc tct<br>Cys Leu Arg Lys Arg Arg Lys Pro Gly Ser His Thr His Ser Ala Ser<br>1095                  1100                  1105 | 3729 |
| gag gac aac acc acc aac aac gtg cgg gag cag ctg aac cag atc aaa<br>Glu Asp Asn Thr Thr Asn Asn Val Arg Glu Gln Leu Asn Gln Ile Lys<br>1110                  1115                  1120 | 3777 |
| aac ccc att gag aaa cat ggg gcc aac acg gtc ccc atc aag gat tat | 3825 |

-continued

```
Asn Pro Ile Glu Lys His Gly Ala Asn Thr Val Pro Ile Lys Asp Tyr
    1125                1130                1135 gag aac aag aac tcc aaa atg tct aaa ata agg aca cac aat tct gaa       3873
Glu Asn Lys Asn Ser Lys Met Ser Lys Ile Arg Thr His Asn Ser Glu
1140                1145                1150                1155 gta gaa gag gac gac atg gac aaa cac cag cag aaa gcc cgg ttt gcc       3921
Val Glu Glu Asp Asp Met Asp Lys His Gln Gln Lys Ala Arg Phe Ala
                1160                1165                1170 aag cag ccg gcg tac acg ctg gta gac aga gaa gag aag ccc ccc aac       3969
Lys Gln Pro Ala Tyr Thr Leu Val Asp Arg Glu Glu Lys Pro Pro Asn
            1175                1180                1185 ggc acg ccg aca aaa cac cca aac tgg aca aac aaa cag gac aac aga       4017
Gly Thr Pro Thr Lys His Pro Asn Trp Thr Asn Lys Gln Asp Asn Arg
        1190                1195                1200 gac ttg gaa agt gcc cag agc tta aac cga atg gag tac atc gta            4062
Asp Leu Glu Ser Ala Gln Ser Leu Asn Arg Met Glu Tyr Ile Val
    1205                1210                1215 tagcagaccg cgggcactgc cgccgctagg tagagtctga gggcttgtag ttctttaaac      4122
tgtcgtgtca tactcgagtc tgaggccgtt gctgacttag aatccctgtg ttaatttaag      4182
ttttgacaag ctggcttaca ctggca                                           4208
```

<210> SEQ ID NO 11
<211> LENGTH: 1218
<212> TYPE: PRT
<213> ORGANISM: Homo sapiens

<400> SEQUENCE: 11

```
Met Arg Ser Pro Arg Thr Arg Gly Arg Ser Gly Arg Pro Leu Ser Leu
 1               5                  10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220
```

-continued

```
Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
                340                 345                 350

Glu Thr Ser Leu Gly Phe Glu Cys Glu Cys Ser Pro Gly Trp Thr Gly
            355                 360                 365

Pro Thr Cys Ser Thr Asn Ile Asp Asp Cys Ser Pro Asn Asn Cys Ser
370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
                420                 425                 430

Ser Tyr Tyr Cys Asp Cys Leu Pro Gly Trp Met Gly Gln Asn Cys Asp
            435                 440                 445

Ile Asn Ile Asn Asp Cys Leu Gly Gln Cys Gln Asn Asp Ala Ser Cys
450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
            515                 520                 525

Cys Glu Pro Asn Pro Cys Gln Asn Gly Ala Gln Cys Tyr Asn Arg Ala
530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
            595                 600                 605

Ser Gly Gly Lys Phe Thr Cys Asp Cys Asn Lys Gly Phe Thr Gly Thr
        610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
```

```
                    645                 650                 655
Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
            725                 730                 735

Gly Thr Thr Cys Asn Ile Ala Arg Asn Ser Ser Cys Leu Pro Asn Pro
        740                 745                 750

Cys His Asn Gly Gly Thr Cys Val Val Asn Gly Glu Ser Phe Thr Cys
    755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
            805                 810                 815

Cys Arg Ile Asn Ile Asn Glu Cys Gln Ser Ser Pro Cys Ala Phe Gly
        820                 825                 830

Ala Thr Cys Val Asp Glu Ile Asn Gly Tyr Arg Cys Val Cys Pro Pro
    835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Cys
865                 870                 875                 880

Asn Thr Cys Gln Cys Leu Asn Gly Arg Ile Ala Cys Ser Lys Val Trp
            885                 890                 895

Cys Gly Pro Arg Pro Cys Leu Leu His Lys Gly His Ser Glu Cys Pro
        900                 905                 910

Ser Gly Gln Ser Cys Ile Pro Ile Leu Asp Asp Gln Cys Phe Val His
    915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
            965                 970                 975

Glu His Ile Cys Ser Glu Leu Arg Asn Leu Asn Ile Leu Lys Asn Val
        980                 985                 990

Ser Ala Glu Tyr Ser Ile Tyr Ile Ala Cys Glu Pro Ser Pro Ser Ala
    995                 1000                1005

Asn Asn Glu Ile His Val Ala Ile Ser Ala Glu Asp Ile Arg Asp Asp
    1010                1015                1020

Gly Asn Pro Ile Lys Glu Ile Thr Asp Lys Ile Ile Asp Leu Val Ser
1025                1030                1035                1040

Lys Arg Asp Gly Asn Ser Ser Leu Ile Ala Ala Val Ala Glu Val Arg
            1045                1050                1055

Val Gln Arg Arg Pro Leu Lys Asn Arg Thr Asp Phe Leu Val Pro Leu
        1060                1065                1070
```

-continued

```
Leu Ser Ser Val Leu Thr Val Ala Trp Ile Cys Cys Leu Val Thr Ala
    1075                1080                1085
Phe Tyr Trp Cys Leu Arg Lys Arg Arg Lys Pro Gly Ser His Thr His
    1090                1095                1100
Ser Ala Ser Glu Asp Asn Thr Thr Asn Asn Val Arg Glu Gln Leu Asn
1105                1110                1115                1120
Gln Ile Lys Asn Pro Ile Glu Lys His Gly Ala Asn Thr Val Pro Ile
            1125                1130                1135
Lys Asp Tyr Glu Asn Lys Asn Ser Lys Met Ser Lys Ile Arg Thr His
        1140                1145                1150
Asn Ser Glu Val Glu Glu Asp Met Asp Lys His Gln Gln Lys Ala
    1155                1160                1165
Arg Phe Ala Lys Gln Pro Ala Tyr Thr Leu Val Asp Arg Glu Glu Lys
    1170                1175                1180
Pro Pro Asn Gly Thr Pro Thr Lys His Pro Asn Trp Thr Asn Lys Gln
1185                1190                1195                1200
Asp Asn Arg Asp Leu Glu Ser Ala Gln Ser Leu Asn Arg Met Glu Tyr
            1205                1210                1215
Ile Val

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      nucleotide
<220> FEATURE:
<221> NAME/KEY: CDS
<222> LOCATION: (1)..(24)

<400> SEQUENCE: 12 gat tat aaa gat gat gat gat aaa tga                              27
Asp Tyr Lys Asp Asp Asp Asp Lys
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Tyr Lys Asp Asp Asp Asp Lys
 1               5

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
tggcartgya aytgycarga                                            20

<210> SEQ ID NO 15
<211> LENGTH: 20
<212> TYPE: DNA
<213> ORGANISM: Artificial Sequence
```

```
<220> FEATURE:
<223> OTHER INFORMATION: Description of Artificial Sequence: Primer

<400> SEQUENCE: 15
atyttyttyt crcarttraa                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (12)
<223> OTHER INFORMATION: a, t, c, g, other or unknown

<400> SEQUENCE: 16
tgcststgyg anaccaactg                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
tttatktcrc awktckgwcc                                               20

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 18
tcgcgcgtgg agcgaagcag catgg                                         25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
ggaattcgat atcaagctta tcgat                                         25

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 20
tcacccgccc tggccctcta gcttctca                                      28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Primer
```

```
<400> SEQUENCE: 21
ggacgcgtgg atccactagt tctagagc                                          28

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: Primer

<400> SEQUENCE: 22
tcatttatca tcatcatctt tataatcccc gccctggccc tctagcttct cagtg           55

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 23
aaccatcccc gagggtgtct gctggaagcc aggctca                                37

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 24
cctctagagt cgcggccgtc gcactcattt acc                                    33

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 25
aaggatcccc gccctggccc tctagcttc                                         29

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 26
cctctagacg cgtagagcgg ccgccaccgc ggtgga                                 36

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 27
tcacacctca gttgctatga cgcac                                             25

<210> SEQ ID NO 28
<211> LENGTH: 28
```

```
<212> TYPE: DNA
<213> ORGANISM: Artificial Sequence
<220> FEATURE:
<223> OTHER INFORMATION: Description of Artificial Sequence: Primer

<400> SEQUENCE: 28
ggacgcgtgg atccactagt tctagagc                                        28

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 29
tcatttatca tcatcatctt tataatccac ctcagttgct atgacgcact c              51

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 30
cggcgcagcg atgcgttccc cacgg                                           25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 31
ggaattcgat atcaagctta tcgat                                           25

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 32
tcaatctgtt ctgttgttca gaggccg                                         27

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 33
ggacgcgtgg atccactagt tctagagc                                        28

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 34
```
tcatttatca tcatcatctt tataatcatc tgttctgttg ttcagaggcc g            51

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 35
aaggatccgt tctgttgttc agaggccgcc t                                  31

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 36
cctctagacg cgtagagcgg ccgccaccgc ggtgga                             36

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 37
ctatacgatg tactccattc ggtttaag                                      28

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 38
ggacgcgtct agagtcgacc tgcaggcatg c                                  31

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 39
ctatttatca tcatcatctt tataatctac gatgtactcc attcggttta ag           52

<210> SEQ ID NO 40
<211> LENGTH: 45
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(6)
<223> OTHER INFORMATION: Variable amino acid
<220> FEATURE:

```
<221> NAME/KEY: MOD_RES
<222> LOCATION: (9)..(11)
<223> OTHER INFORMATION: Variable amino acid
<220> FEATURE:
<221> NAME/KEY: MOD_RES
<222> LOCATION: (13)..(15)
<223> OTHER INFORMATION: Variable amino acid
<220> FEATURE:
<221> NAME/KEY: MOD_RES
<222> LOCATION: (22)
<223> OTHER INFORMATION: Variable amino acid
<220> FEATURE:
<221> NAME/KEY: MOD_RES
<222> LOCATION: (26)..(27)
<223> OTHER INFORMATION: Variable amino acid
<220> FEATURE:
<221> NAME/KEY: MOD_RES
<222> LOCATION: (29)..(31)
<223> OTHER INFORMATION: Variable amino acid
<220> FEATURE:
<221> NAME/KEY: MOD_RES
<222> LOCATION: (33)..(35)
<223> OTHER INFORMATION: Variable amino acid
<220> FEATURE:
<221> NAME/KEY: MOD_RES
<222> LOCATION: (37)..(38)
<223> OTHER INFORMATION: Variable amino acid
<220> FEATURE:
<221> NAME/KEY: MOD_RES
<222> LOCATION: (41)
<223> OTHER INFORMATION: Variable amino acid
<220> FEATURE:
<221> NAME/KEY: MOD_RES
<222> LOCATION: (43)..(44)
<223> OTHER INFORMATION: Variable amino acid

<400> SEQUENCE: 40

Xaa Xaa Cys Xaa Xaa Xaa Tyr Tyr Xaa Xaa Xaa Cys Xaa Xaa Xaa Cys
 1               5                  10                  15

Arg Pro Arg Asp Asp Xaa Phe Gly His Xaa Xaa Cys Xaa Xaa Xaa Gly
            20                  25                  30

Xaa Xaa Xaa Cys Xaa Xaa Gly Trp Xaa Gly Xaa Xaa Cys
        35                  40                  45

<210> SEQ ID NO 41
<211> LENGTH: 45
<212> TYPE: PRT
<213> ORGANISM: Homo sapiens

<400> SEQUENCE: 41

Phe Val Cys Asp Glu His Tyr Tyr Gly Glu Gly Cys Ser Val Phe Cys
 1               5                  10                  15

Arg Pro Arg Asp Asp Ala Phe Gly His Phe Thr Cys Gly Glu Arg Gly
            20                  25                  30

Glu Lys Val Cys Asn Pro Gly Trp Lys Gly Pro Tyr Cys
        35                  40                  45

<210> SEQ ID NO 42
<211> LENGTH: 45
<212> TYPE: PRT
<213> ORGANISM: Drosphila sp.

<400> SEQUENCE: 42

Val Thr Cys Asp Leu Asn Tyr Tyr Gly Ser Gly Cys Ala Lys Phe Cys
 1               5                  10                  15

Arg Pro Arg Asp Asp Ser Phe Gly His Ser Thr Cys Ser Glu Thr Gly
            20                  25                  30

Glu Ile Ile Cys Leu Thr Gly Trp Gln Gly Asp Tyr Cys
```

```
              35                  40                  45
```

<210> SEQ ID NO 43
<211> LENGTH: 45
<212> TYPE: PRT
<213> ORGANISM: Xenopus laevis

<400> SEQUENCE: 43

```
Phe Val Cys Asp Glu Tyr Tyr Tyr Gly Glu Gly Cys Ser Asp Tyr Cys
  1               5                  10                  15

Arg Pro Arg Asp Asp Ala Phe Gly His Phe Ser Cys Gly Glu Arg Gly
             20                  25                  30

Glu Lys Leu Cys Asn Pro Gly Trp Lys Gly Leu Tyr Cys
             35                  40                  45
```

<210> SEQ ID NO 44
<211> LENGTH: 45
<212> TYPE: PRT
<213> ORGANISM: Gallus sp.

<400> SEQUENCE: 44

```
Phe Val Cys Asp Glu His Tyr Tyr Gly Glu Gly Cys Ser Val Phe Cys
  1               5                  10                  15

Arg Pro Arg Asp Asp Arg Phe Gly His Phe Thr Cys Gly Glu Arg Gly
             20                  25                  30

Glu Lys Val Cys Asn Pro Gly Trp Lys Gly Gln Tyr Cys
             35                  40                  45
```

<210> SEQ ID NO 45
<211> LENGTH: 45
<212> TYPE: PRT
<213> ORGANISM: Murine sp.

<400> SEQUENCE: 45

```
Phe Val Cys Asp Glu His Tyr Tyr Gly Glu Gly Cys Ser Val Phe Cys
  1               5                  10                  15

Arg Pro Arg Asp Asp Ala Phe Gly His Phe Thr Cys Gly Asp Arg Gly
             20                  25                  30

Glu Lys Met Cys Asp Pro Gly Trp Lys Gly Gln Tyr Cys
             35                  40                  45
```

<210> SEQ ID NO 46
<211> LENGTH: 45
<212> TYPE: PRT
<213> ORGANISM: Homo sapiens

<400> SEQUENCE: 46

```
Val Thr Cys Asp Asp Tyr Tyr Tyr Gly Phe Gly Cys Asn Lys Phe Cys
  1               5                  10                  15

Arg Pro Arg Asp Asp Phe Phe Gly His Tyr Ala Cys Asp Gln Asn Gly
             20                  25                  30

Asn Lys Thr Cys Met Glu Gly Trp Met Gly Pro Glu Cys
             35                  40                  45
```

<210> SEQ ID NO 47
<211> LENGTH: 45
<212> TYPE: PRT
<213> ORGANISM: Drosophila sp.

<400> SEQUENCE: 47

```
Val Gln Cys Ala Val Thr Tyr Tyr Asn Thr Thr Cys Thr Thr Phe Cys
```

-continued

```
                1               5                  10                 15
Arg Pro Arg Asp Asp Gln Phe Gly His Tyr Ala Cys Gly Ser Glu Gly
                        20                  25                  30
Gln Lys Leu Cys Leu Asn Gly Trp Gln Gly Val Asn Cys
            35                  40                  45

<210> SEQ ID NO 48
<211> LENGTH: 45
<212> TYPE: PRT
<213> ORGANISM: Rattus sp.

<400> SEQUENCE: 48

Val Thr Cys Asp Asp His Tyr Tyr Gly Phe Gly Cys Asn Lys Phe Cys
 1               5                  10                  15
Arg Pro Arg Asp Asp Phe Phe Gly His Tyr Ala Cys Asp Gln Asn Gly
                        20                  25                  30
Asn Lys Thr Cys Met Glu Gly Trp Met Gly Pro Glu Cys
            35                  40                  45
```